United States Patent
Chou et al.

(10) Patent No.: US 11,940,443 B2
(45) Date of Patent: *Mar. 26, 2024

(54) ASSAYING CELLS AND NON-CELL ANALYTES IN A SAMPLE IN PARALLEL

(71) Applicant: Essenlix Corporation, Monmouth Junction, NJ (US)

(72) Inventors: Stephen Y. Chou, Princeton, NJ (US); Wei Ding, East Windsor, NJ (US); Ji Li, Princeton, NJ (US); Yufan Zhang, Monmouth Junction, NJ (US)

(73) Assignee: Essenlix Corporation, Monmouth Junction, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/964,870

(22) PCT Filed: Jan. 25, 2019

(86) PCT No.: PCT/US2019/015309
§ 371 (c)(1),
(2) Date: Jul. 24, 2020

(87) PCT Pub. No.: WO2019/148054
PCT Pub. Date: Aug. 1, 2019

(65) Prior Publication Data
US 2021/0011001 A1  Jan. 14, 2021

Related U.S. Application Data

(63) Continuation of application No. PCT/US2019/013388, filed on Jan. 11, 2019.
(60) Provisional application No. 62/621,761, filed on Jan. 25, 2018.

(51) Int. Cl.
*G01N 33/543* (2006.01)
*B01L 3/00* (2006.01)
*G01N 21/29* (2006.01)
*G01N 33/50* (2006.01)

(52) U.S. Cl.
CPC .. *G01N 33/54313* (2013.01); *B01L 3/502746* (2013.01); *G01N 21/29* (2013.01); *G01N 33/5005* (2013.01); *B01L 2300/0816* (2013.01)

(58) Field of Classification Search
None
See application file for complete search history.

(56) References Cited

U.S. PATENT DOCUMENTS

| | | | |
|---|---|---|---|
| 1,022,521 A | 5/1977 | Hall, V et al. | |
| 6,083,761 A | 7/2000 | Kedar et al. | |
| 9,422,517 B2 * | 8/2016 | Chen | B01L 3/502761 |

(Continued)

FOREIGN PATENT DOCUMENTS

| CN | 108956241 | * 12/2018 |
|---|---|---|
| EP | 0961110 A2 | 12/1999 |

(Continued)

OTHER PUBLICATIONS

International Report on Patentability for PCT/US2019/015309 established by IPEA/US completed on Feb. 11, 2020.

*Primary Examiner* — Bao-Thuy L Nguyen
*Assistant Examiner* — Jennifer H. Tieu

(57) ABSTRACT

Among other things, the present invention is related to bio/chemical sampling, sensing, assays and applications.

106 Claims, 5 Drawing Sheets

(56) References Cited

U.S. PATENT DOCUMENTS

| | | |
|---|---|---|
| 2005/0112277 A1 | 5/2005 | Banerjee et al. |
| 2010/0216248 A1 | 8/2010 | Wardlaw |
| 2012/0108787 A1 | 5/2012 | Lue |
| 2013/0065788 A1 | 3/2013 | Glezer et al. |
| 2013/0105200 A1 | 5/2013 | Ohigashi et al. |
| 2013/0157288 A1 | 6/2013 | Kilfeather et al. |
| 2014/0323330 A1 | 10/2014 | Bergo |
| 2016/0033496 A1 | 2/2016 | Chou |
| 2018/0156775 A1* | 6/2018 | Chou .................. A61B 5/0836 |

FOREIGN PATENT DOCUMENTS

| | | |
|---|---|---|
| EP | 3270156 A1 | 1/2018 |
| WO | 2011102903 A1 | 8/2011 |
| WO | 2017112957 A1 | 12/2016 |
| WO | 2017048871 A1 | 3/2017 |
| WO | 2018231877 A1 | 12/2018 |

\* cited by examiner

ASSAYING CELLS AND NON-CELL ANALYTES IN A SAMPLE IN PARALLEL

CROSS REFERENCING

This application is a National Stage entry (§ 371) application of International Application No. PCT/US2019/015309, filed on Jan. 25, 2019, which claims the benefit of U.S. Provisional Patent Application No. 62/621,761, filed on Jan. 25, 2018, and International Application No. PCT/US2019/013388, filed on Jan. 11, 2019, the contents of which are relied upon and incorporated herein by reference in their entirety.

The entire disclosure of any publication or patent document mentioned herein is entirely incorporated by reference.

FIELD

The present disclosure is related to the field of bio/chemical sampling, sensing, assays and applications.

BACKGROUND

A large proportion of antibiotics are prescribed to treat conditions in which antibiotics are of little or no benefit. Excessive and inappropriate use of antibiotics, leading to the emergence of increasingly resistant bacteria, has become a severe problem worldwide. The individual health care practitioner often faces the dilemma of how to identify patients who need—and particularly those who do not need—antibiotic therapy.

BRIEF SUMMARY

In certain embodiments, the present disclosure provides a device for assaying a target cell and a non-cell analyte in a liquid sample, comprising a first plate, a second plate, a plurality of spacers, a plurality of particles, and a capture agent, wherein: the first and second plates are movable relative to each other into different configurations, including an open configuration and a closed configuration; each of the plates has, on its respective surface, a sample contact area for contacting a sample that contains or is suspected of containing one or more target cells and a non-cell analyte; the spacers comprises a periodic array of pillars that have a uniform height, and are fixed on the first plate; the particles have a size of 0.2 um to 100 um and are, in an open configuration, randomly distributed in the sample contact area of the first plate; and a capture agent is attached on the particles, wherein the capture agent specifically binds the non-cell analyte, wherein the non-cell analyte is capable of binding an optical label forming a labeled non-cell analyte; wherein an open configuration is the configuration, in which: the two plates are separated apart, and the sample is deposited on one or both plate; wherein a closed configuration is the configuration which is configured after the sample deposition in the open configuration; and in the closed configuration: a relevant sample volume is compressed by the two plates into a layer of substantially uniform thickness and is substantially stagnant relative to the plates, and the uniform thickness of the layer is confined by the plates and is regulated by the plates and the spacers; wherein a relevant sample volume of the sample was analyzed for assaying the non-cell analyte and the target cells; and wherein the uniform thickness and the geometry of the particles are configured to make, in the closed configuration, there are no significant overlaps between the one or more target cells, between the particles, and between the target cells and the particles.

In certain embodiments, the present disclosure provides a device for assaying a target cell and a non-cell analyte in a liquid sample, comprising: a first plate, a second plate, a plurality of spacers, a plurality of particles, and a capture agent, wherein: the first and second plates are movable relative to each other into different configurations, including an open configuration and a closed configuration; each of the plates has, on its respective surface, a sample contact area for contacting a sample that contains or is suspect to containing one or more target cells and a non-cell analyte; the spacers comprises an array of pillars that have a uniform height of 150 um less, and are fixed on the first plate; the particles have a size of 0.2 um to 100 um and are, in an open configuration, randomly distributed in the sample contact area of the first plate; and a capture agent is attached on the particles, wherein the capture agent specifically binds the non-cell analyte, wherein the non-cell analyte is capable of binding an optical label forming a labeled non-cell analyte; wherein the uniform thickness and the geometry of the particles are configured to make, in the closed configuration, there are no significant overlaps between the one or more target cells, between the particles, and between the target cells and the particles, and the uniform thickness of the layer is confined by the plates and is regulated by the plates and the spacers; and wherein the relevant sample volume is a portion or entire volume of the sample, wherein the relevant sample volume is analyzed for assaying the non-cell analyte and the target cells, wherein the number of the particles in the relevant sample volume are configured to be, in a closed configuration, at least 10.

In certain embodiments, the present disclosure provides an apparatus for assaying a target cell and a non-cell analyte in a liquid sample, comprising: a first plate, a second plate, a plurality of spacers, a plurality of particles, a capture agent, an imager, and a processor, wherein: the first and second plates are movable relative to each other into different configurations, including an open configuration and a closed configuration; each of the plates has, on its respective surface, a sample contact area for contacting a sample that contains one or more target cells and a non-cell analyte; the particles have a size of 0.2 um to 100 um and are, in a closed configuration, randomly distributed in the sample; the spacers comprise an array of pillars that have a uniform height of 150 um or less, and are fixed on the first plate; the capture agent is attached on the particles, wherein the capture agent specifically binds the non-cell analyte, wherein the non-cell analyte is capable of binding an optical label forming a labeled non-cell analyte; the imager takes at least one image of a relevant sample volume; the processor is configured to process the at least one image to (i) detect the non-cell analyte by analyzing the images of at least 10 particles, and (ii) detect the target cell analyte; wherein an open configuration is the configuration, in which: the two plates are separated apart, and the sample is deposited on one or both plate; wherein a closed configuration is the configuration which is configured after the sample deposition in the open configuration; and in the closed configuration: a relevant sample volume is compressed by the two plates into a layer of substantially uniform thickness and is substantially stagnant relative to the plates, and the uniform thickness of the layer is confined by the plates and is regulated by the plates and the spacers; wherein the uniform thickness and the geometry of the particles are configured to make, in the closed configuration, there are no significant overlaps between the one or more target cells, between the particles, and between the target cells and the particles; and wherein the relevant sample volume is a portion or entire volume of the sample, and wherein the number of the particles in the relevant volume are configured to be, in a closed configuration, at least 10; wherein the processor is configured to process the at least one image to (i) detect the non-cell analyte by analyzing the images of at least 10 particles, and (ii) detect the target cell analyte.

In certain embodiments, the present disclosure provides a device comprising: a first plate; a second plate having a sample contact area on a surface thereof; wherein the first plate and the second plate are movable relative to each other into: an open configuration in which the first plate and the second plate are at least partially separated such that a sample containing one or more target cells and a non-cell analyte can be deposited therebetween, and a closed configuration in which the first plate is placed on top of the second plate thereby compressing at least a portion of the sample between the first plate and the second plate into a layer having uniform thickness; one or more spacers, said one or more spacers comprising a periodic array of pillars; and wherein the uniform thickness of the layer is regulated by the one or more spacers, a plurality of particles having one or more capture agents disposed on a surface thereof; wherein, in the closed configuration, the first plate and the second plate compress at least a portion of the sample such that there is substantially no overlap between (i) the one or more target cells, (ii) the plurality of particles, and (iii) the one or more target cells and the plurality of particles.

In certain embodiments, the one or more spacers are fixed onto a surface of the second plate. In certain embodiments, the plurality of particles have a diameter of 0.2 um to 100 um. In certain embodiments, the plurality of particles are randomly distributed in the sample contact area of the second plate when the first plate and the second plate are in the open configuration. In certain embodiments, the capture agent specifically binds to a labeled targeted analyte comprising the non-cell analyte attached to an optical label. In certain embodiments, the one or more spacers have a uniform height. In certain embodiments, the uniform height of the one or more spacers is at least about 0.8 times the particle diameter. In certain embodiments, the uniform height of the one or more spacers is less than about 200 um. In certain embodiments, the uniform height of the one or more spacers is between at least about 0.8 times the particle diameter and about 200 um. In certain embodiments, the device further comprises an imager for obtaining an image of a relevant volume of the sample. In certain embodiments, the relevant volume is a portion or entire volume of the at least part of the sample, and wherein the number of the particles in the relevant volume are configured to be, in a closed configuration, at least 10. In certain embodiments, the device further comprises a processor for processing the image. In certain embodiments, the processing comprises at least one of (i) detecting the non-cell analyte by analyzing one or more images of at least 10 particles, and (ii) detecting the target cell analyte.

In certain embodiments, the present disclosure provides a method for assaying cells and a non-cell analytes in a liquid sample, comprising: having a device of the present disclosure; having a sample containing or suspected of containing one or more target cells and a non-cell analyte; having an optical label that is capable of binding the non-cell analyte forming a labeled non-cell analyte; depositing, in an open configuration, the sample of the sample contact area of the device, making, after step (d) the device in the closed configuration, thereby compressing at least a portion of the sample into a layer having uniform thickness; taking, using a imager, at least one image of a sample relevant sample volume, wherein the imager is capable of imaging the optical label and the target cell; and analyzing at least one image to detect an existence or an amount of (i) the target cell and/or (ii) the non-cell analyte.

In certain embodiments, the present disclosure provides a method for assaying cells and a non-cell analytes in a liquid sample, comprising: having a device of present disclosure; having a sample containing or suspected of containing one or more target cells and a non-cell analyte; having an optical label that is capable of binding the non-cell analyte forming a labeled non-cell analyte; depositing, in an open configuration, the sample of the sample contact area of the device, making, after step (d) the device in the closed configuration, thereby compressing at least a portion of the sample into a layer having uniform thickness; taking, using a imager, at least one image of the sample relevant sample volume, wherein the imager is capable of imaging the optical label and the target cell; and analyzing, using a processor, at least one image to detect an existence or an amount of (i) the target cell and/or (ii) the non-cell analyte; wherein the processor is configured to process the at least one image to (i) detect the non-cell analyte by analyzing the images of at least 10 particles, and (ii) detect the target cell analyte.

In certain embodiments, in detection of the non-cell analyte, the analyzing the images of at least 10 particles is by digital counting, wherein in the digital counting, an existence or an amount of non-cell analyte in the sample is determined from the number or the percentage of the beads that have a light signal above a threshold value, wherein the percentage is the ratio of the number of the beads above the threshold to the number of the breads that are below. In certain embodiments, in detection of the non-cell analyte, the analyzing the images of at least 10 particles is by an analog counting, wherein the analog counting determines an existence or an amount of non-cell analyte in the sample from the optical signal amplitude from all beads in the relevant sample area. In certain embodiments, the device or method further comprises two or more images of a common area/volume of the sample layer, wherein the common area of the sample layer is an area of the sample containing at least one particle of the one or more particles. In certain embodiments, the device or method further comprising two or more images wherein at least one image is dark field image and at least one is bright field image. In certain embodiments, the thickness of the sample layer is sufficient to produce a monolayer of the target cells between the plates. In certain embodiments, the thickness of the sample layer is sufficient to produce no substantial overlap between the one or more target cells between the plates. In certain embodiments, the one or more particles have a geometry (shape and size) that are sufficient to (i) produce a monolayer of the particles between the plates and (ii) produce no substantial overlap between the particles between the plates. In certain embodiments, the one or more particles have a density that are sufficient to (i) produce a monolayer of the particles between the plates and (ii) produce no substantial overlap between the particles between the plates. In certain embodiments, the one or more particles are mixed with the sample prior to depositing the sample into the device. In certain embodiments, the one or more particles are disposed on at least one of the first plate and the second plate prior to deposition of the sample, and then mixed with the sample upon deposition of the sample onto the device. In certain embodiments, the one or more particles have various shape.

In certain embodiments, the one or more particles have a maximum dimension in the range of 0.05 um to 100 um. In certain embodiments, the non-cell analyte is detected using a competitive assay, comprising a step of providing a labeled competitive detection agent that competes with the non-cell analyte, if present, for binding to the capture agent for the analyte. In certain embodiments, the non-cell analyte is detected using a non-competing assay, comprising a step of providing a labeled detection agent that specifically binds to another binding site of the non-cell analyte, wherein the other binding site is the binding set different from the binding site by the capture agent. In certain embodiments, one of the images is a direct image that comprises information of the topology (i.e. geometry) and position of the particle in the common area; and the other image is a signal image that is configured to comprises signal from the labeled competitive detection agents as a major signal of the image. In certain embodiments, the sample holder comprises a first and second plates are movable relative to each other into different configurations, including an open configuration and a closed configuration.

In certain embodiments, the present disclosure provides a method for diagnosing virus infection or bacterial infection of a subject, comprising: obtaining a device comprising a first plate, a second plate, and a plurality of particles comprising one or more capture agents coupled thereto, wherein said plurality of particles are disposed along at least one of said first plate and said second plate substantially as a monolayer, wherein said one or more capture agents are capable of associating with an analyte, and wherein said device comprises: an open configuration wherein said first plate and said second plate are at least partially separated thereby exposing a sample contact area comprising said plurality of particles, said sample contact area disposed on at least one of said first plate and said second plate; and a closed configuration wherein said first plate and said second plate are substantially parallel and comprise a space therebetween; contacting said device with said sample comprising said analyte and one or more cells, wherein said device is in said open configuration; placing said device in said closed configuration, thereby containing at least a portion of said sample within said space, wherein a thickness of said at least a portion of said sample within said space is substantially uniform, and wherein, in said closed configuration, said one or more cells within said space are disposed substantially as a monolayer; and taking one or more images of a common area of the thin sample layer, wherein the common area of the sample layer is an area of the sample contains at least one of: a particle of said plurality of particles; and a cell of said one or more cells.

In certain embodiments, the method further comprises determining, using a mobile electronic device: (i) one or more first values corresponding an amount of said analyte associated with said one or more capture agents; and (ii) one or more second values corresponding to an amount of said one or more cells within said sample. In certain embodiments, said plurality of particles are removably coupled to said at least one of said first plate and said second plate. In certain embodiments, said plurality of particles are selected from the group consisting of glass beads, magnetic beads, polystyrene beads, latex particles, reporter molecules, a fluorescent molecule, a dye molecule, a non-selective dye molecule, and a redox-reactive molecule. In certain embodiments, said plurality of particles comprises a first plurality of particles and a second plurality of particles, wherein said first plurality of particles comprise one or more first capture agents coupled thereto, and wherein said second plurality of particles comprise one or more second capture agents coupled thereto. In certain embodiments, said one or more first capture agents are capable of associating with a first epitope on said analyte, and wherein said one or more second capture agents are capable of associating with a second epitope on said analyte. In certain embodiments, said first plurality of particles is disposed along said first plate, and said second plurality of particles is disposed along said second plate. In certain embodiments, said first plurality of particles is selected from the group consisting of glass beads, magnetic beads, polystyrene beads, and latex particles. In certain embodiments, said second plurality of particles is selected from the group consisting of reporter molecules, a fluorescent molecule, a dye molecule, a non-selective dye molecule, and a redox-reactive molecule. In certain embodiments, at least one of said one or more first capture agents and said one or more second capture agents are capable of specifically associating with said analyte. In certain embodiments, said device further comprises one or more spacers within said space and disposed along at least one of said first plate or said second plate. In certain embodiments, said one or more spacers determine a distance between said first plate and said second plate. In certain embodiments, a length of said one or more spacers along a direction from said first plate to said second plate is at most about 500 micrometers, at most about 250 micrometers, at most about 100 micrometers, at most about 90 micrometers, at most about 80 micrometers, at most about 70 micrometers, at most about 60 micrometers, at most about 50 micrometers, at most about 40 micrometers, at most about 30 micrometers, at most about 25 micrometers, at most about 20 micrometers, at most about 15 micrometers, at most about 10 micrometers, at most about 5 micrometers, at most about 4 micrometers, at most about 3 micrometers, at most about 2 micrometers, at most about 1 micrometers, at most about 0.5 micrometers, or at most about 0.1 micrometers. In certain embodiments, a length of said one or more spacers along a direction from said first plate to said second plate is less than about or about equal to an average diameter of said one or more cells in said sample. In certain embodiments, said thickness of said at least a portion of said sample within said space is at most about 500 micrometers, at most about 250 micrometers, at most about 100 micrometers, at most about 90 micrometers, at most about 80 micrometers, at most about 70 micrometers, at most about 60 micrometers, at most about 50 micrometers, at most about 40 micrometers, at most about 30 micrometers, at most about 25 micrometers, at most about 20 micrometers, at most about 15 micrometers, at most about 10 micrometers, at most about 5 micrometers, at most about 4 micrometers, at most about 3 micrometers, at most about 2 micrometers, at most about 1 micrometers, at most about 0.5 micrometers, at most about 0.1 micrometers, or at most about 0.05 micrometers. In certain embodiments, said plurality of particles have various shape. In certain embodiments, said plurality of particles have a maximum dimension of about 500 micrometers, about 250 micrometers, about 100 micrometers, about 90 micrometers, about 80 micrometers, about 70 micrometers, about 60 micrometers, about 50 micrometers, about 40 micrometers, about 30 micrometers, about 25 micrometers, about 20 micrometers, about 15 micrometers, about 10 micrometers, about 5 micrometers, about 4 micrometers, about 3 micrometers, about 2 micrometers, about 1 micrometers, about 0.5 micrometers, about 0.1 micrometers, or about 0.05 micrometers. In certain embodiments, said one or more cells within said space are disposed substantially as a non-confluent monolayer. In certain embodiments, said one or more cells within said space are in suspension. In certain embodiments, said determining comprises obtaining one or more images of an area comprising said at least a portion of said sample within said space, wherein said imaged area includes at least one of said plurality of particles. In certain embodiments, said one or more first values correspond to an intensity of energy emitted by said particle. In certain embodiments, the method further comprises contacting said sample with a cell dye capable of associating with said one or more cells. In certain embodiments, said one or more second values correspond to an intensity of energy emitted by said cell dye. In certain embodiments, the method further comprises using an algorithm to determine a relationship between said one or more first values and said one or more second values. In certain embodiments, the method further comprises classifying a level of infection in a subject from whom said sample was obtained based on said relationship between said one or more first values and said one or more second values. In certain embodiments, said infection is a viral infection, a bacterial infection, or a combination thereof. In certain embodiments, said one or more cells are selected from the group consisting of white blood cells, leukocytes, granulocytes, agranulocytes, myeloid cells, lymphoid cells, neutrophils, eosinophils, basophils, lymphocytes, T-cells, B-cells, natural killer cells, and monocytes. In certain embodiments, said analyte is selected from the group consisting of a polypeptide, a protein, a tagged protein, a fusion protein, an antibody, a small molecule, a virus particle, a bacteria, C-reactive protein, and any fragment thereof. In certain embodiments, the method further comprises contacting at least a portion of said sample with a competing detection agent capable of associating with said one or more capture agents. In certain embodiments, said competing detection agent competitively binds to said one or more capture agents with said analyte. In certain embodiments, the method further comprises contacting at least a portion of said sample with a supplementary detection agent capable of associating with said analyte. In certain embodiments, said one or more capture agents are capable of associating with a first epitope on said analyte, and wherein said supplementary detection agent is capable of associating with a second epitope on said analyte. In certain embodiments, said method is performed in less than about 10 sec, less than about 20 sec, less than about 30 sec, less than about 40 sec, less than about 50 sec, less than about 60 sec, less than about 120 sec, less than about 180 sec, less than about 240 sec, less than about 300 sec, less than about 400 sec, less than about 500 sec, less than about 1000 sec, or less than about 2000 sec. In certain embodiments, said method does not comprise contacting at least a portion of said sample with a wash buffer. In certain embodiments, the method is done in the absence of any washing steps. In certain embodiments, the first and second plates are pressed together by hand. In certain embodiments, the non-cell analyte is a polypeptide, nucleic acid, or metabolite. In certain embodiments, the sample is a bodily fluid. In certain embodiments, the bodily fluid is amniotic fluid, aqueous humour, vitreous humour, blood, whole blood, fractionated blood, plasma, serum, breast milk, cerebrospinal fluid, cerumen, chyle, chime, endolymph, perilymph, feces, gastric acid, gastric juice, lymph, mucus, nasal drainage, phlegm, pericardial fluid, peritoneal fluid, pleural fluid, pus, rheum, saliva, sebum, semen, sputum, sweat, synovial fluid, tears, vomit, urine, and exhaled breath condensate. In certain embodiments, the method further comprises diagnosing a disease based on the results. In certain embodiments, the disease is cancer, an inflammatory disease or an infectious disease. In certain embodiments, the method detects multiple different non-cell analytes.

In certain embodiments, the present disclosure provides a kit for assaying a target cell and a non-cell analyte in a liquid sample, comprising: a first plate, a second plate, one or plurality of particles, and a capture agent, wherein: the first and second plates are movable relative to each other into different configurations, including an open configuration and a closed configuration; each of the plates has, on its respective surface, a sample contact area for contacting a sample that contains one or more target cells and a non-cell analyte; and the particles have a size of 0.2 um to 100 um and have a capture agent attached on their surface, wherein the capture agent specifically bind to the non-cell analyte; wherein an open configuration is the configuration, in which: the two plates are separated apart, and the sample is deposited on one or both plate; wherein a closed configuration is the configuration which is configured after the sample deposition in the open configuration; and in the closed configuration: at least part of the sample is compressed by the two plates into a layer of substantially uniform thickness and is substantially stagnant relative to the plates, and at least one of the particles is inside the at least part of the sample; and wherein the uniform thickness and the geometry of the particles are configured to make, in the closed configuration, (i) the one or more target cells do not substantially overlap with each other, and (ii) the particles do not substantially overlap with each other.

In certain embodiments, the present disclosure provides a kit, comprising: a device, the device comprising a first plate; a second plate; and a sample contact area disposed on one or both of the first plate and the second plate for contacting a sample comprising one or more particles having a capture agent attached to a surface thereof; wherein the first plate and the second plate are movable relative to each other into an open configuration or a closed configuration, wherein the open configuration is that the first plate and the second plate are at least partially separated such that a sample can be deposited there between; and wherein the closed configuration is that the first plate is placed on top of the second plate thereby compressing at least a portion of the sample between the first plate and the second plate into a layer having uniform thickness.

In certain embodiments, the kit further comprises instructions for using the device. In certain embodiments, the sample comprises one or more target cells. In certain embodiments, the sample comprises one or more non-cell analytes. In certain embodiments, the one or more particles have a diameter between 0.2 um and 100 um. In certain embodiments, the capture agent binds to the non-cell analyte. In certain embodiments, at least part of the sample is compressed by the first plate and the second plate into a layer of substantially uniform thickness. In certain embodiments, at least part of the sample is substantially stagnant relative to the plates. In certain embodiments, the sample thickness in the closed configuration is configured to (i) make the one or more target cells have a monolayer between the plates and (ii) have no substantial overlap between the one or more target cells. In certain embodiments, the one or more particles have a geometry (shape and size) that are configured to (i) make the particles have a monolayer between the plates and (ii) have no substantial overlap between the particles. In certain embodiments, the one or more particles have a density that are configured to (i) make the particles have a monolayer between the plates and (ii) have no substantial overlap between the particles. In certain embodiments, the device further comprises spacers on one or both of the first plate and the second plate. In certain embodiments, the device further comprises a labeled competing detection agent for competing with the analyte, if present, for binding to the capture agent for the analyte in a competitive assay. In certain embodiments, the device further comprises a labeled detection agent that specifically binds to an additional binding site of the analyte in a non-competitive assay, wherein the additional binding site is the binding site different from the binding site by the capture agent. In certain embodiments, the device further comprises an imager that images the target cell and the non-cell analyte when the sample are between the two plates and the plates are in a closed configuration.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

A skilled artisan will understand that the drawings, described below, are for illustration purposes only. In some Figures, the drawings are in scale. In the figures that present experimental data points, the lines that connect the data points are for guiding a viewing of the data only and have no other means. For clarity purposes, some elements are enlarged when illustrated in the Figures. It should be noted that the Figures do not intend to show the elements in strict proportion. The dimensions of the elements should be delineated from the descriptions herein provided and incorporated by reference. The drawings are not intended to limit the scope of the present invention in any way.

DETAILED DESCRIPTION

Figure 1A:
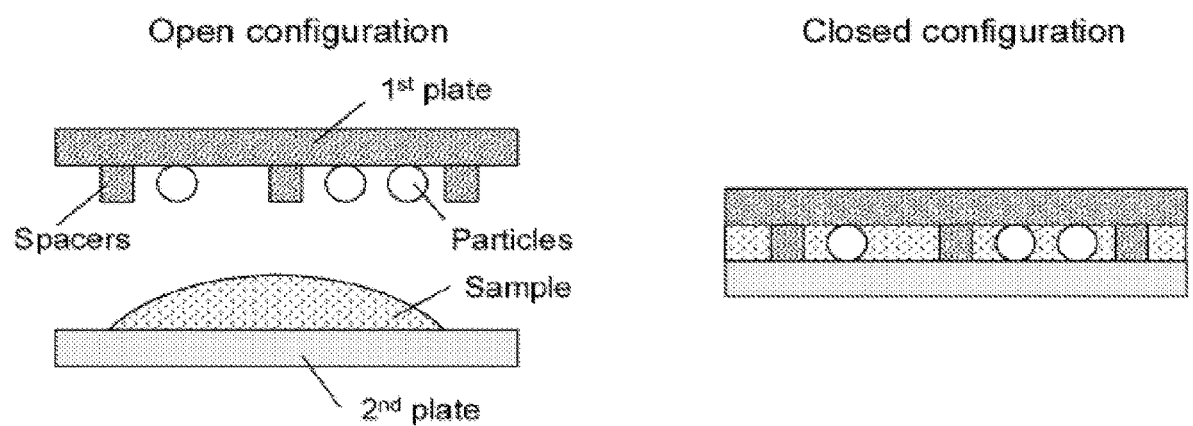
FIG. 1 provides schematic illustrations showing some of the exemplary processes of the present invention.

The following detailed description illustrates certain embodiments of the invention by way of example and not by way of limitation. If any, the section headings and any subtitles used herein are for organizational purposes only and are not to be construed as limiting the subject matter described in any way. The contents under a section heading and/or subtitle are not limited to the section heading and/or subtitle, but apply to the entire description of the present invention.

The citation of any publication is for its disclosure prior to the filing date and should not be construed as an admission that the present claims are not entitled to antedate such publication by virtue of prior invention. Further, the dates of publication provided can be different from the actual publication dates which can need to be independently confirmed.

Definitions

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present teachings, some exemplary methods and materials are now described.

As used herein, the term "monolayer" can refer to a layer of cells that is 1 cell thick, or a layer of molecules that is 1 molecule thick. In some embodiments, a monolayer or cells or molecules can be confluent. In some embodiments, a monolayer of cells or molecules (e.g., analytes) can be sub confluent. In some embodiments, a monolayer of cells or molecules can be sparse.

The terms "attach", "bind", "couple", and "link" are used interchangeably and refer to covalent interactions (e.g., by chemically coupling), or non-covalent interactions (e.g., ionic interactions, hydrophobic interactions, hydrogen bonds, hybridization, etc.), or molecules or cells dried onto a surface. The terms "specific", "specifically", or "specificity" refer to the preferential recognition, contact, and formation of a stable complex between a first molecule and a second molecule compared to that of the first molecule with any one of a plurality of other molecules (e.g., substantially less to no recognition, contact, or formation of a stable complex between the first molecule, such as a capture agent, and any one of the plurality of other molecules, such as an analyte).

An analyte, or target analyte, can be, but is not limited to, a polypeptide, a protein (e.g., C-reactive protein), a protein fragment, a tagged protein, a fusion protein, an antibody, an antibody fragment, a small molecule, a virus particle, a cell, or any fragment thereof.

A subject as described herein can be of any age and can be an adult, infant or child. In some cases, the subject is 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 years old, or within a range therein (e.g., between 2 and 20 years old, between 20 and 40 years old, or between 40 and 90 years old). A particular class of subjects that can benefit is subjects who have or are suspected of having an infection. Another particular class of subjects that can benefit is subjects who can be at higher risk of getting an infection. Furthermore, a subject treated by any of the methods or compositions described herein can be male or female. Any of the methods, devices, or kits disclosed herein can also be performed on a non-human subject, such as a laboratory or farm animal. Non-limiting examples of a non-human subjects include a dog, a goat, a guinea pig, a hamster, a mouse, a pig, a non-human primate (e.g., a gorilla, an ape, an orangutan, a lemur, or a baboon), a rat, a sheep, a cow, or a zebrafish.

As used herein, "virus" can refer to an obligate intracellular parasite of living but non-cellular nature, consisting of DNA or RNA and a protein coat. Viruses can range in diameter from about 20 to about 300 nm. Class I viruses (Baltimore classification) can have a double-stranded DNA as their genome; Class II viruses can have a single-stranded DNA as their genome; Class III can viruses have a double-stranded RNA as their genome; Class IV viruses can have a positive single-stranded RNA as their genome, the genome itself acting as mRNA; Class V viruses can have a negative single-stranded RNA as their genome used as a template for mRNA synthesis; and Class VI viruses can have a positive single-stranded RNA genome but with a DNA intermediate not only in replication but also in mRNA synthesis. Viruses can be recognized by the diseases they cause in plants, animals and prokaryotes. Viruses of prokaryotes are also known as bacteriophages.

As used herein, "fungus" can refer to a division of eukaryotic organisms that grow in irregular masses, without roots, stems, or leaves, and are devoid of chlorophyll or other pigments capable of photosynthesis. Each fungal organism can be unicellular to filamentous, and possess branched somatic structures (e.g., hyphae) surrounded by cell walls containing glucan or chitin or both, and contain true nuclei.

As used herein, "infection" can refer to invasion of the body of a multi-cellular organism with organisms that have the potential to cause disease.

The term "imprinted" means that a spacer and a plate are fixed monolithically by imprinting (i.e. embossing) a piece of a material to form the spacer on the plate surface. The material can be single layer of a material or multiple layers of the material.

The term "etched" means that a spacer and a plate are fixed monolithically by etching a piece of a material to form the spacer on the plate surface. The material can be single layer of a material or multiple layers of the material.

The term "fused to" means that a spacer and a plate are fixed monolithically by attaching a spacer and a plate together, the original materials for the spacer and the plate fused into each other, and there is clear material boundary between the two materials after the fusion.

The term "bonded to" means that a spacer and a plate are fixed monolithically by binding a spacer and a plate by adhesion.

The term "attached to" means that a spacer and a plate are connected together.

As will be apparent to those of skill in the art upon reading this disclosure, each of the individual embodiments described and illustrated herein has discrete components and features which can be readily separated from or combined with the features of any of the other several embodiments without departing from the scope or spirit of the present teachings. Any recited method can be carried out in the order of events recited or in any other order which is logically possible. One skilled artisan will appreciate that the present invention is not limited in its application to the details of construction, the arrangements of components, category selections, weightings, pre-determined signal limits, or the steps set forth in the description or drawings herein. The invention is capable of other embodiments and of being practiced or being carried out in many different ways.

Fast, Homogenous Staining of Cells and Non-Cell Analytes in Parallel

A large proportion of antibiotics is prescribed to treat conditions in which antibiotics are of little or no benefit. Excessive and inappropriate use of antibiotics, leading to the emergence of increasingly resistant bacteria, has become a severe problem worldwide. Against this background, the individual health care practitioner often faces the dilemma of how to identify patients who need—and particularly those who do not need—antibiotic therapy.

Imaging and/or analyzing cells and non-cell analytes in parallel can be a useful tool in determining if a subject has a condition (e.g., a viral or bacterial infection). In some embodiments, cells and non-cell analytes can be imaged and/or analyzed simultaneously (e.g., an amount of cells and non-cell analytes can be determined using a single image or field of view). In some embodiments, cells and non-cell analytes can be imaged and/or analyzed in series (e.g., an amount of cells can be determined using a first image or first field of view, and an amount of non-cell analytes can be determined using a second image or second field of view). In some embodiments, a single image or field of view can be used to determine one or more amounts corresponding to a cell and/or a non-cell analyte. In some embodiments, two or more images or fields of view can be used to determine one or more amounts corresponding to a cell and/or a non-cell analyte.

Generally, an amount of cells or non-cell analytes can correspond to number of cell or non-cell analytes within a sample. However, in some embodiments, an amount of cells or non-cell analytes can correspond to a concentration of cells or non-cell analytes within a sample. In some embodiments, an amount of cells or non-cell analytes can correspond to a fraction of cells or non-cell analytes (e.g., a fraction of cells having a given size or shape).

An analyte can generally be any molecule associated with the presence or absence of a condition. Non-limiting examples of analytes include alpha-fetoprotein, prostate-specific antigen, cardiac troponins, c-reactive protein (CRP), or human chorionic gonadotropin, a carcinogen, a marker for influenza virus, HPV, HBV, HCV, EBV, HIV, HSV, FeLV, FIV, Hanta virus, HTLV I, HTLV II or CMV infection, a marker for bacterial infection, a marker for fungal infection, or a marker for parasitic infection. A cell can be any cell of the body. In some embodiments, a cell can refer to a cell of the immune system. Non-limiting examples of cells of the immune system include white blood cells, leukocytes, granulocytes, a granulocytes, myeloid cells, lymphoid cells, neutrophils, eosinophils, basophils, lymphocytes, T-cells, B-cells, natural killer cells, and monocytes.

Embodiments of the present disclosure can comprise detecting or determining (i) an amount of cells and (ii) an amount of non-cell analytes in a sample. In some embodiments, methods can further comprise determining if, based on the amount of cells and the amount of non-cell analytes in a sample, a subject has a condition. In some embodiments, the condition will be a condition which causes changes in the amount of the cells or non-cell analytes in the sample. In some embodiments of the present disclosure, analyzing cells and non-cell analytes in a sample can be used to determine if the sample being analyzed was obtained from a subject having an immune system disorder. As used herein, "an immune system disease or disorder" can refer to a pathological condition caused by a defect in the immune system. If a person is born with a severely defective immune system, death from infection by a virus, bacterium, fungus or parasite can occur. In severe combined immunodeficiency, lack of an enzyme can mean that toxic waste builds up inside immune system cells, killing them and thus devastating the immune system. A lack of immune system cells is also the basis for DiGeorge syndrome: improper development of the thymus gland can mean that T cell production is diminished. Most other immune disorders result from either an excessive immune response or an 'autoimmune attack'. For example, asthma, familial Mediterranean fever and Crohn disease (inflammatory bowel disease) all result from an over-reaction of the immune system, while autoimmune polyglandular syndrome and some facets of diabetes are due to the immune system attacking 'self' cells and molecules. A key part of the immune system's role is to differentiate between invaders and the body's own cells—when it fails to make this distinction, a reaction against 'self' cells and molecules causes autoimmune disease.

In some embodiments of the present disclosure, analyzing cells and non-cell analytes in a sample can be used to determine if the sample being analyzed was obtained from a subject having a metabolic disease. As used herein, "a metabolic disease or disorder" can refer to a pathological condition caused by errors in metabolic processes. Metabolism can be the means by which the body derives energy and synthesizes the other molecules it needs from the fats, carbohydrates and proteins from food, by enzymatic reactions helped by minerals and vitamins. There is a significant level of tolerance of errors in the system: often, a mutation in one enzyme does not mean that the individual can suffer from a disease. A number of different enzymes may compete to modify the same molecule, and there may be more than one way to achieve the same end result for a variety of metabolic intermediates. Disease can occur if a critical enzyme is disabled, or if a control mechanism for a metabolic pathway is affected.

In some embodiments of the present disclosure, analyzing cells and non-cell analytes in a sample can be used to determine if the sample being analyzed was obtained from a subject having a muscle or bone disease. As used herein, "a muscle and bone disease or disorder" can refer to a pathological condition caused by defects in genes important for the formation and function of muscles, and connective tissues. Connective tissue is used herein as a broad term that includes bones, cartilage and tendons. For example, defects in fibrillin—a connective tissue protein that is important in making the tissue strong yet flexible—cause Marfan syndrome, while diastrophic dysplasia is caused by a defect in a sulfate transporter found in cartilage.

In some embodiments of the present disclosure, analyzing cells and non-cell analytes in a sample can be used to determine if the sample being analyzed was obtained from a subject having a disease of the nervous system. A nervous system disease can refer to a pathological condition caused by defects in the nervous system including the central nervous system, i.e., brain, and the peripheral nervous system. The brain and nervous system form an intricate network of electrical signals that are responsible for coordinating muscles, the senses, speech, memories, thought and emotion. Several diseases that directly affect the nervous system have a genetic component: some are due to a mutation in a single gene, others are proving to have a more complex mode of inheritance.

In some embodiments of the present disclosure, analyzing cells (e.g., white blood cells) and non-cell analytes (e.g., a carcinogen) in a sample can be used to determine if the sample being analyzed was obtained from a subject having cancer. Subjects can have any type of cancer. Examples of cancer can include, but are not limited to, adrenal cancer, anal cancer, basal cell carcinoma, bile duct cancer, bladder cancer, cancer of the blood, bone cancer, a brain tumor, breast cancer, bronchus cancer, cancer of the cardiovascular system, cervical cancer, colon cancer, colorectal cancer, cancer of the digestive system, cancer of the endocrine system, endometrial cancer, esophageal cancer, eye cancer, gallbladder cancer, a gastrointestinal tumor, kidney cancer, hematopoietic malignancy, laryngeal cancer, leukemia, liver cancer, lung cancer, lymphoma, melanoma, mesothelioma, cancer of the muscular system, Myelodysplastic Syndrome (MDS), myeloma, nasal cavity cancer, nasopharyngeal cancer, cancer of the nervous system, cancer of the lymphatic system, oral cancer, oropharyngeal cancer, osteosarcoma, ovarian cancer, pancreatic cancer, penile cancer, pituitary tumors, prostate cancer, rectal cancer, renal pelvis cancer, cancer of the reproductive system, cancer of the respiratory system, sarcoma, salivary gland cancer, skeletal system cancer, skin cancer, small intestine cancer, stomach cancer, testicular cancer, throat cancer, thymus cancer, thyroid cancer, a tumor, cancer of the urinary system, uterine cancer, vaginal cancer, or vulvar cancer. The term 'lymphoma' may refer to any type of lymphoma including B-cell lymphoma (e.g., diffuse large B-cell lymphoma, follicular lymphoma, small lymphocytic lymphoma, mantle cell lymphoma, marginal zone B-cell lymphoma, Burkitt lymphoma, lymphoplasmacytic lymphoma, hairy cell leukemia, or primary central nervous system lymphoma) or a T-cell lymphoma (e.g., precursor T-lymphoblastic lymphoma, or peripheral T-cell lymphoma). The term 'leukemia' may refer to any type of leukemia including acute leukemia or chronic leukemia. Types of leukemia include acute myeloid leukemia, chronic myeloid leukemia, acute lymphocytic leukemia, acute undifferentiated leukemia, or chronic lymphocytic leukemia. In some cases, the cancer patient does not have a particular type of cancer. For example, in some instances, the patient may have a cancer that is not breast cancer.

Capture agents with conjugated reporter molecules can be used to detect cells and/or non-cell analytes. For example, acridine orange can be used to stain white blood cells in a sample. Non-limiting examples of reporter molecules include include cyanine 5 (Cy5), histidine (His), V5, FLAG, influenza hemagglutinin (HA), Myc, VSV-G, and thioredoxin (Trx), glutathione-S-transferase (GST), horseradish peroxidase (HRP), chloramphenicol acetyltransferase (CAT) beta-galactosidase, beta-glucuronidase, luciferase, green fluorescent protein (GFP), HcRed, DsRed, cyan fluorescent protein (CFP), yellow fluorescent protein (YFP), and autofluorescent proteins including blue fluorescent protein (BFP). For example, an anti-CRP antibody (e.g., a capture agent) conjugated with GFP can be used to determine the presence or amount of CRP in a sample.

Staining reagents (e.g., dyes) can be used in order to make cells (e.g., nucleated cells) detectable. For example, a sample can be stained with acridine orange (AO), a dye capable of staining the nucleus of live cells as well as several constituents of the cytoplasm. Acridine orange has its absorption peak at 490 nm, and emits at 520 nm when bound to DNA. Other fluorescent dyes, such as Hoechst 33258, and Hoechst 33342 can be used. In general, any fluorescent dye that non-specifically stains cells, cytoplasm, cellular nucleic material, or the nucleus itself can be used. These dyes are referred to herein as "non-specific fluorescent dyes." In some embodiments, a capture agent or a staining reagent can be coated onto one or more surfaces of the first plate and/or the second plate. It is contemplated that, coating a capture agent or a staining reagent onto one or more surfaces of the first plate or the second plate can be useful in reducing the number of steps performed by the user in order to analyze a sample. For example, if the first plate is coated with a cell staining reagent, the user would simply need to deposit a sample onto or into the QMAX card (e.g., within the sample contact area). Upon contact the cell staining reagent, cells within the sample can be automatically (e.g., without user intervention) stained. A reduction in the number steps performed by the user can reduce error (e.g., human error), increase accuracy in data analysis, and reduce the amount of time needed to analyze a sample. In some embodiments, a capture agent can be coated on one or more surfaces of a first plate, and a staining reagent can be coated on one or more surfaces of a second plate. In another embodiment, a capture agent and a staining reagent can be coated on one or more surfaces of either the first plate or the second plate. In yet another embodiment, a capture agent and a staining reagent can be coated on one or more surfaces of both of the first plate and the second plate.

In one example, CRP (C-reactive protein) is a protein normally present in very low concentrations (<1 μg/mL) in the blood of healthy people. In bacterial infections, CRP concentrations markedly increase (>10 μg/mL), whereas viral infections usually only induce very modest CRP elevation or none at all. Thus, CRP can be used as a biomarker to clinically distinguish bacterial infection from viral infection. Other biomarkers in this category include white blood cell (WBC) counting, lymphocytes (LYM) counting and PCT (Procalcitonin) etc.

Analyzing an amount of cells and non-cell analytes can include determining a number of cells (e.g., white blood cells), determining a number of non-cell analytes (e.g., CRP), and comparing those values against one or more reference value to determine if a subject from whom the analyzed sample was obtained has a condition. In some embodiments, analyzing an amount of cells and non-cell analytes can include determining a ratio of the amount of cells to the amount of non-cell analytes, and comparing the ratio to a reference value to determine if a subject from whom the analyzed sample was obtained has a condition. In some embodiments, measurements (e.g., an amount of cells or an amount of non-cell analytes) obtained from a healthy subject or a subject with a condition may be stored on a database, and used to determine a reference value against which a future measurement is compared.

Example-1

Fast, Homogenous Staining of Cells and Non-Cell Analytes in Parallel

Here we describe a One-Step combo blood test that report CRP, WBC and LYM level or counts in 60 sec. The combination of three tests (CRP, WBC and LYM) result in very high sensitivity and specificity to distinguish bacterial infection from viral infection and thus is very valuable for antibiotic administration.

Figure 1B:
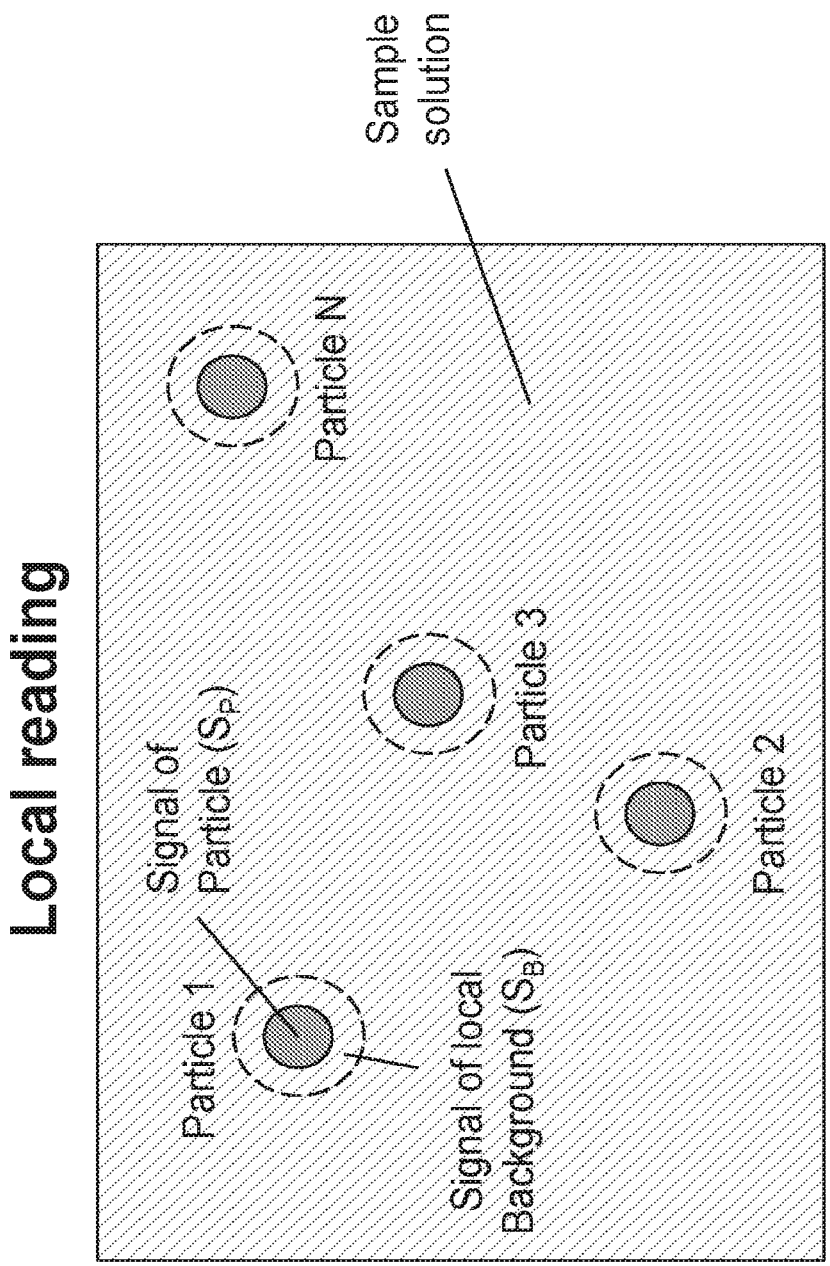
Figure 2:
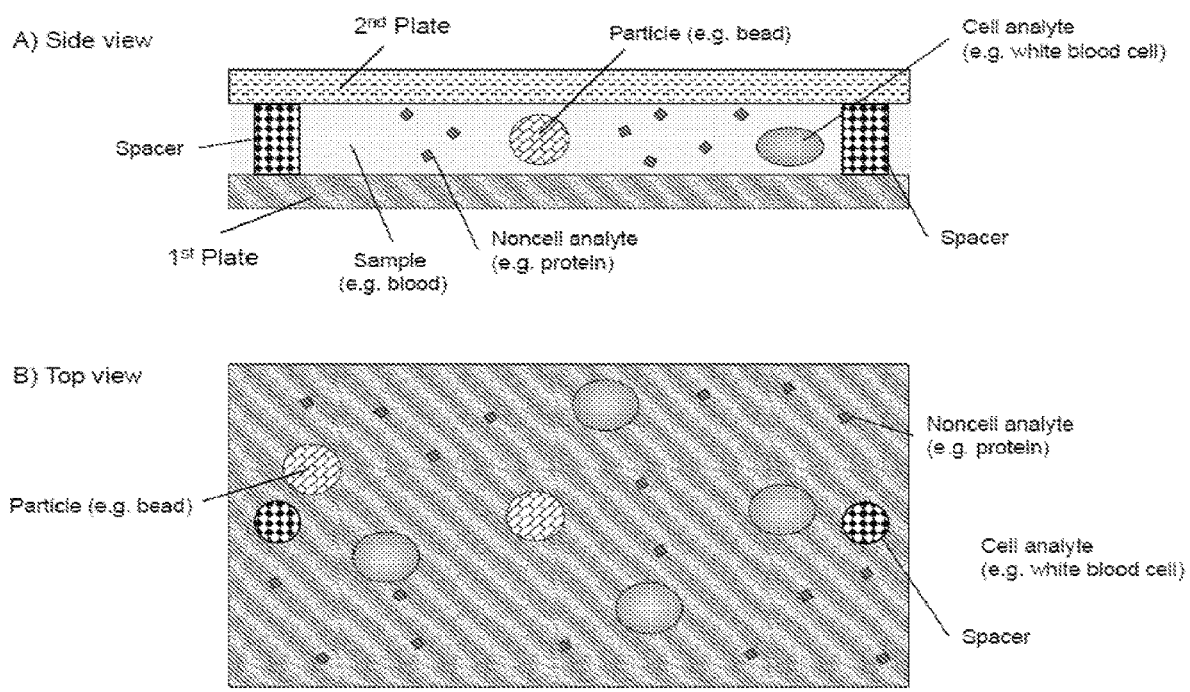
FIG. 2 provides schematic illustrations showing some of the exemplary processes of the present invention.

In the local reading approach, as shown in FIG. 1, one or more than one particles will be measured for the following two measurements: (a) the signal from the particle region (SP). It can be from the whole particle region or a designated area of the particle region; and (b) the signal of area around the particle (local background SB). It can be from the whole area around the particle or a designated area. The definition of "around" can be a distance of 0.01D, 0.1D, 0.2D, 0.5D, 1D, 2D, 5D, 10D, 50D or a range between any two of the values to the outer surface of the particle, in which "D" is the average diameter of the particle. The true Signal of Assay (SA) for each particle can be determined as SA=SP−SB. The assay signal from each CROF (SCROF) can be the average of multiple particles. It can be all particles on a whole CROF or particles in a designated region of a CROF (e.g., SCROF=Average (SA1, SA2, SA3 . . . SAn))

Figure 3:
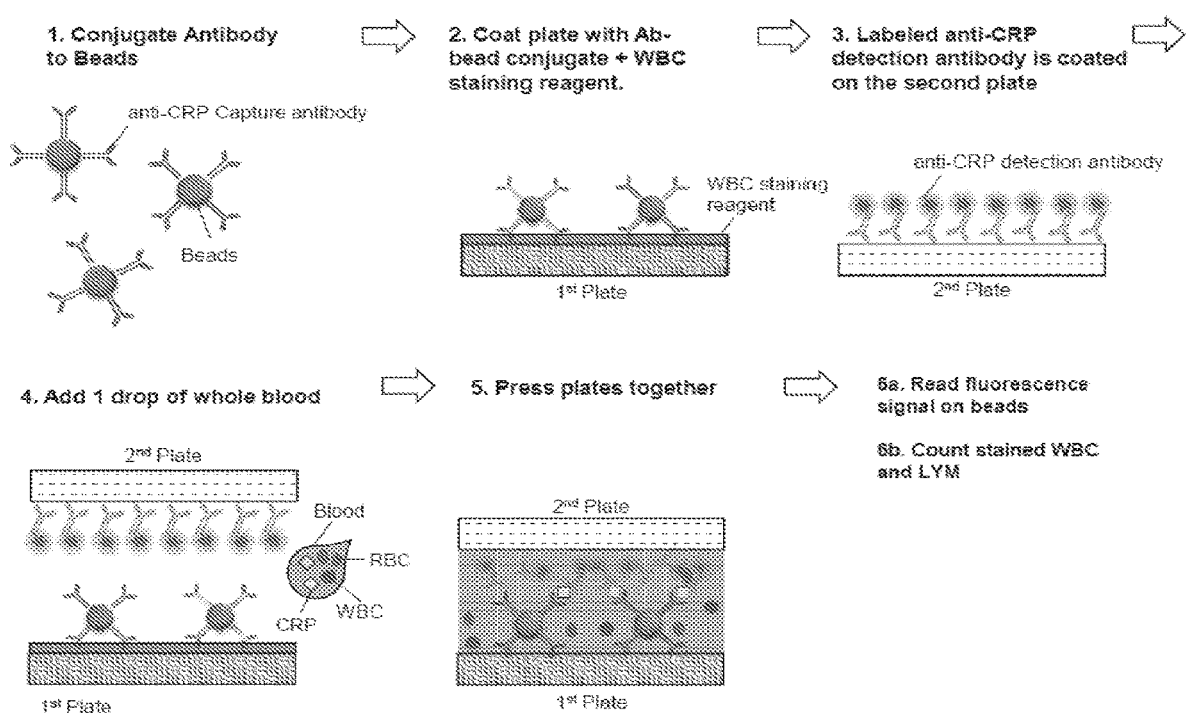
FIG. 3 provides schematic illustrations showing some of the exemplary processes of the present invention.

In this experiment, the device for the immunoassay comprises a first plate and a second plate. As shown in FIG. 3, Panel 1, the capture antibody is first conjugated to the magnetic beads. Next, as shown in Panel 2, one x-plate is coated with the antibody-conjugated beads mixed with the WBC staining reagent. As shown in Panel 3, the second x-plate is then coated with the labeled anti-CRP detection antibody. In Panel 4, after preparation of the individual x-plates, the Q-card is ready to receive a drop of blood. As shown in Panel 5, after adding a drop of whole blood, the x-plates are quickly pressed together to dissolve the reagents and initiate the assay. Subsequently, as shown in Panel 6, after 30 seconds has passed, the assay can be analyzed for WBC counts and CRP concentrations.

The experiment was conducted using the following materials:
Anti-human CRP rabbit polyclonal antibody (Abcam)
PureProteome NHS FlexiBind Magnetic Beads (Millipore)
Human CRP analyte (Fitzgerald)
4% BSA
PBS (Phosphate buffer saline solution)
PBS-Tween 20 (PBST)
X-plate with 10 um spacers
Whole blood
Acridine orange The experiment was conducted according to the following procedures:
1. Conjugation of the anti-CRP capture antibody to the beads. NHS activated beads (Millipore, 10 μm in diameter) are conjugated to an anti-CRP mouse monoclonal capture antibody (Fitzgerald) according to manufacturer's protocol.
2. Blocking of beads. The antibody conjugated beads are blocked overnight using 4% BSA in PBS at 4° C. The following day, the beads are washed by PBST 6 times prior to use.
3. Coating of first plate. 1 μL of antibody-conjugated beads from Step 2 (beads concentration 107-108/mL) with or without 25 μg/mL acridine orange (AO, WBC staining reagent) are dropped onto a Q-card and air dried at room temperature.
4. Homogenous BEST assay. 1 μL of fresh whole blood and 1 μL of Cy5-labeled anti-CRP mouse monoclonal detection antibody (Fitzgerald) are mixed together then dropped on top the same area of the Q-card that is occupied by the dried, antibody-conjugated beads. The mix is immediately covered by the second x-plate containing 10 μm pillars. The assay is incubated for 30 seconds before imaging occurs.
5. Imaging. Without washing, two fluorescent images are taken using the iPhone 6s at different wavelengths to observe either the staining signal of the WBCs or the signal from the anti-CRP detection antibody.

Figure 4:
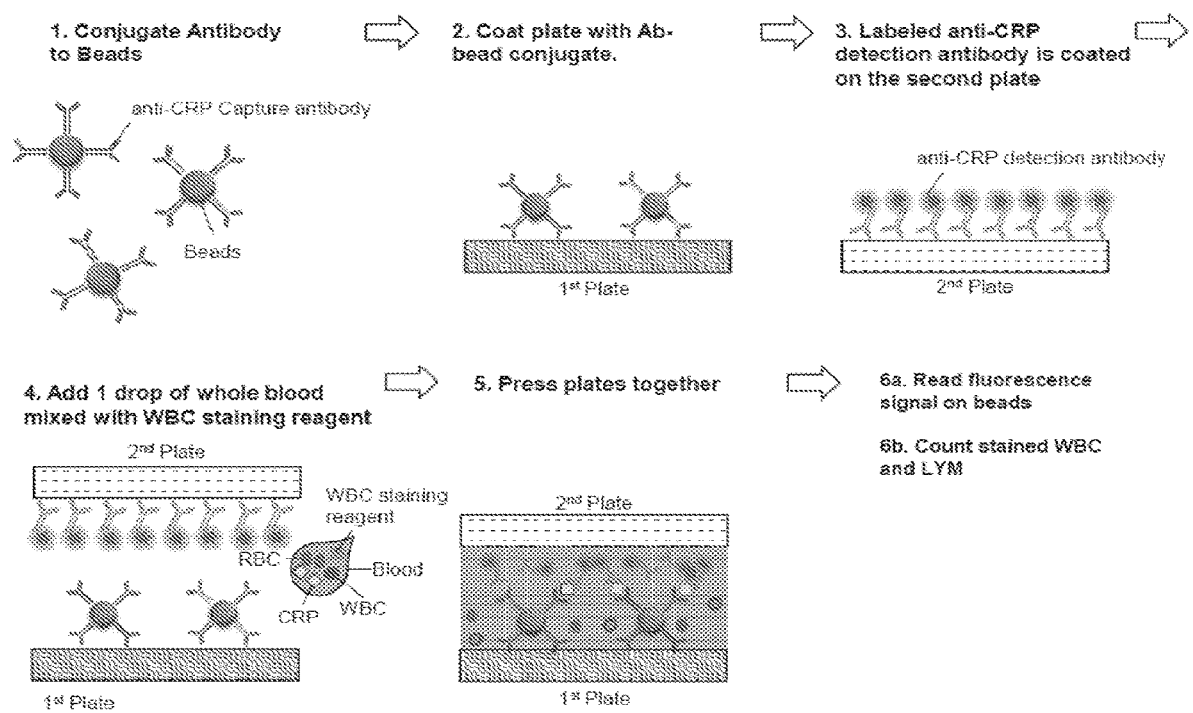
FIG. 4 provides schematic illustrations showing some of the exemplary processes of the present invention.

In another experiment, the device for the immunoassay comprises a first plate and a second plate. As shown in FIG. 4, Panel 1, the capture antibody is first conjugated to the magnetic beads. Next, as shown in Panel 2, one x-plate is coated with the antibody-conjugated beads. As shown in Panel 3, the second x-plate is then coated with the labeled anti-CRP detection antibody. In Panel 4, after preparation of the individual x-plates, the Q-card is ready to receive a drop of blood mixed with the WBC staining reagent. As shown in Panel 5, after adding a drop of whole blood mixed with the WBC staining reagent, the x-plates are quickly pressed together to dissolve the reagents and initiate the assay. Subsequently, as shown in Panel 6, after 30 seconds has passed, the assay can be analyzed for WBC counts and CRP concentrations.

QMAX System

A) QMAX Card

Details of the QMAX card are described in detail in a variety of publications including International Application No. PCT/US2016/046437 (Essenlix Docket No. ESSN-028WO), which is hereby incorporated by reference herein for all purposes.

I. Plates

In present invention, generally, the plates of CROF are made of any material that (i) is capable of being used to regulate, together with the spacers, the thickness of a portion or entire volume of the sample, and (ii) has no significant adverse effects to a sample, an assay, or a goal that the plates intend to accomplish. However, in certain embodiments, particular materials (hence their properties) are used for the plate to achieve certain objectives.

In certain embodiments, the two plates have the same or different parameters for each of the following parameters: plate material, plate thickness, plate shape, plate area, plate flexibility, plate surface property, and plate optical transparency.

(i) Plate Materials. The plates are made a single material, composite materials, multiple materials, multilayer of materials, alloys, or a combination thereof. Each of the materials for the plate is an inorganic material, am organic material, or a mix, wherein examples of the materials are given in paragraphs of Mat-1 and Mat-2.

Mat-1: The inorganic materials for the plates include, not limited to, glass, quartz, oxides, silicon-dioxide, silicon-nitride, hafnium oxide (HfO), aluminum oxide (AlO), semiconductors: (silicon, GaAs, GaN, etc.), metals (e.g. gold, silver, copper, aluminum, Ti, Ni, etc.), ceramics, or any combinations of thereof.

Mat-2: The organic materials for the spacers include, not limited to, polymers (e.g. plastics) or amorphous organic materials. The polymer materials for the spacers include, not limited to, acrylate polymers, vinyl polymers, olefin polymers, cellulosic polymers, noncellulosic polymers, polyester polymers, Nylon, cyclic olefin copolymer (COC), poly (methyl methacrylate) (PMMA), polycarbonate (PC), cyclic olefin polymer (COP), liquid crystalline polymer (LCP), polyimide (PA), polyethylene (PE), polyimide (PI), polypropylene (PP), poly(phenylene ether) (PPE), polystyrene (PS), polyoxymethylene (POM), polyether ether ketone (PEEK), polyether sulfone (PES), poly(ethylene phthalate) (PET), polytetrafluoroethylene (PTFE), polyvinyl chloride (PVC), polyvinylidene fluoride (PVDF), polybutylene terephthalate (PBT), fluorinated ethylene propylene (FEP), perfluoroalkoxyalkane (PFA), polydimethylsiloxane (PDMS), rubbers, or any combinations of thereof.

In certain embodiments, the plates are each independently made of at least one of glass, plastic, ceramic, and metal. In certain embodiments, each plate independently includes at least one of glass, plastic, ceramic, and metal.

In certain embodiments, one plate is different from the other plate in lateral area, thickness, shape, materials, or surface treatment. In certain embodiments, one plate is the same as the other plate in lateral area, thickness, shape, materials, or surface treatment.

The materials for the plates are rigid, flexible or any flexibility between the two. The rigid (i.e. stiff) or flexibility is relative to a give pressing forces used in bringing the plates into the closed configuration.

In certain embodiments, a selection of rigid or flexible plate are determined from the requirements of controlling a uniformity of the sample thickness at the closed configuration.

In certain embodiments, at least one of the two plates are transparent (to a light). In certain embodiments at least a part or several parts of one plate or both plates are transparent. In certain embodiments, the plates are non-transparent.

(ii) Plate Thickness. In certain embodiments, the average thicknesses for at least one of the pates are 2 nm or less, 10 nm or less, 100 nm or less, 500 nm or less, 1000 nm or less, 2 um (micron) or less, 5 um or less, 10 um or less, 20 um or less, 50 um or less, 100 um or less, 150 um or less, 200 um or less, 300 um or less, 500 um or less, 800 um or less, 1 mm (millimeter) or less, 2 mm or less, 3 mm or less, or a range between any two of the values.

In certain embodiments, the average thicknesses for at least one of the plates are at most 3 mm (millimeter), at most 5 mm, at most 10 mm, at most 20 mm, at most 50 mm, at most 100 mm, at most 500 mm, or a range between any two of the values.

In certain embodiments, the thickness of a plate is not uniform across the plate. Using a different plate thickness at different location can be used to control the plate bending, folding, sample thickness regulation, and others.

(iii) Plate Shape and Area. Generally, the plates can have any shapes, as long as the shape allows a compress open flow of the sample and the regulation of the sample thickness. However, in certain embodiments, a particular shape can be advantageous. The shape of the plate can be round, elliptical, rectangles, triangles, polygons, ring-shaped, or any superpositions of these shapes.

In certain embodiments, the two plates can have the same size or shape, or different. The area of the plates depend on the application. The area of the plate is at most 1 mm2 (millimeter square), at most 10 mm2, at most 100 mm2, at most 1 cm2 (centimeter square), at most 5 cm2, at most 10 cm2, at most 100 cm2, at most 500 cm2, at most 1000 cm2, at most 5000 cm2, at most 10,000 cm2, or over 10,000 cm2, or any arrange between any of the two values. The shape of the plate can be rectangle, square, round, or others.

In certain embodiments, at least one of the plates is in the form of a belt (or strip) that has a width, thickness, and length. The width is at most 0.1 cm (centimeter), at most 0.5 cm, at most 1 cm, at most 5 cm, at most 10 cm, at most 50 cm, at most 100 cm, at most 500 cm, at most 1000 cm, or a range between any two of the values. The length can be as long it needed. The belt can be rolled into a roll.

(iv) Plate Surface Flatness. In many embodiments, an inner surface of the plates are flat or significantly flat, planar. In certain embodiments, the two inner surfaces are, at the closed configuration, parallel with each other. Flat inner surfaces facilitates a quantification and/or controlling of the sample thickness by simply using the predetermined spacer height at the closed configuration. For non-flat inner surfaces of the plate, one need to know not only the spacer height, but also the exact the topology of the inner surface to quantify and/or control the sample thickness at the closed configuration. To know the surface topology needs additional measurements and/or corrections, which can be complex, time consuming, and costly.

A flatness of the plate surface is relative to the final sample thickness (the final thickness is the thickness at the closed configuration), and is often characterized by the term of "relative surface flatness" is the ratio of the plate surface flatness variation to the final sample thickness.

In certain embodiments, the relative surface is less than 0.01%, 0.1%, less than 0.5%, less than 1%, less than 2%, less than 5%, less than 10%, less than 20%, less than 30%, less than 50%, less than 70%, less than 80%, less than 100%, or a range between any two of these values.

(v) Plate Surface Parallelness. In certain embodiments, the two surfaces of the plate is significantly parallel with each other. In certain embodiments, the two surfaces of the plate is not parallel with each other.

(vi) Plate Flexibility. In certain embodiments, a plate is flexible under the compressing of a CROF process. In certain embodiments, both plates are flexible under the compressing of a CROF process. In certain embodiments, a plate is rigid and another plate is flexible under the compressing of a CROF process. In certain embodiments, both plates are rigid. In certain embodiments, both plate are flexible but have different flexibility.

(vii) Plate Optical Transparency. In certain embodiments, a plate is optical transparent. In certain embodiments, both plates are optical transparent. In certain embodiments, a plate is optical transparent and another plate is opaque. In certain embodiments, both plates are opaque. In certain embodiments, both plate are optical transparent but have different optical transparency. The optical transparency of a plate can refer to a part or the entire area of the plate.

(viii) Surface Wetting Properties. In certain embodiments, a plate has an inner surface that wets (i.e. contact angle is less 90 degree) the sample, the transfer liquid, or both. In certain embodiments, both plates have an inner surface that wets the sample, the transfer liquid, or both; either with the same or different wettability. In certain embodiments, a plate has an inner surface that wets the sample, the transfer liquid, or both; and another plate has an inner surface that does not wet (i.e. the contact angle equal to or larger than 90 degree). The wetting of a plate inner surface can refer to a part or the entire area of the plate.

In certain embodiments, the inner surface of the plate has other nano or microstructures to control a lateral flow of a sample during a CROF. The nano or microstructures include, but not limited to, channels, pumps, and others. Nano and microstructures are also used to control the wetting properties of an inner surface.

II. Spacers (i) Spacers' Function. In present invention, the spacers are configured to have one or any combinations of the following functions and properties: the spacers are configured to (1) control, together with the plates, the thickness of the sample or a relevant volume of the sample (Preferably, the thickness control is precise, or uniform or both, over a relevant area); (2) allow the sample to have a compressed regulated open flow (CROF) on plate surface; (3) not take significant surface area (volume) in a given sample area (volume); (4) reduce or increase the effect of sedimentation of particles or analytes in the sample; (5) change and/or control the wetting propertied of the inner surface of the plates; (6) identify a location of the plate, a scale of size, and/or the information related to a plate, or (7) do any combination of the above.

(ii) Spacer Architectures and Shapes. To achieve desired sample thickness reduction and control, in certain embodiments, the spacers are fixed its respective plate. In general, the spacer can have any shape, as long as the spacers are capable of regulating the sample thickness during a CROF process, but certain shapes are preferred to achieve certain functions, such as better uniformity, less overshoot in pressing, etc.

The spacer(s) is a single spacer or a plurality of spacers. (e.g. an array). Certain embodiments of a plurality of spacers is an array of spacers (e.g. pillars), where the inter-spacer distance is periodic or aperiodic, or is periodic or aperiodic in certain areas of the plates, or has different distances in different areas of the plates.

There are two kinds of the spacers: open-spacers and enclosed-spacers. The open-spacer is the spacer that allows a sample to flow through the spacer (i.e. the sample flows around and pass the spacer. For example, a post as the spacer.), and the enclosed spacer is the spacer that stop the sample flow (i.e. the sample cannot flow beyond the spacer. For example, a ring shape spacer and the sample is inside the ring.). Both types of spacers use their height to regular the final sample thickness at a closed configuration.

In certain embodiments, the spacers are open-spacers only. In certain embodiments, the spacers are enclosed-spacers only. In certain embodiments, the spacers are a combination of open-spacers and enclosed-spacers.

The term "pillar spacer" means that the spacer has a pillar shape and the pillar shape can refer to an object that has height and a lateral shape that allow a sample to flow around it during a compressed open flow.

In certain embodiments, the lateral shapes of the pillar spacers are the shape selected from the groups of (i) round, elliptical, rectangles, triangles, polygons, ring-shaped, star-shaped, letter-shaped (e.g. L-shaped, C-shaped, the letters from A to Z), number shaped (e.g. the shapes like 0 1, 2, 3, 4, . . . to 9); (ii) the shapes in group (i) with at least one rounded corners; (iii) the shape from group (i) with zig-zag or rough edges; and (iv) any superposition of (i), (ii) and (iii). For multiple spacers, different spacers can have different lateral shape and size and different distance from the neighboring spacers.

In certain embodiments, the spacers can be and/or can include posts, columns, beads, spheres, and/or other suitable geometries. The lateral shape and dimension (i.e., transverse to the respective plate surface) of the spacers can be anything, except, in certain embodiments, the following restrictions: (i) the spacer geometry will not cause a significant error in measuring the sample thickness and volume; or (ii) the spacer geometry would not prevent the out-flowing of the sample between the plates (i.e. it is not in enclosed form). But in certain embodiments, they require some spacers to be closed spacers to restrict the sample flow.

In certain embodiments, the shapes of the spacers have rounded corners. For example, a rectangle shaped spacer has one, several or all corners rounded (like a circle rather 90 degree angle). A round corner often make a fabrication of the spacer easier, and in some cases less damage to a biological material.

The sidewall of the pillars can be straight, curved, sloped, or different shaped in different section of the sidewall. In certain embodiments, the spacers are pillars of various lateral shapes, sidewalls, and pillar-height to pillar lateral area ratio. In a preferred embodiment, the spacers have shapes of pillars for allowing open flow.

(iii) Spacers' Materials. In the present invention, the spacers are generally made of any material that is capable of being used to regulate, together with the two plates, the thickness of a relevant volume of the sample. In certain embodiments, the materials for the spacers are different from that for the plates. In certain embodiments, the materials for the spaces are at least the same as a part of the materials for at least one plate.

The spacers are made a single material, composite materials, multiple materials, multilayer of materials, alloys, or a combination thereof. Each of the materials for the spacers is an inorganic material, am organic material, or a mix, wherein examples of the materials are given in paragraphs of Mat-1 and Mat-2. In a preferred embodiment, the spacers are made in the same material as a plate used in CROF.

(iv) Spacers' Mechanical Strength and Flexibility. In certain embodiments, the mechanical strength of the spacers are strong enough, so that during the compression and at the closed configuration of the plates, the height of the spacers is the same or significantly same as that when the plates are in an open configuration. In certain embodiments, the differences of the spacers between the open configuration and the closed configuration can be characterized and predetermined.

The material for the spacers is rigid, flexible or any flexibility between the two. The rigid is relative to a give pressing forces used in bringing the plates into the closed configuration: if the space does not deform greater than 1% in its height under the pressing force, the spacer material is regarded as rigid, otherwise a flexible. When a spacer is made of material flexible, the final sample thickness at a closed configuration still can be predetermined from the pressing force and the mechanical property of the spacer.

(v) Spacers Inside Sample. To achieve desired sample thickness reduction and control, particularly to achieve a good sample thickness uniformity, in certain embodiments, the spacers are placed inside the sample, or the relevant volume of the sample. In certain embodiments, there are one or more spacers inside the sample or the relevant volume of the sample, with a proper inter spacer distance. In certain embodiments, at least one of the spacers is inside the sample, at least two of the spacers inside the sample or the relevant volume of the sample, or at least of "n" spacers inside the sample or the relevant volume of the sample, where "n" can be determined by a sample thickness uniformity or a required sample flow property during a CROF.

(vi) Spacer Height. In certain embodiments, all spacers have the same pre-determined height. In certain embodiments, spacers have different pre-determined height. In certain embodiments, spacers can be divided into groups or regions, wherein each group or region has its own spacer height. And in certain embodiments, the predetermined height of the spacers is an average height of the spacers. In certain embodiments, the spacers have approximately the same height. In certain embodiments, a percentage of number of the spacers have the same height.

The height of the spacers is selected by a desired regulated final sample thickness and the residue sample thickness. The spacer height (the predetermined spacer height) and/or sample thickness is 3 nm or less, 10 nm or less, 50 nm or less, 100 nm or less, 200 nm or less, 500 nm or less, 800 nm or less, 1000 nm or less, 1 um or less, 2 um or less, 3 um or less, 5 um or less, 10 um or less, 20 um or less, 30 um or less, 50 um or less, 100 um or less, 150 um or less, 200 um or less, 300 um or less, 500 um or less, 800 um or less, 1 mm or less, 2 mm or less, 4 mm or less, or a range between any two of the values.

The spacer height and/or sample thickness is between 1 nm to 100 nm in one preferred embodiment, 100 nm to 500 nm in another preferred embodiment, 500 nm to 1000 nm in a separate preferred embodiment, 1 um (i.e. 1000 nm) to 2 um in another preferred embodiment, 2 um to 3 um in a separate preferred embodiment, 3 um to 5 um in another preferred embodiment, 5 um to 10 um in a separate preferred embodiment, and 10 um to 50 um in another preferred embodiment, 50 um to 100 um in a separate preferred embodiment.

In certain embodiments, the spacer height and/or sample thickness (i) equal to or slightly larger than the minimum dimension of an analyte, or (ii) equal to or slightly larger than the maximum dimension of an analyte. The "slightly larger" means that it is about 1% to 5% larger and any number between the two values.

In certain embodiments, the spacer height and/or sample thickness is larger than the minimum dimension of an analyte (e.g. an analyte has an anisotropic shape), but less than the maximum dimension of the analyte.

For example, the red blood cell has a disk shape with a minim dimension of 2 um (disk thickness) and a maximum dimension of 11 um (a disk diameter). In an embodiment of the present invention, the spacers is selected to make the inner surface spacing of the plates in a relevant area to be 2 um (equal to the minimum dimension) in one embodiment, 2.2 um in another embodiment, or 3 (50% larger than the minimum dimension) in other embodiment, but less than the maximum dimension of the red blood cell. Such embodiment has certain advantages in blood cell counting. In one embodiment, for red blood cell counting, by making the inner surface spacing at 2 or 3 um and any number between the two values, a undiluted whole blood sample is confined in the spacing, on average, each red blood cell (RBC) does not overlap with others, allowing an accurate counting of the red blood cells visually. (Too many overlaps between the RBC's can cause serious errors in counting).

In the present invention, in certain embodiments, it uses the plates and the spacers to regulate not only a thickness of a sample, but also the orientation and/or surface density of the analytes/entity in the sample when the plates are at the closed configuration. When the plates are at a closed configuration, a thinner thickness of the sample gives a less the analytes/entity per surface area (i.e. less surface concentration).

(vii) Spacer Lateral Dimension. For an open-spacer, the lateral dimensions can be characterized by its lateral dimension (sometime being called width) in the x and y—two orthogonal directions. The lateral dimension of a spacer in each direction is the same or different. In certain embodiments, the lateral dimension for each direction (x or y) is . . . .

In certain embodiments, the ratio of the lateral dimensions of x to y direction is 1, 1.5, 2, 5, 10, 100, 500, 1000, 10,000, or a range between any two of the value. In certain embodiments, a different ratio is used to regulate the sample flow direction; the larger the ratio, the flow is along one direction (larger size direction).

In certain embodiments, the different lateral dimensions of the spacers in x and y direction are used as (a) using the spacers as scale-markers to indicate the orientation of the plates, (b) using the spacers to create more sample flow in a preferred direction, or both.

In a preferred embodiment, the period, width, and height.

In certain embodiments, all spacers have the same shape and dimensions. In certain embodiments, each of the spacers have different lateral dimensions.

For enclosed-spacers, in certain embodiments, the inner lateral shape and size are selected based on the total volume of a sample to be enclosed by the enclosed spacer(s), wherein the volume size has been described in the present disclosure; and in certain embodiments, the outer lateral shape and size are selected based on the needed strength to support the pressure of the liquid against the spacer and the compress pressure that presses the plates.

(viii) Aspect Ratio of Height to the Average Lateral Dimension of Pillar Spacer. In certain embodiments, the aspect ratio of the height to the average lateral dimension of the pillar spacer is 100,000, 10,000, 1,000, 100, 10, 1, 0.1, 0.01, 0.001, 0.0001, 0, 00001, or a range between any two of the values.

(ix) Spacer Height Precisions. The spacer height should be controlled precisely. The relative precision of the spacer (i.e. the ratio of the deviation to the desired spacer height) is 0.001% or less, 0.01% or less, 0.1% or less; 0.5% or less, 1% or less, 2% or less, 5% or less, 8% or less, 10% or less, 15% or less, 20% or less, 30% or less, 40% or less, 50% or less, 60% or less, 70% or less, 80% or less, 90% or less, 99.9% or less, or a range between any of the values.

(x) Inter-Spacer Distance. The spacers can be a single spacer or a plurality of spacers on the plate or in a relevant area of the sample. In certain embodiments, the spacers on the plates are configured and/or arranged in an array form, and the array is a periodic, non-periodic array or periodic in some locations of the plate while non-periodic in other locations.

In certain embodiments, the periodic array of the spacers has a lattice of square, rectangle, triangle, hexagon, polygon, or any combinations of thereof, where a combination means that different locations of a plate has different spacer lattices.

In certain embodiments, the inter-spacer distance of a spacer array is periodic (i.e. uniform inter-spacer distance) in at least one direction of the array. In certain embodiments, the inter-spacer distance is configured to improve the uniformity between the plate spacing at a closed configuration.

The distance between neighboring spacers (i.e. the inter-spacer distance) is 1 um or less, 5 um or less, 10 um or less, 20 um or less, 30 um or less, 40 um or less, 50 um or less, 60 um or less, 70 um or less, 80 um or less, 90 um or less, 100 um or less, 200 um or less, 300 um or less, 400 um or less, or a range between any two of the values.

In certain embodiments, the inter-spacer distance is at 400 or less, 500 or less, 1 mm or less, 2 mm or less, 3 mm or less, 5 mm or less, 7 mm or less, 10 mm or less, or any range between the values. In certain embodiments, the inter-spacer distance is a10 mm or less, 20 mm or less, 30 mm or less, 50 mm or less, 70 mm or less, 100 mm or less, or any range between the values.

The distance between neighboring spacers (i.e. the inter-spacer distance) is selected so that for a given properties of the plates and a sample, at the closed-configuration of the plates, the sample thickness variation between two neighboring spacers is, in certain embodiments, at most 0.5%, 1%, 5%, 10%, 20%, 30%, 50%, 80%, or any range between the values; or in certain embodiments, at most 80%, 100%, 200%, 400%, or a range between any two of the values.

Clearly, for maintaining a given sample thickness variation between two neighboring spacers, when a more flexible plate is used, a closer inter-spacer distance is needed.

Specify the accuracy of the inter spacer distance.

In a preferred embodiment, the spacer is a periodic square array, wherein the spacer is a pillar that has a height of 2 to 4 um, an average lateral dimension of from 5 to 20 um, and inter-spacer spacing of 1 um to 100 um.

In a preferred embodiment, the spacer is a periodic square array, wherein the spacer is a pillar that has a height of 2 to 4 um, an average lateral dimension of from 5 to 20 um, and inter-spacer spacing of 100 um to 250 um.

In a preferred embodiment, the spacer is a periodic square array, wherein the spacer is a pillar that has a height of 4 to 50 um, an average lateral dimension of from 5 to 20 um, and inter-spacer spacing of 1 um to 100 um.

In a preferred embodiment, the spacer is a periodic square array, wherein the spacer is a pillar that has a height of 4 to 50 um, an average lateral dimension of from 5 to 20 um, and inter-spacer spacing of 100 um to 250 um.

The period of spacer array is between 1 nm to 100 nm in one preferred embodiment, 100 nm to 500 nm in another preferred embodiment, 500 nm to 1000 nm in a separate preferred embodiment, 1 um (i.e. 1000 nm) to 2 um in another preferred embodiment, 2 um to 3 um in a separate preferred embodiment, 3 um to 5 um in another preferred embodiment, 5 um to 10 um in a separate preferred embodiment, and 10 um to 50 um in another preferred embodiment, 50 um to 100 um in a separate preferred embodiment, 100 um to 175 um in a separate preferred embodiment, and 175 um to 300 um in a separate preferred embodiment.

(xi) Spacer Density. The spacers are arranged on the respective plates at a surface density of greater than one per $um^2$, greater than one per 10 $um^2$, greater than one per 100 $um^2$, greater than one per 500 $um^2$, greater than one per 1000 $um^2$, greater than one per 5000 $um^2$, greater than one per 0.01 $mm^2$, greater than one per 0.1 $mm^2$, greater than one per 1 $mm^2$, greater than one per 5 $mm^2$, greater than one per 10 $mm^2$, greater than one per 100 $mm^2$, greater than one per 1000 $mm^2$, greater than one per 10000 $mm^2$, or a range between any two of the values.

(3) the spacers are configured to not take significant surface area (volume) in a given sample area (volume);

(xii) Ratio of Spacer Volume to Sample Volume. In many embodiments, the ratio of the spacer volume (i.e. the volume of the spacer) to sample volume (i.e. the volume of the sample), and/or the ratio of the volume of the spacers that are inside of the relevant volume of the sample to the relevant volume of the sample are controlled for achieving certain advantages. The advantages include, but not limited to, the uniformity of the sample thickness control, the uniformity of analytes, the sample flow properties (i.e. flow speed, flow direction, etc.).

In certain embodiments, the ratio of the spacer volume r) to sample volume, and/or the ratio of the volume of the spacers that are inside of the relevant volume of the sample to the relevant volume of the sample is less than 100%, at most 99%, at most 70%, at most 50%, at most 30%, at most 10%, at most 5%, at most 3% at most 1%, at most 0.1%, at most 0.01%, at most 0.001%, or a range between any of the values.

(xiii) Spacers Fixed to Plates. The inter spacer distance and the orientation of the spacers, which play a key role in the present invention, are preferably maintained during the process of bringing the plates from an open configuration to the closed configuration, and/or are preferably predetermined before the process from an open configuration to a closed configuration.

In certain embodiments of the present disclosure, spacers are fixed on one of the plates before bring the plates to the closed configuration. The term "a spacer is fixed with its respective plate" means that the spacer is attached to a plate and the attachment is maintained during a use of the plate. An example of "a spacer is fixed with its respective plate" is that a spacer is monolithically made of one piece of material of the plate, and the position of the spacer relative to the plate surface does not change. An example of "a spacer is not fixed with its respective plate" is that a spacer is glued to a plate by an adhesive, but during a use of the plate, the adhesive cannot hold the spacer at its original location on the plate surface (i.e. the spacer moves away from its original position on the plate surface).

In certain embodiments, at least one of the spacers are fixed to its respective plate. In certain embodiments, at two spacers are fixed to its respective plates. In certain embodiments, a majority of the spacers are fixed with their respective plates. In certain embodiments, all of the spacers are fixed with their respective plates.

In certain embodiments, a spacer is fixed to a plate monolithically.

In certain embodiments, the spacers are fixed to its respective plate by one or any combination of the following methods and/or configurations: attached to, bonded to, fused to, imprinted, and etched.

The term "imprinted" means that a spacer and a plate are fixed monolithically by imprinting (i.e. embossing) a piece of a material to form the spacer on the plate surface. The material can be single layer of a material or multiple layers of the material.

The term "etched" means that a spacer and a plate are fixed monolithically by etching a piece of a material to form the spacer on the plate surface. The material can be single layer of a material or multiple layers of the material.

The term "fused to" means that a spacer and a plate are fixed monolithically by attaching a spacer and a plate together, the original materials for the spacer and the plate fused into each other, and there is clear material boundary between the two materials after the fusion.

The term "bonded to" means that a spacer and a plate are fixed monolithically by binding a spacer and a plate by adhesion.

The term "attached to" means that a spacer and a plate are connected together.

In certain embodiments, the spacers and the plate are made in the same materials. In other embodiment, the spacers and the plate are made from different materials. In other embodiment, the spacer and the plate are formed in one piece. In other embodiment, the spacer has one end fixed to its respective plate, while the end is open for accommodating different configurations of the two plates.

In other embodiment, each of the spacers independently is at least one of attached to, bonded to, fused to, imprinted in, and etched in the respective plate. The term "independently" means that one spacer is fixed with its respective plate by a same or a different method that is selected from the methods of attached to, bonded to, fused to, imprinted in, and etched in the respective plate.

In certain embodiments, at least a distance between two spacers is predetermined ("predetermined inter-spacer distance" means that the distance is known when a user uses the plates.).

In certain embodiments of all methods and devices described herein, there are additional spacers besides to the fixed spacers.

(xiv) Specific Sample Thickness. In present invention, it was observed that a larger plate holding force (i.e. the force that holds the two plates together) can be achieved by using a smaller plate spacing (for a given sample area), or a larger sample area (for a given plate-spacing), or both.

In certain embodiments, at least one of the plates is transparent in a region encompassing the relevant area, each plate has an inner surface configured to contact the sample in the closed configuration; the inner surfaces of the plates are substantially parallel with each other, in the closed configuration; the inner surfaces of the plates are substantially planar, except the locations that have the spacers; or any combination of thereof.

The spacers can be fabricated on a plate in a variety of ways, using lithography, etching, embossing (nanoimprint), depositions, lift-off, fusing, or a combination of thereof. In certain embodiments, the spacers are directly embossed or imprinted on the plates. In certain embodiments, the spacers imprinted into a material (e.g. plastics) that is deposited on the plates. In certain embodiments, the spacers are made by directly embossing a surface of a CROF plate. The nano-imprinting can be done by roll to roll technology using a roller imprinter, or roll to a planar nanoimprint. Such process has a great economic advantage and hence lowering the cost.

In certain embodiments, the spacers are deposited on the plates. The deposition can be evaporation, pasting, or a lift-off. In the pasting, the spacer is fabricated first on a carrier, then the spacer is transferred from the carrier to the plate. In the lift-off, a removable material is first deposited on the plate and holes are created in the material; the hole bottom expose the plate surface and then a spacer material is deposited into the hole and afterwards the removable material is removed, leaving only the spacers on the plate surface. In certain embodiments, the spacers deposited on the plate are fused with the plate. In certain embodiments, the spacer and the plates are fabricated in a single process. The single process includes imprinting (i.e. embossing, molding) or synthesis.

In certain embodiments, at least two of the spacers are fixed to the respective plate by different fabrication methods, and optionally wherein the different fabrication methods include at least one of being deposition, bonded, fuse, imprinted, and etched.

In certain embodiments, one or more of the spacers are fixed to the respective plate(s) is by a fabrication method of being bonded, being fused, being imprinted, or being etched, or any combination of thereof.

In certain embodiments, the fabrication methods for forming such monolithic spacers on the plate include a method of being bonded, being fused, being imprinted, or being etched, or any combination of thereof.

(xv) $ISD^4/hE$

In certain embodiments of the present disclosure, a device for forming a thin fluidic sample layer with a uniform predetermined thickness by pressing can comprise a first plate. In certain embodiments of the present disclosure, a device for forming a thin fluidic sample layer with a uniform predetermined thickness by pressing can comprise a second plate. In certain embodiments of the present disclosure, a device for forming a thin fluidic sample layer with a uniform predetermined thickness by pressing can comprise spacers. In certain embodiments, the plates are movable relative to each other into different configurations. In certain embodiments, one or both plates are flexible. In certain embodiments, each of the plates comprises an inner surface that has a sample contact area for contacting a fluidic sample. In certain embodiments, each of the plates comprises, on its respective outer surface, a force area for applying a pressing force that forces the plates together. In certain embodiments, one or both of the plates comprise the spacers that are permanently fixed on the inner surface of a respective plate. In certain embodiments, the spacers have a predetermined substantially uniform height that is equal to or less than 200 microns, and a predetermined fixed inter-spacer-distance. In certain embodiments, the fourth power of the inter-spacer-distance (ISD) divided by the thickness (h) and the Young's modulus (E) of the flexible plate ($ISD^4/(hE)$) is $5 \times 10^6$ $um^3/GPa$ or less. In certain embodiments, at least one of the spacers is inside the sample contact area. In certain embodiments, one of the configurations is an open configuration, in which: the two plates are partially or completely separated apart, the spacing between the plates is not regulated by the spacers, and the sample is deposited on one or both of the plates. In certain embodiments, another of the configurations is a closed configuration which is configured after the sample is deposited in the open configuration and the plates are forced to the closed configuration by applying the pressing force on the force area; and in the closed configuration: at least part of the sample is compressed by the two plates into a layer of highly uniform thickness and is substantially stagnant relative to the plates, wherein the uniform thickness of the layer is confined by the sample contact areas of the two plates and is regulated by the plates and the spacers.

In certain embodiments of the present disclosure, a method of forming a thin fluidic sample layer with a uniform predetermined thickness by pressing can comprise obtaining a device of the present disclosure. In certain embodiments of the present disclosure, a method of forming a thin fluidic sample layer with a uniform predetermined thickness by pressing can comprise depositing a fluidic sample on one or both of the plates when the plates are configured in an open configuration. In certain embodiments, the open configuration is a configuration in which the two plates are partially or completely separated apart and the spacing between the plates is not regulated by the spacers. In certain embodiments of the present disclosure, a method of forming a thin fluidic sample layer with a uniform predetermined thickness by pressing can comprise forcing the two plates into a closed configuration, in which: at least part of the sample is compressed by the two plates into a layer of substantially uniform thickness, wherein the uniform thickness of the layer is confined by the sample contact surfaces of the plates and is regulated by the plates and the spacers.

In certain embodiments of the present disclosure, a device for analyzing a fluidic sample can comprise a first plate. In certain embodiments of the present disclosure, a device for analyzing a fluidic sample can comprise a second plate. In certain embodiments of the present disclosure, a device for analyzing a fluidic sample can comprise spacers. In certain embodiments, the plates are movable relative to each other into different configurations. In certain embodiments, one or both plates are flexible. In certain embodiments, each of the plates has, on its respective inner surface, a sample contact area for contacting a fluidic sample. In certain embodiments, one or both of the plates comprise the spacers and the spacers are fixed on the inner surface of a respective plate. In certain embodiments, the spacers have a predetermined substantially uniform height that is equal to or less than 200 microns, and the inter-spacer-distance is predetermined. In certain embodiments, the Young's modulus of the spacers multiplied by the filling factor of the spacers is at least 2 MPa. In certain embodiments, at least one of the spacers is inside the sample contact area. In certain embodiments, one of the configurations is an open configuration, in which: the two plates are partially or completely separated apart, the spacing between the plates is not regulated by the spacers, and the sample is deposited on one or both of the plates. In certain embodiments, another of the configurations is a closed configuration which is configured after the sample is deposited in the open configuration; and in the closed configuration: at least part of the sample is compressed by the two plates into a layer of highly uniform thickness, wherein the uniform thickness of the layer is confined by the sample contact surfaces of the plates and is regulated by the plates and the spacers.

In certain embodiments of the present disclosure, a method of forming a thin fluidic sample layer with a uniform predetermined thickness by pressing can comprise obtaining a device of the present disclosure. In certain embodiments of the present disclosure, a method of forming a thin fluidic sample layer with a uniform predetermined thickness by pressing can comprise depositing a fluidic sample on one or both of the plates when the plates are configured in an open configuration. In certain embodiments, the open configuration is a configuration in which the two plates are partially or completely separated apart and the spacing between the plates is not regulated by the spacers. In certain embodiments of the present disclosure, a method of forming a thin fluidic sample layer with a uniform predetermined thickness by pressing can comprise forcing the two plates into a closed configuration. In certain embodiments, at least part of the sample is compressed by the two plates into a layer of substantially uniform thickness, wherein the uniform thickness of the layer is confined by the sample contact surfaces of the plates and is regulated by the plates and the spacers.

In certain embodiments of the present disclosure, a device for analyzing a fluidic sample can comprise a first plate. In certain embodiments of the present disclosure, a device for analyzing a fluidic sample can comprise a second plate. In certain embodiments, the plates are movable relative to each other into different configurations. In certain embodiments, one or both plates are flexible. In certain embodiments, each of the plates has, on its respective surface, a sample contact area for contacting a sample that contains an analyte. In certain embodiments, one or both of the plates comprise spacers that are permanently fixed to a plate within a sample contact area, wherein the spacers have a predetermined substantially uniform height and a predetermined fixed inter-spacer distance that is at least about 2 times larger than the size of the analyte, up to 200 um, and wherein at least one of the spacers is inside the sample contact area. In certain embodiments, one of the configurations is an open configuration, in which: the two plates are separated apart, the spacing between the plates is not regulated by the spacers, and the sample is deposited on one or both of the plates. In certain embodiments, another of the configurations is a closed configuration which is configured after the sample deposition in the open configuration; and in the closed configuration: at least part of the sample is compressed by the two plates into a layer of highly uniform thickness, wherein the uniform thickness of the layer is confined by the sample contact surfaces of the plates and is regulated by the plates and the spacers.

In certain embodiments of the present disclosure, a method of forming a thin fluidic sample layer with a uniform predetermined thickness by pressing can comprise obtaining a device of the present disclosure. In certain embodiments of the present disclosure a method of forming a thin fluidic sample layer with a uniform predetermined thickness by pressing can comprise depositing a fluidic sample on one or both of the plates; when the plates are configured in an open configuration, wherein the open configuration is a configuration in which the two plates are partially or completely separated apart and the spacing between the plates is not regulated by the spacers. In certain embodiments of the present disclosure a method of forming a thin fluidic sample layer with a uniform predetermined thickness by pressing can comprise forcing the two plates into a closed configuration, in which: at least part of the sample is compressed by the two plates into a layer of substantially uniform thickness, wherein the uniform thickness of the layer is confined by the sample contact surfaces of the plates and is regulated by the plates and the spacers.

In certain embodiments of the present disclosure, a device for forming a thin fluidic sample layer with a uniform predetermined thickness by pressing can comprise a first plate. In certain embodiments of the present disclosure, a device for forming a thin fluidic sample layer with a uniform predetermined thickness by pressing can comprise a second plate. In certain embodiments of the present disclosure, a device for forming a thin fluidic sample layer with a uniform predetermined thickness by pressing can comprise spacers. In certain embodiments, the plates are movable relative to each other into different configurations. In certain embodiments, one or both plates are flexible. In certain embodiments, each of the plates comprises, on its respective inner surface, a sample contact area for contacting and/or compressing a fluidic sample. In certain embodiments, each of the plates comprises, on its respective outer surface, an area for applying a force that forces the plates together. In certain embodiments, one or both of the plates comprise the spacers that are permanently fixed on the inner surface of a respective plate. In certain embodiments, the spacers have a predetermined substantially uniform height that is equal to or less than 200 microns, a predetermined width, and a predetermined fixed inter-spacer-distance. In certain embodiments, a ratio of the inter-spacer-distance to the spacer width is 1.5 or larger. In certain embodiments, at least one of the spacers is inside the sample contact area. In certain embodiments, one of the configurations is an open configuration, in which: the two plates are partially or completely separated apart, the spacing between the plates is not regulated by the spacers, and the sample is deposited on one or both of the plates. In certain embodiments, another of the configurations is a closed configuration which is configured after the sample deposition in the open configuration; and in the closed configuration: at least part of the sample is compressed by the two plates into a layer of highly uniform thickness and is substantially stagnant relative to the plates, wherein the uniform thickness of the layer is confined by the sample contact areas of the two plates and is regulated by the plates and the spacers.

In certain embodiments of the present disclosure, a method of forming a thin fluidic sample layer with a uniform predetermined thickness by pressing with an imprecise pressing force can comprise obtaining a device of the present disclosure. In certain embodiments of the present disclosure, a method of forming a thin fluidic sample layer with a uniform predetermined thickness by pressing with an imprecise pressing force can comprise obtaining a fluidic sample. In certain embodiments of the present disclosure, a method of forming a thin fluidic sample layer with a uniform predetermined thickness by pressing with an imprecise pressing force can comprise depositing the sample on one or both of the plates; when the plates are configured in an open configuration, wherein the open configuration is a configuration in which the two plates are partially or completely separated apart and the spacing between the plates is not regulated by the spacers. In certain embodiments of the present disclosure, a method of forming a thin fluidic sample layer with a uniform predetermined thickness by pressing with an imprecise pressing force can comprise forcing the two plates into a closed configuration, in which: at least part of the sample is compressed by the two plates into a layer of substantially uniform thickness, wherein the uniform thickness of the layer is confined by the sample contact surfaces of the plates and is regulated by the plates and the spacers.

In certain embodiments, the spacers have a shape of pillar with a foot fixed on one of the plates and a flat top surface for contacting the other plate. In certain embodiments, the spacers have a shape of pillar with a foot fixed on one of the plates, a flat top surface for contacting the other plate, substantially uniform cross-section. In certain embodiments, the spacers have a shape of pillar with a foot fixed on one of the plates and a flat top surface for contacting the other plate, wherein the flat top surface of the pillars has a variation in less than 10 nm. In certain embodiments, the spacers have a shape of pillar with a foot fixed on one of the plates and a flat top surface for contacting the other plate, wherein the flat top surface of the pillars has a variation in less than 50 nm. In certain embodiments, the spacers have a shape of pillar with a foot fixed on one of the plates and a flat top surface for contacting the other plate, wherein the flat top surface of the pillars has a variation in less than 50 nm. In certain embodiments, the spacers have a shape of pillar with a foot fixed on one of the plates and a flat top surface for contacting the other plate, wherein the flat top surface of the pillars has a variation in less than 10 nm, 20 nm, 30 nm, 100 nm, 200 nm, or in a range of any two of the values.

In certain embodiments, the Young's modulus of the spacers multiplied by the filling factor of the spacers is at least 2 MPa. In certain embodiments, the sample comprises an analyte and the predetermined constant inter-spacer distance is at least about 2 times larger than the size of the analyte, up to 200 um. In certain embodiments, the sample comprise an analyte, the predetermined constant inter-spacer distance is at least about 2 times larger than the size of the analyte, up to 200 um, and the Young's modulus of the spacers multiplied by the filling factor of the spacers is at least 2 MPa.

In certain embodiments, a fourth power of the inter-spacer-distance (ISD) divided by the thickness (h) and the Young's modulus (E) of the flexible plate (ISD$^4$/(hE)) is $5\times10^6$ um$^3$/GPa or less. In certain embodiments, a fourth power of the inter-spacer-distance (ISD) divided by the thickness and the Young's modulus of the flexible plate (ISD$^4$/(hE)) is $1\times10^6$ um$^3$/GPa or less. In certain embodiments, a fourth power of the inter-spacer-distance (ISD) divided by the thickness and the Young's modulus of the flexible plate (ISD$^4$/(hE)) is $5\times10^5$ um$^3$/GPa or less. In certain embodiments, the Young's modulus of the spacers multiplied by the filling factor of the spacers is at least 2M Pa, and a fourth power of the inter-spacer-distance (ISD) divided by the thickness and the Young's modulus of the flexible plate (ISD$^4$/(hE)) is $1\times10^5$ um$^3$/GPa or less. In certain embodiments, the Young's modulus of the spacers multiplied by the filling factor of the spacers is at least 2 MPa, and a fourth power of the inter-spacer-distance (ISD) divided by the thickness and the Young's modulus of the flexible plate (ISD$^4$/(hE)) is $1\times10^4$ um$^3$/GPa or less. In certain embodiments, the Young's modulus of the spacers multiplied by the filling factor of the spacers is at least 20 MPa.

In certain embodiments of the present disclosure, the ratio of the inter-spacing distance of the spacers to the average width of the spacer is 2 or larger. In certain embodiments, the ratio of the inter-spacing distance of the spacers to the average width of the spacer is 2 or larger, and the Young's modulus of the spacers multiplied by the filling factor of the spacers is at least 2 MPa. In certain embodiments, the inter-spacer distance that is at least about 2 times larger than the size of the analyte, up to 200 um. In certain embodiments, a ratio of the inter-spacer-distance to the spacer width is 1.5 or larger. In certain embodiments, a ratio of the width to the height of the spacer is 1 or larger. In certain embodiments, a ratio of the width to the height of the spacer is 1.5 or larger. In certain embodiments, a ratio of the width to the height of the spacer is 2 or larger. In certain embodiments, a ratio of the width to the height of the spacer is larger than 2, 3, 5, 10, 20, 30, 50, or in a range of any two the value.

In certain embodiments, a force that presses the two plates into the closed configuration is an imprecise pressing force. In certain embodiments, a force that presses the two plates into the closed configuration is an imprecise pressing force provided by human hand. In certain embodiments, the forcing of the two plates to compress at least part of the sample into a layer of substantially uniform thickness comprises a use of a conformable pressing, either in parallel or sequentially, an area of at least one of the plates to press the plates together to a closed configuration, wherein the conformable pressing generates a substantially uniform pressure on the plates over the at least part of the sample, and the pressing spreads the at least part of the sample laterally between the sample contact surfaces of the plates, and wherein the closed configuration is a configuration in which the spacing between the plates in the layer of uniform thickness region is regulated by the spacers; and wherein the reduced thickness of the sample reduces the time for mixing the reagents on the storage site with the sample. In certain embodiments, the pressing force is an imprecise force that has a magnitude which is, at the time that the force is applied, either (a) unknown and unpredictable, or (b) cannot be known and cannot be predicted within an accuracy equal or better than 20% of the average pressing force applied. In certain embodiments, the pressing force is an imprecise force that has a magnitude which is, at the time that the force is applied, either (a) unknown and unpredictable, or (b) cannot be known and cannot be predicted within an accuracy equal or better than 30% of the average pressing force applied. In certain embodiments, the pressing force is an imprecise force that has a magnitude which is, at the time that the force is applied, either (a) unknown and unpredictable, or (b) cannot be known and cannot be predicted within an accuracy equal or better than 30% of the average pressing force applied; and wherein the layer of highly uniform thickness has a variation in thickness uniform of 20% or less. In certain embodiments, the pressing force is an imprecise force that has a magnitude which cannot, at the time that the force is applied, be determined within an accuracy equal or better than 30%, 40%, 50%, 70%, 100%, 200%, 300%, 500%, 1000%, 2000%, or in a range between any of the two values.

In certain embodiments of the present disclosure, the flexible plate has a thickness of in the range of 10 um to 200 um. In certain embodiments, the flexible plate has a thickness of in the range of 20 um to 100 um. In certain embodiments, the flexible plate has a thickness of in the range of 25 um to 180 um. In certain embodiments, the flexible plate has a thickness of in the range of 200 um to 260 um. In certain embodiments, the flexible plate has a thickness of equal to or less than 250 um, 225 um, 200 um, 175 um, 150 um, 125 um, 100 um, 75 um, 50 um, 25 um, 10 um, 5 um, 1 um, or in a range between the two of the values. In certain embodiments, the sample has a viscosity in the range of 0.1 to 4 (mPa s). In certain embodiments, the flexible plate has a thickness of in the range of 200 um to 260 um. In certain embodiments, the flexible plate has a thickness in the range of 20 um to 200 um and Young's modulus in the range 0.1 to 5 GPa.

In certain embodiments of the present disclosure, the sample deposition is a deposition directly from a subject to the plate without using any transferring devices. In certain embodiments, during the deposition, the amount of the sample deposited on the plate is unknown. In certain embodiments, the method further comprises an analyzing that analyze the sample. In certain embodiments, the analyzing comprises calculating the volume of a relevant sample volume by measuring the lateral area of the relevant sample volume and calculating the volume from the lateral area and the predetermined spacer height. In certain embodiments, the pH value at location of a sample that is between the two plates in a closed configuration is determined by the volume of the location and by analyzing an image(s) taken from that location. In certain embodiments, the determination by analyzing an image uses artificial intelligence and machine learning.

In certain embodiments, the analyzing step (e) comprises measuring: i. imaging, ii. luminescence selected from photoluminescence, electroluminescence, and electrochemiluminescence, iii. surface Raman scattering, iv. electrical impedance selected from resistance, capacitance, and inductance, or v. any combination of i-iv. In certain embodiments, the analyzing comprises reading, image analysis, or counting of the analyte, or a combination of thereof. In certain embodiments, the sample contains one or plurality of analytes, and one or both plate sample contact surfaces comprise one or a plurality of binding sites that each binds and immobilize a respective analyte. In certain embodiments, one or both plate sample contact surfaces comprise one or a plurality of storage sites that each stores a reagent or reagents, wherein the reagent(s) dissolve and diffuse in the sample. In certain embodiments, one or both plate sample contact surfaces comprises one or a plurality of amplification sites that are each capable of amplifying a signal from the analyte or a label of the analyte when the analyte or label is within 500 nm from an amplification site. In certain embodiments, i. one or both plate sample contact surfaces comprise one or a plurality of binding sites that each binds and immobilize a respective analyte; or ii. one or both plate sample contact surfaces comprise, one or a plurality of storage sites that each stores a reagent or reagents; wherein the reagent(s) dissolve and diffuse in the sample, and wherein the sample contains one or plurality of analytes; or iii. one or a plurality of amplification sites that are each capable of amplifying a signal from the analyte or a label of the analyte when the analyte or label is 500 nm from the amplification site; or iv. any combination of i to iii.

In certain embodiments, the liquid sample is a biological sample selected from amniotic fluid, aqueous humour, vitreous humour, blood (e.g., whole blood, fractionated blood, plasma or serum), breast milk, cerebrospinal fluid (CSF), cerumen (earwax), chyle, chime, endolymph, perilymph, feces, breath, gastric acid, gastric juice, lymph, mucus (including nasal drainage and phlegm), pericardial fluid, peritoneal fluid, pleural fluid, pus, rheum, saliva, exhaled breath condensates, sebum, semen, sputum, sweat, synovial fluid, tears, vomit, and urine.

In certain embodiments, the layer of uniform thickness in the closed configuration is less than 150 um. In certain embodiments, the pressing is provided by a pressured liquid, a pressed gas, or a conformal material. In certain embodiments, the analyzing comprises counting cells in the layer of uniform thickness. In certain embodiments, the analyzing comprises performing an assay in the layer of uniform thickness. In certain embodiments, In certain embodiments, the assay is a binding assay or biochemical assay. In certain embodiments, the sample deposited has a total volume less 0.5 uL. In certain embodiments, multiple drops of sample are deposited onto one or both of the plates.

In certain embodiments, the inter-spacer distance is in the range of 1 μm to 120 μm. In certain embodiments, the inter-spacer distance is in the range of 120 μm to 50 μm. In certain embodiments, the inter-spacer distance is in the range of 120 μm to 200 μm. In certain embodiments, the flexible plates have a thickness in the range of 20 um to 250 um and Young's modulus in the range 0.1 to 5 GPa. In certain embodiments, for a flexible plate, the thickness of the flexible plate times the Young's modulus of the flexible plate is in the range 60 to 750 GPa-um.

In certain embodiments, the layer of uniform thickness sample is uniform over a lateral area that is at least 1 mm$^2$. In certain embodiments, the layer of uniform thickness sample is uniform over a lateral area that is at least 3 mm$^2$. In certain embodiments, the layer of uniform thickness sample is uniform over a lateral area that is at least 5 mm$^2$.

In certain embodiments, In certain embodiments, the layer of uniform thickness sample is uniform over a lateral area that is at least 10 mm². In certain embodiments, the layer of uniform thickness sample is uniform over a lateral area that is at least 20 mm². In certain embodiments, the layer of uniform thickness sample is uniform over a lateral area that is in a range of 20 mm² to 100 mm². In certain embodiments, the layer of uniform thickness sample has a thickness uniformity of up to +/−5% or better. In certain embodiments, the layer of uniform thickness sample has a thickness uniformity of up to +/−10% or better. In certain embodiments, the layer of uniform thickness sample has a thickness uniformity of up to +/−20% or better. In certain embodiments, the layer of uniform thickness sample has a thickness uniformity of up to +/−30% or better. In certain embodiments, the layer of uniform thickness sample has a thickness uniformity of up to +/−40% or better. In certain embodiments, the layer of uniform thickness sample has a thickness uniformity of up to +/−50% or better.

In certain embodiments, the spacers are pillars with a cross-sectional shape selected from round, polygonal, circular, square, rectangular, oval, elliptical, or any combination of the same. In certain embodiments, the spacers have pillar shape, have a substantially flat top surface, and have substantially uniform cross-section, wherein, for each spacer, the ratio of the lateral dimension of the spacer to its height is at least 1. In certain embodiments, the inter spacer distance is periodic. In certain embodiments, the spacers have a filling factor of 1% or higher, wherein the filling factor is the ratio of the spacer contact area to the total plate area. In certain embodiments, the Young's modulus of the spacers times the filling factor of the spacers is equal or larger than 20 MPa, wherein the filling factor is the ratio of the spacer contact area to the total plate area. In certain embodiments, the spacing between the two plates at the closed configuration is in less 200 um. In certain embodiments, the spacing between the two plates at the closed configuration is a value selected from between 1.8 um and 3.5 um. In certain embodiments, the spacing are fixed on a plate by directly embossing the plate or injection molding of the plate. In certain embodiments, the materials of the plate and the spacers are selected from polystyrene, PMMA, PC, COC, COP, or another plastic. In certain embodiments, the spacers have a pillar shape, and the sidewall corners of the spacers have a round shape with a radius of curvature at least 1 µm. In certain embodiments, the spacers have a density of at least 1000/mm². In certain embodiments, at least one of the plates is transparent. In certain embodiments, the mold used to make the spacers is fabricated by a mold containing features that are fabricated by either (a) directly reactive ion etching or ion beam etched or (b) by a duplication or multiple duplication of the features that are reactive ion etched or ion beam etched.

In certain embodiments, the spacers are configured, such that the filling factor is in the range of 1% to 5%. In certain embodiments, the surface variation is relative to the spacer height and the ratio of the pillar flat top surface variation to the spacer height is less than 0.5%, 1%, 3%, 5%, 7%, 10%, 15%, 20%, 30%, 40%, or in a range between any two of the values. A preferred flat pillar top smoothness has a ratio of the pillar flat top surface variation to the spacer height is less than 2%, 5%, or 10%. In certain embodiments, the spacers are configured, such that the filling factor is in the range of 1% to 5%. In certain embodiments, the spacers are configured, such that the filling factor is in the range of 5% to 10%. In certain embodiments, the spacers are configured, such that the filling factor is in the range of 10% to 20%. In certain embodiments, the spacers are configured, such that the filling factor is in the range of 20% to 30%. In certain embodiments, the spacers are configured, such that the filling factor is 5%, 10%, 20%, 30%, 40%, 50%, or in a range of any two of the values. In certain embodiments, the spacers are configured, such that the filling factor is 50%, 60%, 70%, 80%, or in a range of any two of the values.

In certain embodiments, the spacers are configured, such that the filling factor multiplies the Young's modulus of the spacer is in the range of 2 MPa and 10 MPa. In certain embodiments, the spacers are configured, such that the filling factor multiplies the Young's modulus of the spacer is in the range of 10 MPa and 20 MPa. In certain embodiments, the spacers are configured, such that the filling factor multiplies the Young's modulus of the spacer is in the range of 20 MPa and 40 MPa. In certain embodiments, the spacers are configured, such that the filling factor multiplies the Young's modulus of the spacer is in the range of 40 MPa and 80 MPa. In certain embodiments, the spacers are configured, such that the filling factor multiplies the Young's modulus of the spacer is in the range of 80 MPa and 120 MPa. In certain embodiments, the spacers are configured, such that the filling factor multiplies the Young's modulus of the spacer is in the range of 120 MPa to 150 MPa.

In certain embodiments, the device further comprises a dry reagent coated on one or both plates. In certain embodiments, the device further comprises, on one or both plates, a dry binding site that has a predetermined area, wherein the dry binding site binds to and immobilizes an analyte in the sample. In certain embodiments, the device further comprises, on one or both plates, a releasable dry reagent and a release time control material that delays the time that the releasable dry regent is released into the sample. In certain embodiments, the release time control material delays the time that the dry regent starts is released into the sample by at least 3 seconds. In certain embodiments, the regent comprises anticoagulant and/or staining reagent(s). In certain embodiments, the reagent comprises cell lysing reagent(s). In certain embodiments, the device further comprises, on one or both plates, one or a plurality of dry binding sites and/or one or a plurality of reagent sites. In certain embodiments, the analyte comprises a molecule (e.g., a protein, peptides, DNA, RNA, nucleic acid, or other molecule), cells, tissues, viruses, and nanoparticles with different shapes. In certain embodiments, the analyte comprises white blood cells, red blood cells and platelets. In certain embodiments, the analyte is stained.

In certain embodiments, the spacers regulating the layer of uniform thickness have a filling factor of at least 1%, wherein the filling factor is the ratio of the spacer area in contact with the layer of uniform thickness to the total plate area in contact with the layer of uniform thickness. In certain embodiments, for spacers regulating the layer of uniform thickness, the Young's modulus of the spacers times the filling factor of the spacers is equal or larger than 10 MPa, wherein the filling factor is the ratio of the spacer area in contact with the layer of uniform thickness to the total plate area in contact with the layer of uniform thickness. In certain embodiments, for a flexible plate, the thickness of the flexible plate times the Young's modulus of the flexible plate is in the range 60 to 750 GPa-um. In certain embodiments, for a flexible plate, the fourth power of the inter-spacer-distance (ISD) divided by the thickness of the flexible plate (h) and the Young's modulus (E) of the flexible plate, $ISD^4/(hE)$, is equal to or less than $10^6$ um³/GPa.

III. Formation of Uniform Thin Fluidic Layer by an Imprecise Force Pressing

In certain embodiment of the present invention, a uniform thin fluidic sample layer is formed by using a pressing with an imprecise force. The term "imprecise pressing force" without adding the details and then adding a definition for imprecise pressing force. As used herein, the term "imprecise" in the context of a force (e.g. "imprecise pressing force") refers to a force that (a) has a magnitude that is not precisely known or precisely predictable at the time the force is applied; (b) has a pressure in the range of 0.01 kg/cm$^2$ (centimeter square) to 100 kg/cm$^2$, (c) varies in magnitude from one application of the force to the next; and (d) the imprecision (i.e. the variation) of the force in (a) and (c) is at least 20% of the total force that actually is applied.

An imprecise force can be applied by human hand, for example, e.g., by pinching an object together between a thumb and index finger, or by pinching and rubbing an object together between a thumb and index finger.

In some embodiments, the imprecise force by the hand pressing has a pressure of 0.01 kg/cm2, 0.1 kg/cm2, 0.5 kg/cm2, 1 kg/cm2, 2 kg/cm2, kg/cm2, 5 kg/cm2, 10 kg/cm2, 20 kg/cm2, 30 kg/cm2, 40 kg/cm2, 50 kg/cm2, 60 kg/cm2, 100 kg/cm2, 150 kg/cm2, 200 kg/cm2, or a range between any two of the values; and a preferred range of 0.1 kg/cm2 to 0.5 kg/cm2, 0.5 kg/cm2 to 1 kg/cm2, 1 kg/cm2 to 5 kg/cm2, 5 kg/cm2 to 10 kg/cm2 (Pressure).

B) Adaptor

Details of the Adaptor are described in detail in a variety of publications including International Application No. PCT/US2018/017504 (Essenlix Docket No. ESXPCT18F04), which is hereby incorporated by reference herein for all purposes.

The present invention that is described herein address this problem by providing a system comprising an optical adaptor and a smartphone. The optical adaptor device fits over a smartphone converting it into a microscope which can take both fluorescent and bright-field images of a sample. This system can be operated conveniently and reliably by a common person at any location. The optical adaptor takes advantage of the existing resources of the smartphone, including camera, light source, processor and display screen, which provides a low-cost solution let the user to do bright-field and fluorescent microscopy.

In this invention, the optical adaptor device comprises a holder frame fitting over the upper part of the smartphone and an optical box attached to the holder having sample receptacle slot and illumination optics. In some references (U.S. Pat. No. 2016/029091 and U.S. Pat. No. 2011/0292198), their optical adaptor design is a whole piece including both the clip-on mechanics parts to fit over the smartphone and the functional optics elements. This design has the problem that they need to redesign the whole-piece optical adaptor for each specific model of smartphone. But in this present invention, the optical adaptor is separated into a holder frame only for fitting a smartphone and a universal optical box containing all the functional parts. For the smartphones with different dimensions, as long as the relative positions of the camera and the light source are the same, only the holder frame need to be redesigned, which will save a lot of cost of design and manufacture.

The optical box of the optical adaptor comprises: a receptacle slot which receives and position the sample in a sample slide in the field of view and focal range of the smartphone camera; a bright-field illumination optics for capturing bright-field microscopy images of a sample; a fluorescent illumination optics for capturing fluorescent microscopy images of a sample; a lever to switch between bright-field illumination optics and fluorescent illumination optics by sliding inward and outward in the optical box.

The receptacle slot has a rubber door attached to it, which can fully cover the slot to prevent the ambient light getting into the optical box to be collected by the camera. In U.S. Pat. 2016/0290916, the sample slot is always exposed to the ambient light which won't cause too much problem because it only does bright-field microscopy. But the present invention can take the advantage of this rubber door when doing fluorescent microscopy because the ambient light would bring a lot of noise to the image sensor of the camera.

To capture good fluorescent microscopy image, it is desirable that nearly no excitation light goes into the camera and only the fluorescent emitted by the sample is collected by the camera. For all common smartphones, however, the optical filter putting in front of the camera cannot block the undesired wavelength range of the light emitted from the light source of a smartphone very well due to the large divergence angle of the beams emitted by the light source and the optical filter not working well for un-collimated beams. Collimation optics can be designed to collimated the beam emitted by the smartphone light source to address this issue, but this approach increase the size and cost of the adaptor. Instead, in this present invention, fluorescent illumination optics enables the excitation light to illuminate the sample partially from the waveguide inside the sample slide and partially from the backside of the sample side in large oblique incidence angle so that excitation light will nearly not be collected by the camera to reduce the noise signal getting into the camera.

The bright-field illumination optics in the adaptor receive and turn the beam emitted by the light source so as to back-illuminated the sample in normal incidence angle.

Typically, the optical box also comprises a lens mounted in it aligned with the camera of the smartphone, which magnifies the images captured by the camera. The images captured by the camera can be further processed by the processor of smartphone and outputs the analysis result on the screen of smartphone.

To achieve both bright-field illumination and fluorescent illumination optics in a same optical adaptor, in this present invention, a slidable lever is used. The optical elements of the fluorescent illumination optics are mounted on the lever and when the lever fully slides into the optical box, the fluorescent illumination optics elements block the optical path of bright-field illumination optics and switch the illumination optics to fluorescent illumination optics. And when the lever slides out, the fluorescent illumination optics elements mounted on the lever move out of the optical path and switch the illumination optics to bright-field illumination optics. This lever design makes the optical adaptor work in both bright-field and fluorescent illumination modes without the need for designing two different single-mode optical boxes.

The lever comprises two planes at different planes at different heights.

In certain embodiments, two planes can be joined together with a vertical bar and move together in or out of the optical box. In certain embodiments, two planes can be separated and each plane can move individually in or out of the optical box.

The upper lever plane comprises at least one optical element which can be, but not limited to be an optical filter.

The upper lever plane moves under the light source and the preferred distance between the upper lever plane and the light source is in the range of 0 to 5 mm.

Part of the bottom lever plane is not parallel to the image plane. And the surface of the non-parallel part of the bottom lever plane has mirror finish with high reflectivity larger than 95%. The non-parallel part of the bottom lever plane moves under the light source and deflects the light emitted from the light source to back-illuminate the sample area right under the camera. The preferred tilt angle of the non-parallel part of the bottom lever plane is in the range of 45 degree to 65 degree and the tilt angle is defined as the angle between the non-parallel bottom plane and the vertical plane.

Part of the bottom lever plane is parallel to the image plane and is located under and 1 mm to 10 mm away from the sample. The surface of the parallel part of the bottom lever plane is highly light absorptive with light absorption larger than 95%. This absorptive surface is to eliminate the reflective light back-illuminating on the sample in small incidence angle.

To slide in and out to switch the illumination optics using the lever, a stopper design comprising a ball plunger and a groove on the lever is used in order to stop the lever at a pre-defined position when being pulled outward from the adaptor. This allow the user to use arbitrary force the pull the lever but make the lever to stop at a fixed position where the optical adaptor's working mode is switched to bright-filed illumination.

A sample slider is mounted inside the receptacle slot to receive the QMAX device and position the sample in the QMAX device in the field of view and focal range of the smartphone camera.

The sample slider comprises a fixed track frame and a moveable arm:

The frame track is fixedly mounted in the receptacle slot of the optical box. And the track frame has a sliding track slot that fits the width and thickness of the QMAX device so that the QMAX device can slide along the track. The width and height of the track slot is carefully configured to make the QMAX device shift less than 0.5 mm in the direction perpendicular to the sliding direction in the sliding plane and shift less than less than 0.2 mm along the thickness direction of the QMAX device.

The frame track has an opened window under the field of view of the camera of smartphone to allow the light back-illuminate the sample.

A moveable arm is pre-built in the sliding track slot of the track frame and moves together with the QMAX device to guide the movement of QMAX device in the track frame.

The moveable arm equipped with a stopping mechanism with two pre-defined stop positions. For one position, the arm will make the QMAX device stop at the position where a fixed sample area on the QMAX device is right under the camera of smartphone. For the other position, the arm will make the QMAX device stop at the position where the sample area on QMAX device is out of the field of view of the smartphone and the QMAX device can be easily taken out of the track slot.

The moveable arm switches between the two stop positions by a pressing the QMAX device and the moveable arm together to the end of the track slot and then releasing.

The moveable arm can indicate if the QMAX device is inserted in correct direction. The shape of one corner of the QMAX device is configured to be different from the other three right angle corners. And the shape of the moveable arm matches the shape of the corner with the special shape so that only in correct direction can QMAX device slide to correct position in the track slot.

C) Smartphone/Detection System

Details of the Smartphone/Detection System are described in detail in a variety of publications including International Application (IA) No. PCT/US2016/046437 filed on Aug. 10, 2016, IA No. PCT/US2016/051775 filed Sep. 14, 2016, U.S. Provisional Application No. 62/456,065, which was filed on Feb. 7, 2017, U.S. Provisional Application Nos. 62/456,287 and 62/456,590, which were filed on Feb. 8, 2017, U.S. Provisional Application No. 62/456,504, which was filed on Feb. 8, 2017, U.S. Provisional Application No. 62/459,544, which was filed on Feb. 15, 2017, and U.S. Provisional Application Nos. 62/460,075 and 62/459,920, which were filed on Feb. 16, 2017, each of which are hereby incorporated herein by reference in their entirety for all purposes.

The devices/apparatus, systems, and methods herein disclosed can include or use Q-cards for sample detection, analysis, and quantification. In certain embodiments, the Q-card is used together with an adaptor that can connect the Q-card with a smartphone detection system. In certain embodiments, the smartphone comprises a camera and/or an illumination source. In certain embodiments, the smartphone comprises a camera, which can be used to capture images or the sample when the sample is positioned in the field of view of the camera (e.g. by an adaptor). In certain embodiments, the camera includes one set of lenses (e.g. as in iPhone™ 6). In certain embodiments, the camera includes at least two sets of lenses (e.g. as in iPhone™ 7). In certain embodiments, the smartphone comprises a camera, but the camera is not used for image capturing.

In certain embodiments, the smartphone comprises a light source such as but not limited to LED (light emitting diode). In certain embodiments, the light source is used to provide illumination to the sample when the sample is positioned in the field of view of the camera (e.g. by an adaptor). In certain embodiments, the light from the light source is enhanced, magnified, altered, and/or optimized by optical components of the adaptor.

In certain embodiments, the smartphone comprises a processor that is configured to process the information from the sample. The smartphone includes software instructions that, when executed by the processor, can enhance, magnify, and/or optimize the signals (e.g. images) from the sample. The processor can include one or more hardware components, such as a central processing unit (CPU), an application-specific integrated circuit (ASIC), an application-specific instruction-set processor (ASIP), a graphics processing unit (GPU), a physics processing unit (PPU), a digital signal processor (DSP), a field-programmable gate array (FPGA), a programmable logic device (PLD), a controller, a micro-controller unit, a reduced instruction-set computer (RISC), a microprocessor, or the like, or any combination thereof.

In certain embodiments, the smartphone comprises a communication unit, which is configured and/or used to transmit data and/or images related to the sample to another device. Merely by way of example, the communication unit can use a cable network, a wireline network, an optical fiber network, a telecommunications network, an intranet, the Internet, a local area network (LAN), a wide area network (WAN), a wireless local area network (WLAN), a metropolitan area network (MAN), a wide area network (WAN), a public telephone switched network (PSTN), a Bluetooth network, a ZigBee network, a near field communication (NFC) network, or the like, or any combination thereof. In certain embodiments, the smartphone is an iPhone™, an Android™ phone, or a Windows™ phone.

D) Method of Manufacture

Details of the Method of Manufacture are described in detail in a variety of publications including International Application No. PCT/US2018/057873 filed Oct. 26, 2018, which is hereby incorporated by reference herein for all purposes.

Devices of the disclosure can be fabricated using techniques well known in the art. The choice of fabrication technique will depend on the material used for the device and the size of the spacer array and/or the size of the spacers. Exemplary materials for fabricating the devices of the invention include glass, silicon, steel, nickel, polymers, e.g., poly(methylmethacrylate) (PMMA), polycarbonate, polystyrene, polyethylene, polyolefins, silicones (e.g., poly(dimethylsiloxane)), polypropylene, cis-polyisoprene (rubber), poly(vinyl chloride) (PVC), poly(vinyl acetate) (PVAc), polychloroprene (neoprene), polytetrafluoroethylene (Teflon), poly(vinylidene chloride) (SaranA), and cyclic olefin polymer (COP) and cyclic olefin copolymer (COC), and combinations thereof. Other materials are known in the art. For example, deep Reactive Ion Etch (DRIE) is used to fabricate silicon-based devices with small gaps, small spacers and large aspect ratios (ratio of spacer height to lateral dimension). Thermoforming (embossing, injection molding) of plastic devices can also be used, e.g., when the smallest lateral feature is >20 microns and the aspect ratio of these features is ☐10.

Additional methods include photolithography (e.g., stereolithography or x-ray photolithography), molding, embossing, silicon micromachining, wet or dry chemical etching, milling, diamond cutting, Lithographie Galvanoformung and Abformung (LIGA), and electroplating. For example, for glass, traditional silicon fabrication techniques of photolithography followed by wet (KOH) or dry etching (reactive ion etching with fluorine or other reactive gas) can be employed. Techniques such as laser nicromachining can be adopted for plastic materials with high photon absorption efficiency. This technique is suitable for lower throughput fabrication because of the serial nature of the process. For mass-produced plastic devices, thermoplastic injection molding, and compression molding can be suitable. Conventional thermoplastic injection molding used for mass-fabrication of compact discs (which preserves fidelity of features in sub-microns) can also be employed to fabricate the devices of the invention. For example, the device features are replicated on a glass master by conventional photolithography. The glass master is electroformed to yield a tough, thermal shock resistant, thermally conductive, hard mold. This mold serves as the master template for injection molding or compression molding the features into a plastic device. Depending on the plastic material used to fabricate the devices and the requirements on optical quality and throughput of the finished product, compression molding or injection molding can be chosen as the method of manufacture. Compression molding (also called hot embossing or relief imprinting) has the advantages of being compatible with high molecular weight polymers, which are excellent for small structures and can replicate high aspect ratio structures but has longer cycle times. Injection molding works well for low aspect ratio structures and is most suitable for low molecular weight polymers.

A device can be fabricated in one or more pieces that are then assembled. Layers of a device can be bonded together by clamps, adhesives, heat, anodic bonding, or reactions between surface groups (e.g., wafer bonding). Alternatively, a device with channels or gaps in more than one plane can be fabricated as a single piece, e.g., using stereolithography or other three-dimensional fabrication techniques.

To reduce non-specific adsorption of cells or compounds released by lysed cells onto the surfaces of the device, one or more surfaces of the device can be chemically modified to be non-adherent or repulsive. The surfaces can be coated with a thin film coating (e.g., a monolayer) of commercial non-stick reagents, such as those used to form hydrogels. Additional examples chemical species that can be used to modify the surfaces of the device include oligoethylene glycols, fluorinated polymers, organosilanes, thiols, polyethylene glycol, hyaluronic acid, bovine serum albumin, poly-vinyl alcohol, mucin, poly-HEMA, methacrylated PEG, and agarose. Charged polymers can also be employed to repel oppositely charged species. The type of chemical species used for repulsion and the method of attachment to the surfaces of the device will depend on the nature of the species being repelled and the nature of the surfaces and the species being attached. Such surface modification techniques are well known in the art. The surfaces can be functionalized before or after the device is assembled. The surfaces of the device can also be coated in order to capture materials in the sample, e.g., membrane fragments or proteins.

In certain embodiments of the present disclosure, a method for fabricating any Q-Card of the present disclosure can comprise injection molding of the first plate. In certain embodiments of the present disclosure, a method for fabricating any Q-Card of the present disclosure can comprise nanoimprinting or extrusion printing of the second plate. In certain embodiments of the present disclosure, a method for fabricating any Q-Card of the present disclosure can comprise Laser cutting the first plate. In certain embodiments of the present disclosure, a method for fabricating any Q-Card of the present disclosure can comprise nanoimprinting or extrusion printing of the second plate. In certain embodiments of the present disclosure, a method for fabricating any Q-Card of the present disclosure can comprise injection molding and laser cutting the first plate. In certain embodiments of the present disclosure, a method for fabricating any Q-Card of the present disclosure can comprise nanoimprinting or extrusion printing of the second plate. In certain embodiments of the present disclosure, a method for fabricating any Q-Card of the present disclosure can comprise nanoimprinting or extrusion printing to fabricated both the first and the second plate. In certain embodiments of the present disclosure, a method for fabricating any Q-Card of the present disclosure can comprise fabricating the first plate or the second plate, using injection molding, laser cutting the first plate, nanoimprinting, extrusion printing, or a combination of thereof. In certain embodiments of the present disclosure, a method for fabricating any Q-Card of the present disclosure can comprise a step of attaching the hinge on the first and the second plates after the fabrication of the first and second plates.

E) Sample Types & Subjects

Details of the Samples & Subjects are described in detail in a variety of publications including International Application (IA) No. PCT/US2016/046437 filed on Aug. 10, 2016, IA No. PCT/US2016/051775 filed on Sep. 14, 2016, IA No.

PCT/US201/017307 filed on Feb. 7, 2018, IA No. and PCT/US2017/065440 filed on Dec. 8, 2017, each of which is hereby incorporated by reference herein for all purposes.

A sample can be obtained from a subject. A subject as described herein can be of any age and can be an adult, infant or child. In some cases, the subject is 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 years old, or within a range therein (e.g., between 2 and 20 years old, between 20 and 40 years old, or between 40 and 90 years old). A particular class of subjects that can benefit is subjects who have or are suspected of having an infection (e.g., a bacterial and/or a viral infection). Another particular class of subjects that can benefit is subjects who can be at higher risk of getting an infection. Furthermore, a subject treated by any of the methods or compositions described herein can be male or female. Any of the methods, devices, or kits disclosed herein can also be performed on a non-human subject, such as a laboratory or farm animal. Non-limiting examples of a non-human subjects include a dog, a goat, a guinea pig, a hamster, a mouse, a pig, a non-human primate (e.g., a gorilla, an ape, an orangutan, a lemur, or a baboon), a rat, a sheep, a cow, or a zebrafish.

The devices, apparatus, systems, and methods herein disclosed can be used for samples such as but not limited to diagnostic samples, clinical samples, environmental samples and foodstuff samples.

For example, in certain embodiments, the devices, apparatus, systems, and methods herein disclosed are used for a sample that includes cells, tissues, bodily fluids and/or a mixture thereof. In certain embodiments, the sample comprises a human body fluid. In certain embodiments, the sample comprises at least one of cells, tissues, bodily fluids, stool, amniotic fluid, aqueous humour, vitreous humour, blood, whole blood, fractionated blood, plasma, serum, breast milk, cerebrospinal fluid, cerumen, chyle, chime, endolymph, perilymph, feces, gastric acid, gastric juice, lymph, mucus, nasal drainage, phlegm, pericardial fluid, peritoneal fluid, pleural fluid, pus, rheum, saliva, sebum, semen, sputum, sweat, synovial fluid, tears, vomit, urine, and exhaled breath condensate.

In certain embodiments, the devices, apparatus, systems, and methods herein disclosed are used for an environmental sample that is obtained from any suitable source, such as but not limited to: river, lake, pond, ocean, glaciers, icebergs, rain, snow, sewage, reservoirs, tap water, drinking water, etc.; solid samples from soil, compost, sand, rocks, concrete, wood, brick, sewage, etc.; and gaseous samples from the air, underwater heat vents, industrial exhaust, vehicular exhaust, etc. In certain embodiments, the environmental sample is fresh from the source; in certain embodiments, the environmental sample is processed. For example, samples that are not in liquid form are converted to liquid form before the subject devices, apparatus, systems, and methods are applied.

In certain embodiments, the devices, apparatus, systems, and methods herein disclosed are used for a foodstuff sample, which is suitable or has the potential to become suitable for animal consumption, e.g., human consumption. In certain embodiments, a foodstuff sample includes raw ingredients, cooked or processed food, plant and animal sources of food, preprocessed food as well as partially or fully processed food, etc. In certain embodiments, samples that are not in liquid form are converted to liquid form before the subject devices, apparatus, systems, and methods are applied.

The subject devices, apparatus, systems, and methods can be used to analyze any volume of the sample. Examples of the volumes include, but are not limited to, about 10 mL or less, 5 mL or less, 3 mL or less, 1 microliter (uL, also "uL" herein) or less, 500 uL or less, 300 uL or less, 250 uL or less, 200 uL or less, 170 uL or less, 150 uL or less, 125 uL or less, 100 uL or less, 75 uL or less, 50 uL or less, 25 uL or less, 20 uL or less, 15 uL or less, 10 uL or less, 5 uL or less, 3 uL or less, 1 uL or less, 0.5 uL or less, 0.1 uL or less, 0.05 uL or less, 0.001 uL or less, 0.0005 uL or less, 0.0001 uL or less, 10 pL or less, 1 pL or less, or a range between any two of the values.

In certain embodiments, the volume of the sample includes, but is not limited to, about 100 uL or less, 75 uL or less, 50 uL or less, 25 uL or less, 20 uL or less, 15 uL or less, 10 uL or less, 5 uL or less, 3 uL or less, 1 uL or less, 0.5 uL or less, 0.1 uL or less, 0.05 uL or less, 0.001 uL or less, 0.0005 uL or less, 0.0001 uL or less, 10 pL or less, 1 pL or less, or a range between any two of the values. In certain embodiments, the volume of the sample includes, but is not limited to, about 10 uL or less, 5 uL or less, 3 uL or less, 1 uL or less, 0.5 uL or less, 0.1 uL or less, 0.05 uL or less, 0.001 uL or less, 0.0005 uL or less, 0.0001 uL or less, 10 pL or less, 1 pL or less, or a range between any two of the values.

In certain embodiments, the amount of the sample is about a drop of liquid. In certain embodiments, the amount of sample is the amount collected from a pricked finger or fingerstick. In certain embodiments, the amount of sample is the amount collected from a microneedle, micropipette or a venous draw.

F) Machine Learning

Details of the Network are described in detail in a variety of publications including International Application (IA) No. PCT/US2018/017504 filed Feb. 8, 2018, and PCT/US2018/057877 filed Oct. 26, 2018, each of which are hereby incorporated by reference herein for all purposes.

One aspect of the present invention provides a framework of machine learning and deep learning for analyte detection and localization. A machine learning algorithm is an algorithm that is able to learn from data. A more rigorous definition of machine learning is "A computer program is said to learn from experience E with respect to some class of tasks T and performance measure P, if its performance at tasks in T, as measured by P, improves with experience E." It explores the study and construction of algorithms that can learn from and make predictions on data—such algorithms overcome the static program instructions by making data driven predictions or decisions, through building a model from sample inputs.

Deep learning is a specific kind of machine learning based on a set of algorithms that attempt to model high level abstractions in data. In a simple case, there might be two sets of neurons: ones that receive an input signal and ones that send an output signal. When the input layer receives an input, it passes on a modified version of the input to the next layer. In a deep network, there are many layers between the input and output (and the layers are not made of neurons but it can help to think of it that way), allowing the algorithm to use multiple processing layers, composed of multiple linear and non-linear transformations.

One aspect of the present invention is to provide two analyte detection and localization approaches. The first approach is a deep learning approach and the second approach is a combination of deep learning and computer vision approaches.

(i) Deep Learning Approach. In the first approach, the disclosed analyte detection and localization workflow consists of two stages, training and prediction. We describe training and prediction stages in the following paragraphs.

(a) Training Stage

In the training stage, training data with annotation is fed into a convolutional neural network. Convolutional neural network is a specialized neural network for processing data that has a grid-like, feed forward and layered network topology. Examples of the data include time-series data, which can be thought of as a 1D grid taking samples at regular time intervals, and image data, which can be thought of as a 2D grid of pixels. Convolutional networks have been successful in practical applications. The name "convolutional neural network" indicates that the network employs a mathematical operation called convolution. Convolution is a specialized kind of linear operation. Convolutional networks are simply neural networks that use convolution in place of general matrix multiplication in at least one of their layers.

The machine learning model receives one or multiple images of samples that contain the analytes taken by the imager over the sample holding QMAX device as training data. Training data are annotated for analytes to be assayed, wherein the annotations indicate whether or not analytes are in the training data and where they locate in the image. Annotation can be done in the form of tight bounding boxes which fully contains the analyte, or center locations of analytes. In the latter case, center locations are further converted into circles covering analytes or a Gaussian kernel in a point map.

When the size of training data is large, training machine learning model presents two challenges: annotation (usually done by human) is time consuming, and the training is computationally expensive. To overcome these challenges, one can partition the training data into patches of small size, then annotate and train on these patches, or a portion of these patches. The term "machine learning" can refer to algorithms, systems and apparatus in the field of artificial intelligence that often use statistical techniques and artificial neural network trained from data without being explicitly programmed.

The annotated images are fed to the machine learning (ML) training module, and the model trainer in the machine learning module will train a ML model from the training data (annotated sample images). The input data will be fed to the model trainer in multiple iterations until certain stopping criterion is satisfied. The output of the ML training module is a ML model—a computational model that is built from a training process in the machine learning from the data that gives computer the capability to perform certain tasks (e.g. detect and classify the objects) on its own.

The trained machine learning model is applied during the predication (or inference) stage by the computer. Examples of machine learning models include ResNet, DenseNet, etc. which are also named as "deep learning models" because of the depth of the connected layers in their network structure. In certain embodiments, the Caffe library with fully convolutional network (FCN) was used for model training and predication, and other convolutional neural network architecture and library can also be used, such as TensorFlow.

The training stage generates a model that will be used in the prediction stage. The model can be repeatedly used in the prediction stage for assaying the input. Thus, the computing unit only needs access to the generated model. It does not need access to the training data, nor requiring the training stage to be run again on the computing unit.

(b) Prediction Stage

In the predication/inference stage, a detection component is applied to the input image, and an input image is fed into the predication (inference) module preloaded with a trained model generated from the training stage. The output of the prediction stage can be bounding boxes that contain the detected analytes with their center locations or a point map indicating the location of each analyte, or a heatmap that contains the information of the detected analytes.

When the output of the prediction stage is a list of bounding boxes, the number of analytes in the image of the sample for assaying is characterized by the number of detected bounding boxes. When the output of the prediction stage is a point map, the number of analytes in the image of the sample for assaying is characterized by the integration of the point map. When the output of the prediction is a heatmap, a localization component is used to identify the location and the number of detected analytes is characterized by the entries of the heatmap.

One embodiment of the localization algorithm is to sort the heatmap values into a one-dimensional ordered list, from the highest value to the lowest value. Then pick the pixel with the highest value, remove the pixel from the list, along with its neighbors. Iterate the process to pick the pixel with the highest value in the list, until all pixels are removed from the list. In the detection component using heatmap, an input image, along with the model generated from the training stage, is fed into a convolutional neural network, and the output of the detection stage is a pixel-level prediction, in the form of a heatmap. The heatmap can have the same size as the input image, or it can be a scaled down version of the input image, and it is the input to the localization component. We disclose an algorithm to localize the analyte center. The main idea is to iteratively detect local peaks from the heatmap. After the peak is localized, we calculate the local area surrounding the peak but with smaller value. We remove this region from the heatmap and find the next peak from the remaining pixels. The process is repeated only all pixels are removed from the heatmap.

In certain embodiments, the present invention provides the localization algorithm to sort the heatmap values into a one-dimensional ordered list, from the highest value to the lowest value. Then pick the pixel with the highest value, remove the pixel from the list, along with its neighbors. Iterate the process to pick the pixel with the highest value in the list, until all pixels are removed from the list.

```
Algorithm GlobalSearch (heatmap)
Input:
        heatmap
Output:
        loci
loci ← { }
sort(heatmap)
while (heatmap is not empty) {
    s ← pop(heatmap)
    D ← {disk center as s with radius R}
    heatmap = heatmap \ D // remove D from the heatmap
    add s to loci
}
```

After sorting, heatmap is a one-dimensional ordered list, where the heatmap value is ordered from the highest to the lowest. Each heatmap value is associated with its corresponding pixel coordinates. The first item in the heatmap is the one with the highest value, which is the output of the pop(heatmap) function. One disk is created, where the center is the pixel coordinate of the one with highest heatmap value. Then all heatmap values whose pixel coordinates resides inside the disk is removed from the heatmap. The algorithm repeatedly pops up the highest value in the current heatmap, removes the disk around it, till the items are removed from the heatmap.

In the ordered list heatmap, each item has the knowledge of the proceeding item, and the following item. When removing an item from the ordered list, we make the following changes:
  Assume the removing item is $x_r$, its proceeding item is $x_p$, and its following item is $x_f$.
  For the proceeding item $x_p$, re-define its following item to the following item of the removing item. Thus, the following item of $x_p$ is now $x_f$.
  For the removing item $x_r$, un-define its proceeding item and following item, which removes it from the ordered list.
  For the following item $x_f$, re-define its proceeding item to the proceeding item of the removed item. Thus, the proceeding item of $x_f$ is now $x_p$.

After all items are removed from the ordered list, the localization algorithm is complete. The number of elements in the set loci will be the count of analytes, and location information is the pixel coordinate for each s in the set loci.

Another embodiment searches local peak, which is not necessary the one with the highest heatmap value. To detect each local peak, we start from a random starting point, and search for the local maximal value. After we find the peak, we calculate the local area surrounding the peak but with smaller value. We remove this region from the heatmap and find the next peak from the remaining pixels. The process is repeated only all pixels are removed from the heatmap.

---

Algorithm LocalSearch (s, heatmap)
Input:
    s: starting location (x, y)
    heatmap
Output:
    s: location of local peak.
We only consider pixels of value > 0.

---

Algorithm Cover (s, heatmap)
Input:
    s: location of local peak.
    heatmap:
Output:
    cover: a set of pixels covered by peak:

---

This is a breadth-first-search algorithm starting from s, with one altered condition of visiting points: a neighbor p of the current location q is only added to cover if heatmap[p]>0 and heatmap[p]<=heatmap[q]. Therefore, each pixel in cover has a non-descending path leading to the local peak s.

---

Algorithm Localization (heatmap)
Input:
    heatmap
Output:
    loci
loci ←{ }
pixels ←{all pixels from heatmap}

-continued while pixels is not empty {
    s ←any pixel from pixels
    s ←LocalSearch(s, heatmap)        // s is now local peak
    probe local region of radius R surrounding s for better local peak
    r ←Cover(s, heatmap)
    pixels ← pixels \ r               // remove all pixels in cover
    add s to loci

---

(ii) Mixture of Deep Learning and Computer Vision Approaches. In the second approach, the detection and localization are realized by computer vision algorithms, and a classification is realized by deep learning algorithms, wherein the computer vision algorithms detect and locate possible candidates of analytes, and the deep learning algorithm classifies each possible candidate as a true analyte and false analyte. The location of all true analyte (along with the total count of true analytes) will be recorded as the output.

(a) Detection. The computer vision algorithm detects possible candidate based on the characteristics of analytes, including but not limited to intensity, color, size, shape, distribution, etc. A pre-processing scheme can improve the detection. Pre-processing schemes include contrast enhancement, histogram adjustment, color enhancement, de-nosing, smoothing, de-focus, etc. After pre-processing, the input image is sent to a detector. The detector tells the existing of possible candidate of analyte and gives an estimate of its location. The detection can be based on the analyte structure (such as edge detection, line detection, circle detection, etc.), the connectivity (such as blob detection, connect components, contour detection, etc.), intensity, color, shape using schemes such as adaptive thresholding, etc.

(b) Localization. After detection, the computer vision algorithm locates each possible candidate of analytes by providing its boundary or a tight bounding box containing it. This can be achieved through object segmentation algorithms, such as adaptive thresholding, background subtraction, floodfill, mean shift, watershed, etc. Very often, the localization can be combined with detection to produce the detection results along with the location of each possible candidates of analytes.

(c) Classification. The deep learning algorithms, such as convolutional neural networks, achieve start-of-the-art visual classification. We employ deep learning algorithms for classification on each possible candidate of analytes. Various convolutional neural network can be utilized for analyte classification, such as VGGNet, ResNet, MobileNet, DenseNet, etc.

Given each possible candidate of analyte, the deep learning algorithm computes through layers of neurons via convolution filters and non-linear filters to extract high-level features that differentiate analyte against non-analytes. A layer of fully convolutional network will combine high-level features into classification results, which tells whether it is a true analyte or not, or the probability of being a analyte.

G) Applications, Bio/Chemical Biomarkers, and Health Conditions

The applications of the present invention include, but not limited to, (a) the detection, purification and quantification of chemical compounds or biomolecules that correlates with the stage of certain diseases, e.g., infectious and parasitic disease, injuries, cardiovascular disease, cancer, mental disorders, neuropsychiatric disorders and organic diseases, e.g., pulmonary diseases, renal diseases, (b) the detection, purification and quantification of microorganism, e.g., virus, fungus and bacteria from environment, e.g., water, soil, or biological samples, e.g., tissues, bodily fluids, (c) the detection, quantification of chemical compounds or biological samples that pose hazard to food safety or national security, e.g. toxic waste, anthrax, (d) quantification of vital parameters in medical or physiological monitor, e.g., glucose, blood oxygen level, total blood count, (e) the detection and quantification of specific DNA or RNA from biosamples, e.g., cells, viruses, bodily fluids, (f) the sequencing and comparing of genetic sequences in DNA in the chromosomes and mitochondria for genome analysis or (g) to detect reaction products, e.g., during synthesis or purification of pharmaceuticals.

The detection can be carried out in various sample matrix, such as cells, tissues, bodily fluids, and stool. Bodily fluids of interest include but are not limited to, amniotic fluid, aqueous humour, vitreous humour, blood (e.g., whole blood, fractionated blood, plasma, serum, etc.), breast milk, cerebrospinal fluid (CSF), cerumen (earwax), chyle, chime, endolymph, perilymph, feces, gastric acid, gastric juice, lymph, mucus (including nasal drainage and phlegm), pericardial fluid, peritoneal fluid, pleural fluid, pus, rheum, saliva, sebum (skin oil), semen, sputum, sweat, synovial fluid, tears, vomit, urine and exhaled condensate. In some embodiments, the sample comprises a human body fluid. In some embodiments, the sample comprises at least one of cells, tissues, bodily fluids, stool, amniotic fluid, aqueous humour, vitreous humour, blood, whole blood, fractionated blood, plasma, serum, breast milk, cerebrospinal fluid, cerumen, chyle, chime, endolymph, perilymph, feces, gastric acid, gastric juice, lymph, mucus, nasal drainage, phlegm, pericardial fluid, peritoneal fluid, pleural fluid, pus, rheum, saliva, sebum, semen, sputum, sweat, synovial fluid, tears, vomit, urine, and exhaled condensate.

In embodiments, the sample is at least one of a biological sample, an environmental sample, and a biochemical sample.

The devices, systems and the methods in the present invention find use in a variety of different applications in various fields, where determination of the presence or absence, and/or quantification of one or more analytes in a sample are desired. For example, the subject method finds use in the detection of proteins, peptides, nucleic acids, synthetic compounds, inorganic compounds, and the like. The various fields include, but are not limited to, human, veterinary, agriculture, foods, environments, drug testing, and others.

In certain embodiments, the subject method finds use in the detection of nucleic acids, proteins, or other biomolecules in a sample. The methods can include the detection of a set of biomarkers, e.g., two or more distinct protein or nucleic acid biomarkers, in a sample. For example, the methods can be used in the rapid, clinical detection of two or more disease biomarkers in a biological sample, e.g., as can be employed in the diagnosis of a disease condition in a subject, or in the ongoing management or treatment of a disease condition in a subject, etc. As described above, communication to a physician or other health-care provider can better ensure that the physician or other health-care provider is made aware of, and cognizant of, possible concerns and can thus be more likely to take appropriate action.

The applications of the devices, systems and methods in the present inventions of employing a CROF device include, but are not limited to, (a) the detection, purification and quantification of chemical compounds or biomolecules that correlates with the stage of certain diseases, e.g., infectious and parasitic disease, injuries, cardiovascular disease, cancer, mental disorders, neuropsychiatric disorders and organic diseases, e.g., pulmonary diseases, renal diseases, (b) the detection, purification and quantification of microorganism, e.g., virus, fungus and bacteria from environment, e.g., water, soil, or biological samples, e.g., tissues, bodily fluids, (c) the detection, quantification of chemical compounds or biological samples that pose hazard to food safety or national security, e.g. toxic waste, anthrax, (d) quantification of vital parameters in medical or physiological monitor, e.g., glucose, blood oxygen level, total blood count, (e) the detection and quantification of specific DNA or RNA from biosamples, e.g., cells, viruses, bodily fluids, (f) the sequencing and comparing of genetic sequences in DNA in the chromosomes and mitochondria for genome analysis or (g) to detect reaction products, e.g., during synthesis or purification of pharmaceuticals. Some of the specific applications of the devices, systems and methods in the present invention are described now in further detail.

The applications of the present invention include, but not limited to, (a) the detection, purification and quantification of chemical compounds or biomolecules that correlates with the stage of certain diseases, e.g., infectious and parasitic disease, injuries, cardiovascular disease, cancer, mental disorders, neuropsychiatric disorders and organic diseases, e.g., pulmonary diseases, renal diseases, (b) the detection, purification and quantification of microorganism, e.g., virus, fungus and bacteria from environment, e.g., water, soil, or biological samples, e.g., tissues, bodily fluids, (c) the detection, quantification of chemical compounds or biological samples that pose hazard to food safety or national security, e.g. toxic waste, anthrax, (d) quantification of vital parameters in medical or physiological monitor, e.g., glucose, blood oxygen level, total blood count, (e) the detection and quantification of specific DNA or RNA from biosamples, e.g., cells, viruses, bodily fluids, (f) the sequencing and comparing of genetic sequences in DNA in the chromosomes and mitochondria for genome analysis or (g) to detect reaction products, e.g., during synthesis or purification of pharmaceuticals.

An implementation of the devices, systems and methods in the present invention can include a) obtaining a sample, b) applying the sample to CROF device containing a capture agent that binds to an analyte of interest, under conditions suitable for binding of the analyte in a sample to the capture agent, c) washing the CROF device, and d) reading the CROF device, thereby obtaining a measurement of the amount of the analyte in the sample. In some embodiments, the analyte can be a biomarker, an environmental marker, or a foodstuff marker. The sample in some instances is a liquid sample, and can be a diagnostic sample (such as saliva, serum, blood, sputum, urine, sweat, lacrima, semen, or mucus); an environmental sample obtained from a river, ocean, lake, rain, snow, sewage, sewage processing runoff, agricultural runoff, industrial runoff, tap water or drinking water; or a foodstuff sample obtained from tap water, drinking water, prepared food, processed food or raw food.

In any embodiment, the CROF device can be placed in a microfluidic device and the applying step b) can include applying a sample to a microfluidic device comprising the CROF device.

In any embodiment, the reading step d) can include detecting a fluorescence or luminescence signal from the CROF device.

In any embodiment, the reading step d) can include reading the CROF device with a handheld device configured to read the CROF device. The handheld device can be a mobile phone, e.g., a smart phone.

In any embodiment, the CROF device can include a labeling agent that can bind to an analyte-capture agent complex on the CROF device.

In any embodiment, the devices, systems and methods in the present invention can further include, between steps c) and d), the steps of applying to the CROF device a labeling agent that binds to an analyte-capture agent complex on the CROF device, and washing the CROF device.

In any embodiment, the reading step d) can include reading an identifier for the CROF device. The identifier can be an optical barcode, a radio frequency ID tag, or combinations thereof.

In any embodiment, the devices, systems and methods in the present invention can further include applying a control sample to a control CROF device containing a capture agent that binds to the analyte, wherein the control sample includes a known detectable amount of the analyte, and reading the control CROF device, thereby obtaining a control measurement for the known detectable amount of the analyte in a sample.

In any embodiment, the sample can be a diagnostic sample obtained from a subject, the analyte can be a biomarker, and the measured amount of the analyte in the sample can be diagnostic of a disease or a condition.

In any embodiment, the devices, systems and methods in the present invention can further include receiving or providing to the subject a report that indicates the measured amount of the biomarker and a range of measured values for the biomarker in an individual free of or at low risk of having the disease or condition, wherein the measured amount of the biomarker relative to the range of measured values is diagnostic of a disease or condition.

In any embodiment, the devices, systems and methods in the present invention can further include diagnosing the subject based on information including the measured amount of the biomarker in the sample. In some cases, the diagnosing step includes sending data containing the measured amount of the biomarker to a remote location and receiving a diagnosis based on information including the measurement from the remote location.

In any embodiment, the applying step b) can include isolating miRNA from the sample to generate an isolated miRNA sample, and applying the isolated miRNA sample to the disk-coupled dots-on-pillar antenna (CROF device) array.

In any embodiment, the method can include receiving or providing a report that indicates the safety or harmfulness for a subject to be exposed to the environment from which the sample was obtained.

In any embodiment, the method can include sending data containing the measured amount of the environmental marker to a remote location and receiving a report that indicates the safety or harmfulness for a subject to be exposed to the environment from which the sample was obtained.

In any embodiment, the CROF device array can include a plurality of capture agents that each binds to an environmental marker, and wherein the reading step d) can include obtaining a measure of the amount of the plurality of environmental markers in the sample. In any embodiment, the sample can be a foodstuff sample, wherein the analyte can be a foodstuff marker, and wherein the amount of the foodstuff marker in the sample can correlate with safety of the foodstuff for consumption.

In any embodiment, the method can include receiving or providing a report that indicates the safety or harmfulness for a subject to consume the foodstuff from which the sample is obtained.

In any embodiment, the method can include sending data containing the measured amount of the foodstuff marker to a remote location and receiving a report that indicates the safety or harmfulness for a subject to consume the foodstuff from which the sample is obtained.

In any embodiment, the CROF device array can include a plurality of capture agents that each binds to a foodstuff marker, wherein the obtaining can include obtaining a measure of the amount of the plurality of foodstuff markers in the sample, and wherein the amount of the plurality of foodstuff marker in the sample can correlate with safety of the foodstuff for consumption.

Also provided herein are kits that find use in practicing the devices, systems and methods in the present invention.

The amount of sample can be about a drop of a sample. The amount of sample can be the amount collected from a pricked finger or fingerstick. The amount of sample can be the amount collected from a microneedle or a venous draw.

A sample can be used without further processing after obtaining it from the source, or can be processed, e.g., to enrich for an analyte of interest, remove large particulate matter, dissolve or resuspend a solid sample, etc.

Any suitable method of applying a sample to the CROF device can be employed. Suitable methods can include using a pipet, dropper, syringe, etc. In certain embodiments, when the CROF device is located on a support in a dipstick format, as described below, the sample can be applied to the CROF device by dipping a sample-receiving area of the dipstick into the sample.

A sample can be collected at one time, or at a plurality of times. Samples collected over time can be aggregated and/or processed (by applying to a CROF device and obtaining a measurement of the amount of analyte in the sample, as described herein) individually. In some instances, measurements obtained over time can be aggregated and can be useful for longitudinal analysis over time to facilitate screening, diagnosis, treatment, and/or disease prevention.

Washing the CROF device to remove unbound sample components can be done in any convenient manner, as described above. In certain embodiments, the surface of the CROF device is washed using binding buffer to remove unbound sample components. Detectable labeling of the analyte can be done by any convenient method. The analyte can be labeled directly or indirectly. In direct labeling, the analyte in the sample is labeled before the sample is applied to the CROF device. In indirect labeling, an unlabeled analyte in a sample is labeled after the sample is applied to the CROF device to capture the unlabeled analyte, as described below.

The samples from a subject, the health of a subject, and other applications of the present invention are further described below. Exemplary samples, health conditions, and application are also disclosed in, e.g., U.S. Pub. Nos. 2014/0154668 and 2014/0045209, which are hereby incorporated by reference.

The present inventions find use in a variety of applications, where such applications are generally analyte detection applications in which the presence of a particular analyte in a given sample is detected at least qualitatively, if not quantitatively. Protocols for carrying out analyte detection assays are well known to those of skill in the art and need not be described in great detail here. Generally, the sample suspected of comprising an analyte of interest is contacted with the surface of a subject nanosensor under conditions sufficient for the analyte to bind to its respective capture agent that is tethered to the sensor. The capture agent has highly specific affinity for the targeted molecules of interest. This affinity can be antigen-antibody reaction where antibodies bind to specific epitope on the antigen, or a DNA/RNA or DNA/RNA hybridization reaction that is sequence-specific between two or more complementary strands of nucleic acids. Thus, if the analyte of interest is present in the sample, it likely binds to the sensor at the site of the capture agent and a complex is formed on the sensor surface. Namely, the captured analytes are immobilized at the sensor surface. After removing the unbounded analytes, the presence of this binding complex on the surface of the sensor (i.e. the immobilized analytes of interest) is then detected, e.g., using a labeled secondary capture agent.

Specific analyte detection applications of interest include hybridization assays in which the nucleic acid capture agents are employed and protein binding assays in which polypeptides, e.g., antibodies, are employed. In these assays, a sample is first prepared and following sample preparation, the sample is contacted with a subject nanosensor under specific binding conditions, whereby complexes are formed between target nucleic acids or polypeptides (or other molecules) that are complementary to capture agents attached to the sensor surface.

In one embodiment, the capture oligonucleotide is synthesized single strand DNA of 20-100 bases length, that is thiolated at one end. These molecules are are immobilized on the nanodevices' surface to capture the targeted single-strand DNA (which can be at least 50 bp length) that has a sequence that is complementary to the immobilized capture DNA. After the hybridization reaction, a detection single strand DNA (which can be of 20-100 bp in length) whose sequence are complementary to the targeted DNA's unoccupied nucleic acid is added to hybridize with the target. The detection DNA has its one end conjugated to a fluorescence label, whose emission wavelength are within the plasmonic resonance of the nanodevice. Therefore by detecting the fluorescence emission emanate from the nanodevices' surface, the targeted single strand DNA can be accurately detected and quantified. The length for capture and detection DNA determine the melting temperature (nucleotide strands will separate above melting temperature), the extent of misparing (the longer the strand, the lower the misparing).

One of the concerns of choosing the length for complementary binding depends on the needs to minimize misparing while keeping the melting temperature as high as possible. In addition, the total length of the hybridization length is determined in order to achieve optimum signal amplification.

A subject sensor can be employed in a method of diagnosing a disease or condition, comprising: (a) obtaining a liquid sample from a patient suspected of having the disease or condition, (b) contacting the sample with a subject nanosensor, wherein the capture agent of the nanosensor specifically binds to a biomarker for the disease and wherein the contacting is done under conditions suitable for specific binding of the biomarker with the capture agent; (c) removing any biomarker that is not bound to the capture agent; and (d) reading a light signal from biomarker that remain bound to the nanosensor, wherein a light signal indicates that the patient has the disease or condition, wherein the method further comprises labeling the biomarker with a light-emitting label, either prior to or after it is bound to the capture agent. As will be described in greater detail below, the patient can suspected of having cancer and the antibody binds to a cancer biomarker. In other embodiments, the patient is suspected of having a neurological disorder and the antibody binds to a biomarker for the neurological disorder.

The applications of the subject sensor include, but not limited to, (a) the detection, purification and quantification of chemical compounds or biomolecules that correlates with the stage of certain diseases, e.g., infectious and parasitic disease, injuries, cardiovascular disease, cancer, mental disorders, neuropsychiatric disorders and organic diseases, e.g., pulmonary diseases, renal diseases, (b) the detection, purification and quantification of microorganism, e.g., virus, fungus and bacteria from environment, e.g., water, soil, or biological samples, e.g., tissues, bodily fluids, (c) the detection, quantification of chemical compounds or biological samples that pose hazard to food safety or national security, e.g. toxic waste, anthrax, (d) quantification of vital parameters in medical or physiological monitor, e.g., glucose, blood oxygen level, total blood count, (e) the detection and quantification of specific DNA or RNA from biosamples, e.g., cells, viruses, bodily fluids, (f) the sequencing and comparing of genetic sequences in DNA in the chromosomes and mitochondria for genome analysis or (g) to detect reaction products, e.g., during synthesis or purification of pharmaceuticals.

The detection can be carried out in various sample matrix, such as cells, tissues, bodily fluids, and stool. Bodily fluids of interest include but are not limited to, amniotic fluid, aqueous humour, vitreous humour, blood (e.g., whole blood, fractionated blood, plasma, serum, etc.), breast milk, cerebrospinal fluid (CSF), cerumen (earwax), chyle, chime, endolymph, perilymph, feces, gastric acid, gastric juice, lymph, mucus (including nasal drainage and phlegm), pericardial fluid, peritoneal fluid, pleural fluid, pus, rheum, saliva, sebum (skin oil), semen, sputum, sweat, synovial fluid, tears, vomit, urine and exhaled condensate.

In some embodiments, a subject biosensor can be used diagnose a pathogen infection by detecting a target nucleic acid from a pathogen in a sample. The target nucleic acid can be, for example, from a virus that is selected from the group comprising human immunodeficiency virus 1 and 2 (HIV-1 and HIV-2), human T-cell leukaemia virus and 2 (HTLV-1 and HTLV-2), respiratory syncytial virus (RSV), adenovirus, hepatitis B virus (HBV), hepatitis C virus (HCV), Epstein-Barr virus (EBV), human papillomavirus (HPV), varicella zoster virus (VZV), cytomegalovirus (CMV), herpes-simplex virus 1 and 2 (HSV-1 and HSV-2), human herpesvirus 8 (HHV-8, also known as Kaposi sarcoma herpesvirus) and flaviviruses, including yellow fever virus, dengue virus, Japanese encephalitis virus, West Nile virus and Ebola virus. The present invention is not, however, limited to the detection of nucleic acid, e.g., DNA or RNA, sequences from the aforementioned viruses, but can be applied without any problem to other pathogens important in veterinary and/or human medicine.

Human papillomaviruses (HPV) are further subdivided on the basis of their DNA sequence homology into more than 70 different types. These types cause different diseases. HPV types 1, 2, 3, 4, 7, 10 and 26-29 cause benign warts. HPV types 5, 8, 9, 12, 14, 15, 17 and 19-25 and 46-50 cause lesions in patients with a weakened immune system. Types 6, 11, 34, 39, 41-44 and 51-55 cause benign acuminate warts on the mucosae of the genital region and of the respiratory tract. HPV types 16 and 18 are of special medical interest, as they cause epithelial dysplasias of the genital mucosa and are associated with a high proportion of the invasive carcinomas of the cervix, vagina, vulva and anal canal. Integration of the DNA of the human papillomavirus is considered to be decisive in the carcinogenesis of cervical cancer. Human papillomaviruses can be detected for example from the DNA sequence of their capsid proteins L1 and L2. Accordingly, the method of the present invention is especially suitable for the detection of DNA sequences of HPV types 16 and/or 18 in tissue samples, for assessing the risk of development of carcinoma.

In some cases, the nanosensor can be employed to detect a biomarker that is present at a low concentration. For example, the nanosensor can be used to detect cancer antigens in a readily accessible bodily fluids (e.g., blood, saliva, urine, tears, etc.), to detect biomarkers for tissue-specific diseases in a readily accessible bodily fluid (e.g., a biomarkers for a neurological disorder (e.g., Alzheimer's antigens)), to detect infections (particularly detection of low titer latent viruses, e.g., HIV), to detect fetal antigens in maternal blood, and for detection of exogenous compounds (e.g., drugs or pollutants) in a subject's bloodstream, for example.

The following table provides a list of protein biomarkers that can be detected using the subject nanosensor (when used in conjunction with an appropriate monoclonal antibody), and their associated diseases. One potential source of the biomarker (e.g., "CSF"; cerebrospinal fluid) is also indicated in the table. In many cases, the subject biosensor can detect those biomarkers in a different bodily fluid to that indicated. For example, biomarkers that are found in CSF can be identified in urine, blood or saliva.

H) Utility

The subject method finds use in a variety of different applications where determination of the presence or absence, and/or quantification of one or more analytes in a sample are desired. For example, the subject method finds use in the detection of proteins, peptides, nucleic acids, synthetic compounds, inorganic compounds, and the like.

In certain embodiments, the subject method finds use in the detection of nucleic acids, proteins, or other biomolecules in a sample. The methods can include the detection of a set of biomarkers, e.g., two or more distinct protein or nucleic acid biomarkers, in a sample. For example, the methods can be used in the rapid, clinical detection of two or more disease biomarkers in a biological sample, e.g., as can be employed in the diagnosis of a disease condition in a subject, or in the ongoing management or treatment of a disease condition in a subject, etc. As described above, communication to a physician or other health-care provider can better ensure that the physician or other health-care provider is made aware of, and cognizant of, possible concerns and can thus be more likely to take appropriate action.

The applications of the devices, systems and methods in the present invention of employing a CROF device include, but are not limited to, (a) the detection, purification and quantification of chemical compounds or biomolecules that correlates with the stage of certain diseases, e.g., infectious and parasitic disease, injuries, cardiovascular disease, cancer, mental disorders, neuropsychiatric disorders and organic diseases, e.g., pulmonary diseases, renal diseases, (b) the detection, purification and quantification of microorganism, e.g., virus, fungus and bacteria from environment, e.g., water, soil, or biological samples, e.g., tissues, bodily fluids, (c) the detection, quantification of chemical compounds or biological samples that pose hazard to food safety or national security, e.g. toxic waste, anthrax, (d) quantification of vital parameters in medical or physiological monitor, e.g., glucose, blood oxygen level, total blood count, (e) the detection and quantification of specific DNA or RNA from biosamples, e.g., cells, viruses, bodily fluids, (f) the sequencing and comparing of genetic sequences in DNA in the chromosomes and mitochondria for genome analysis or (g) to detect reaction products, e.g., during synthesis or purification of pharmaceuticals. Some of the specific applications of the devices, systems and methods in the present invention are described now in further detail.

I) Diagnostic Method

In certain embodiments, the subject method finds use in detecting biomarkers. In some embodiments, the devices, systems and methods in the present invention of using CROF are used to detect the presence or absence of particular biomarkers, as well as an increase or decrease in the concentration of particular biomarkers in blood, plasma, serum, or other bodily fluids or excretions, such as but not limited to urine, blood, serum, plasma, saliva, semen, prostatic fluid, nipple aspirate fluid, lachrymal fluid, perspiration, feces, cheek swabs, cerebrospinal fluid, cell lysate samples, amniotic fluid, gastrointestinal fluid, biopsy tissue, and the like. Thus, the sample, e.g. a diagnostic sample, can include various fluid or solid samples.

In some instances, the sample can be a bodily fluid sample from a subject who is to be diagnosed. In some instances, solid or semi-solid samples can be provided. The sample can include tissues and/or cells collected from the subject. The sample can be a biological sample. Examples of biological samples can include but are not limited to, blood, serum, plasma, a nasal swab, a nasopharyngeal wash, saliva, urine, gastric fluid, spinal fluid, tears, stool, mucus, sweat, earwax, oil, a glandular secretion, cerebral spinal fluid, tissue, semen, vaginal fluid, interstitial fluids derived from tumorous tissue, ocular fluids, spinal fluid, a throat swab, breath, hair, finger nails, skin, biopsy, placental fluid, amniotic fluid, cord blood, lymphatic fluids, cavity fluids, sputum, pus, microbiota, meconium, breast milk, exhaled condensate and/or other excretions. The samples can include nasopharyngeal wash. Nasal swabs, throat swabs, stool samples, hair, finger nail, ear wax, breath, and other solid, semi-solid, or gaseous samples can be processed in an extraction buffer, e.g., for a fixed or variable amount of time, prior to their analysis. The extraction buffer or an aliquot thereof can then be processed similarly to other fluid samples if desired. Examples of tissue samples of the subject can include but are not limited to, connective tissue, muscle tissue, nervous tissue, epithelial tissue, cartilage, cancerous sample, or bone.

In some instances, the subject from which a diagnostic sample is obtained can be a healthy individual, or can be an individual at least suspected of having a disease or a health condition. In some instances, the subject can be a patient.

In certain embodiments, the CROF device includes a capture agent configured to specifically bind a biomarker in a sample provided by the subject. In certain embodiments, the biomarker can be a protein. In certain embodiments, the biomarker protein is specifically bound by an antibody capture agent present in the CROF device. In certain embodiments, the biomarker is an antibody specifically bound by an antigen capture agent present in the CROF device. In certain embodiments, the biomarker is a nucleic acid specifically bound by a nucleic acid capture agent that is complementary to one or both strands of a double-stranded nucleic acid biomarker, or complementary to a single-stranded biomarker. In certain embodiments, the biomarker is a nucleic acid specifically bound by a nucleic acid binding protein. In certain embodiments, the biomarker is specifically bound by an aptamer.

The presence or absence of a biomarker or significant changes in the concentration of a biomarker can be used to diagnose disease risk, presence of disease in an individual, or to tailor treatments for the disease in an individual. For example, the presence of a particular biomarker or panel of biomarkers can influence the choices of drug treatment or administration regimes given to an individual. In evaluating potential drug therapies, a biomarker can be used as a surrogate for a natural endpoint such as survival or irreversible morbidity. If a treatment alters the biomarker, which has a direct connection to improved health, the biomarker can serve as a surrogate endpoint for evaluating the clinical benefit of a particular treatment or administration regime. Thus, personalized diagnosis and treatment based on the particular biomarkers or panel of biomarkers detected in an individual are facilitated by the subject method. Furthermore, the early detection of biomarkers associated with diseases is facilitated by the high sensitivity of the devices, systems and methods in the present invention, as described above. Due to the capability of detecting multiple biomarkers with a mobile device, such as a smartphone, combined with sensitivity, scalability, and ease of use, the presently disclosed method finds use in portable and point-of-care or near-patient molecular diagnostics.

In certain embodiments, the subject method finds use in detecting biomarkers for a disease or disease state. In certain instances, the subject method finds use in detecting biomarkers for the characterization of cell signaling pathways and intracellular communication for drug discovery and vaccine development. For example, the subject method can be used to detect and/or quantify the amount of biomarkers in diseased, healthy or benign samples. In certain embodiments, the subject method finds use in detecting biomarkers for an infectious disease or disease state. In some cases, the biomarkers can be molecular biomarkers, such as but not limited to proteins, nucleic acids, carbohydrates, small molecules, and the like.

The subject method find use in diagnostic assays, such as, but not limited to, the following: detecting and/or quantifying biomarkers, as described above; screening assays, where samples are tested at regular intervals for asymptomatic subjects; prognostic assays, where the presence and or quantity of a biomarker is used to predict a likely disease course; stratification assays, where a subject's response to different drug treatments can be predicted; efficacy assays, where the efficacy of a drug treatment is monitored; and the like.

In some embodiments, a subject biosensor can be used diagnose a pathogen infection by detecting a target nucleic acid from a pathogen in a sample. The target nucleic acid can be, for example, from a virus that is selected from the group comprising human immunodeficiency virus 1 and 2 (HIV-1 and HIV-2), human T-cell leukaemia virus and 2 (HTLV-1 and HTLV-2), respiratory syncytial virus (RSV), adenovirus, hepatitis B virus (HBV), hepatitis C virus (HCV), Epstein-Barr virus (EBV), human papillomavirus (HPV), varicella zoster virus (VZV), cytomegalovirus (CMV), herpes-simplex virus 1 and 2 (HSV-1 and HSV-2), human herpesvirus 8 (HHV-8, also known as Kaposi sarcoma herpesvirus) and flaviviruses, including yellow fever virus, dengue virus, Japanese encephalitis virus, West Nile virus and Ebola virus. The present invention is not, however, limited to the detection of nucleic acid, e.g., DNA or RNA, sequences from the aforementioned viruses, but can be applied without any problem to other pathogens important in veterinary and/or human medicine.

Human papillomaviruses (HPV) are further subdivided on the basis of their DNA sequence homology into more than 70 different types. These types cause different diseases. HPV types 1, 2, 3, 4, 7, 10 and 26-29 cause benign warts. HPV types 5, 8, 9, 12, 14, 15, 17 and 19-25 and 46-50 cause lesions in patients with a weakened immune system. Types 6, 11, 34, 39, 41-44 and 51-55 cause benign acuminate warts on the mucosae of the genital region and of the respiratory tract. HPV types 16 and 18 are of special medical interest, as they cause epithelial dysplasias of the genital mucosa and are associated with a high proportion of the invasive carcinomas of the cervix, vagina, vulva and anal canal. Integration of the DNA of the human papillomavirus is considered to be decisive in the carcinogenesis of cervical cancer. Human papillomaviruses can be detected for example from the DNA sequence of their capsid proteins L1 and L2. Accordingly, the method of the present invention is especially suitable for the detection of DNA sequences of HPV types 16 and/or 18 in tissue samples, for assessing the risk of development of carcinoma.

Other pathogens that can be detected in a diagnostic sample using the devices, systems and methods in the present invention include, but are not limited to: Varicella zoster, *Staphylococcus epidermidis, Escherichia coli*, methicillin-resistant *Staphylococcus aureus* (MSRA), *Staphylococcus aureus, Staphylococcus hominis, Enterococcus faecalis, Pseudomonas aeruginosa, Staphylococcus capitis, Staphylococcus wameri, Klebsiella pneumoniae, Haemophilus influenzae, Staphylococcus simulans, Streptococcus pneumoniae* and *Candida albicans*; gonorrhea (*Neisseria gorrhoeae*), syphilis (*Treponena pallidum*), clamydia (*Clamyda tracomitis*), nongonococcal urethritis (*Ureaplasm urealyticum*), chancroid (*Haemophilus ducreyi*), trichomoniasis (*Trichomonas vaginalis*); *Pseudomonas aeruginosa*, methicillin-resistant *Staphlococccus aureus* (MSRA), *Klebsiella pneumoniae, Haemophilis influenzae, Staphylococcus aureus, Stenotrophomonas maltophilia, Haemophilis parainfluenzae, Escherichia coli, Enterococcus faecalis, Serratia marcescens, Haemophilis parahaemolyticus, Enterococcus cloacae, Candida albicans, Moraxiella catarrhalis, Streptococcus pneumoniae, Citrobacter freundii, Enterococcus faecium, Klebsella oxytoca, Pseudomonas fluorscens, Neiseria meningitidis, Streptococcus pyogenes, Pneumocystis Klebsiella pneumoniae Legionella pneumophila, Mycoplasma pneumoniae*, and *Mycobacterium tuberculosis*, etc.

In some cases, the CROF device can be employed to detect a biomarker that is present at a low concentration. For example, the CROF device can be used to detect cancer antigens in a readily accessible bodily fluids (e.g., blood, saliva, urine, tears, etc.), to detect biomarkers for tissue-specific diseases in a readily accessible bodily fluid (e.g., a biomarkers for a neurological disorder (e.g., Alzheimer's antigens)), to detect infections (particularly detection of low titer latent viruses, e.g., HIV), to detect fetal antigens in maternal blood, and for detection of exogenous compounds (e.g., drugs or pollutants) in a subject's bloodstream, for example.

One potential source of the biomarker (e.g., "CSF"; cerebrospinal fluid) is also indicated in the table. In many cases, the subject biosensor can detect those biomarkers in a different bodily fluid to that indicated. For example, biomarkers that are found in CSF can be identified in urine, blood or saliva. It will also be clear to one with ordinary skill in the art that the subject CROF devices can be configured to capture and detect many more biomarkers known in the art that are diagnostic of a disease or health condition.

A biomarker can be a protein or a nucleic acid (e.g., mRNA) biomarker, unless specified otherwise. The diagnosis can be associated with an increase or a decrease in the level of a biomarker in the sample, unless specified otherwise. Lists of biomarkers, the diseases that they can be used to diagnose, and the sample in which the biomarkers can be detected are described in Tables 1 and 2 of U.S. provisional application Ser. No. 62/234,538, filed on Sep. 29, 2015, which application is incorporated by reference herein.

In some instances, the devices, systems and methods in the present invention is used to inform the subject from whom the sample is derived about a health condition thereof. Health conditions that can be diagnosed or measured by the devices, systems and methods in the present invention, device and system include, but are not limited to: chemical balance; nutritional health; exercise; fatigue; sleep; stress; prediabetes; allergies; aging; exposure to environmental toxins, pesticides, herbicides, synthetic hormone analogs; pregnancy; menopause; and andropause. Table 3 of U.S. provisional application Ser. No. 62/234,538, filed on Sep. 29, 2015, which application is incorporated by reference herein, provides a list of biomarker that can be detected using the present CROF device (when used in conjunction with an appropriate monoclonal antibody, nucleic acid, or other capture agent), and their associated health conditions.

J) Kits

Aspects of the present disclosure include a kit that find use in performing the devices, systems and methods in the present invention, as described above. In certain embodiments, the kit includes instructions for practicing the subject methods using a hand held device, e.g., a mobile phone. These instructions can be present in the subject kits in a variety of forms, one or more of which can be present in the kit. One form in which these instructions can be present is as printed information on a suitable medium or substrate, e.g., a piece or pieces of paper on which the information is printed, in the packaging of the kit, in a package insert, etc. Another means would be a computer readable medium, e.g., diskette, CD, DVD, Blu-Ray, computer-readable memory, etc., on which the information has been recorded or stored. Yet another means that can be present is a website address which can be used via the Internet to access the information at a removed site. The kit can further include a software for implementing a method for measuring an analyte on a device, as described herein, provided on a computer readable medium. Any convenient means can be present in the kits.

In some embodiments, the kit includes a detection agent that includes a detectable label, e.g. a fluorescently labeled antibody or oligonucleotide that binds specifically to an analyte of interest, for use in labeling the analyte of interest. The detection agent can be provided in a separate container as the CROF device, or can be provided in the CROF device. In some embodiments, the kit includes a control sample that includes a known detectable amount of an analyte that is to be detected in the sample. The control sample can be provided in a container, and can be in solution at a known concentration, or can be provided in dry form, e.g., lyophilized or freeze dried. The kit can also include buffers for use in dissolving the control sample, if it is provided in dry form.

Related Documents

The present invention includes a variety of embodiments, which can be combined in multiple ways as long as the various components do not contradict one another. The embodiments should be regarded as a single invention file: each filing has other filing as the references and is also referenced in its entirety and for all purpose, rather than as a discrete independent. These embodiments include not only the disclosures in the current file, but also the documents that are herein referenced, incorporated, or to which priority is claimed.

(1) Definitions

The terms used in describing the devices, systems, and methods herein disclosed are defined in the current application, or in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

The terms "CROF Card (or card)", "COF Card", "QMAX-Card", "Q-Card", "CROF device", "COF device", "QMAX-device", "CROF plates", "COF plates", and "QMAX-plates" are interchangeable, except that in some embodiments, the COF card does not comprise spacers; and the terms refer to a device that comprises a first plate and a second plate that are movable relative to each other into different configurations (including an open configuration and a closed configuration), and that comprises spacers (except some embodiments of the COF card) that regulate the spacing between the plates. The term "X-plate" refers to one of the two plates in a CROF card, wherein the spacers are fixed to this plate. More descriptions of the COF Card, CROF Card, and X-plate are given in the provisional application Ser. Nos. 62/456,065, filed on Feb. 7, 2017, which is incorporated herein in its entirety for all purposes.

(2) Q-Card, Spacer and Uniform Sample Thickness

The devices, systems, and methods herein disclosed can include or use Q-cards, spacers, and uniform sample thickness embodiments for sample detection, analysis, and quantification. In some embodiments, the Q-card comprises spacers, which help to render at least part of the sample into a layer of high uniformity. The structure, material, function, variation and dimension of the spacers, as well as the uniformity of the spacers and the sample layer, are herein disclosed, or listed, described, and summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456, 504, which was filed on Feb. 8, 2017, all of which applications are incorporated herein in their entireties for all purposes.

(3) Hinges, Opening Notches, Recessed Edge and Sliders

The devices, systems, and methods herein disclosed can include or use Q-cards for sample detection, analysis, and quantification. In some embodiments, the Q-card comprises hinges, notches, recesses, and sliders, which help to facilitate the manipulation of the Q card and the measurement of the samples. The structure, material, function, variation and dimension of the hinges, notches, recesses, and sliders are herein disclosed, or listed, described, and summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

(4) Q-Card, Sliders, and Smartphone Detection System

The devices, systems, and methods herein disclosed can include or use Q-cards for sample detection, analysis, and quantification. In some embodiments, the Q-cards are used together with sliders that allow the card to be read by a smartphone detection system. The structure, material, function, variation, dimension and connection of the Q-card, the sliders, and the smartphone detection system are herein disclosed, or listed, described, and summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

(5) Detection Methods

The devices, systems, and methods herein disclosed can include or be used in various types of detection methods. The detection methods are herein disclosed, or listed, described, and summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

(6) Labels, Capture Agent and Detection Agent

The devices, systems, and methods herein disclosed can employ various types of labels, capture agents, and detection agents that are used for analytes detection. The labels are herein disclosed, or listed, described, and summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

(7) Analytes

The devices, systems, and methods herein disclosed can be applied to manipulation and detection of various types of analytes (including biomarkers). The analytes and are herein disclosed, or listed, described, and summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

(8) Applications (Field and Samples)

The devices, systems, and methods herein disclosed can be used for various applications (fields and samples). The applications are herein disclosed, or listed, described, and summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

(9) Cloud

The devices, systems, and methods herein disclosed can employ cloud technology for data transfer, storage, and/or analysis. The related cloud technologies are herein disclosed, or listed, described, and summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

Other Embodiments

Further examples of inventive subject matter according to the present disclosure are described in the following enumerated paragraphs.

It must be noted that, as used herein and in the appended claims, the singular forms "a", "an", and "the" include plural referents unless the context clearly dictates otherwise, e.g., when the word "single" is used. For example, reference to "an analyte" includes a single analyte and multiple analytes, reference to "a capture agent" includes a single capture agent and multiple capture agents, reference to "a detection agent" includes a single detection agent and multiple detection agents, and reference to "an agent" includes a single agent and multiple agents.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. The term "about" or "approximately" can mean within an acceptable error range for the particular value as determined by one of ordinary skill in the art, which will depend in part on how the value is measured or determined, i.e. the limitations of the measurement system. For example, "about" can mean within 1 or more than 1 standard deviation, per the practice in the art. Alternatively, "about" can mean a range of up to 20%, up to 10%, up to 5%, or up to 1% of a given value. Alternatively, particularly with respect to biological systems or processes, the term can mean within an order of magnitude, within 5-fold, and more preferably within 2-fold, of a value. Where particular values are described in the application and claims, unless otherwise stated the term "about" meaning within an acceptable error range for the particular value should be assumed. The term "about" has the meaning as commonly understood by one of ordinary skill in the art. In some embodiments, the term "about" refers to ±10%. In some embodiments, the term "about" refers to ±5%.

As used herein, the terms "adapted" and "configured" mean that the element, component, or other subject matter is designed and/or intended to perform a given function. Thus, the use of the terms "adapted" and "configured" should not be construed to mean that a given element, component, or other subject matter is simply "capable of" performing a given function. Similarly, subject matter that is recited as being configured to perform a particular function can additionally or alternatively be described as being operative to perform that function.

As used herein, the phrase, "for example," the phrase, "as an example," and/or simply the terms "example" and "exemplary" when used with reference to one or more components, features, details, structures, embodiments, and/or methods according to the present disclosure, are intended to convey that the described component, feature, detail, structure, embodiment, and/or method is an illustrative, non-exclusive example of components, features, details, structures, embodiments, and/or methods according to the present disclosure. Thus, the described component, feature, detail, structure, embodiment, and/or method is not intended to be limiting, required, or exclusive/exhaustive; and other components, features, details, structures, embodiments, and/or methods, including structurally and/or functionally similar and/or equivalent components, features, details, structures, embodiments, and/or methods, are also within the scope of the present disclosure.

As used herein, the phrases "at least one of" and "one or more of," in reference to a list of more than one entity, means any one or more of the entity in the list of entity, and is not limited to at least one of each and every entity specifically listed within the list of entity. For example, "at least one of A and B" (or, equivalently, "at least one of A or B," or, equivalently, "at least one of A and/or B") can refer to A alone, B alone, or the combination of A and B.

As used herein, the term "and/or" placed between a first entity and a second entity means one of (1) the first entity, (2) the second entity, and (3) the first entity and the second entity. Multiple entity listed with "and/or" should be construed in the same manner, i.e., "one or more" of the entity so conjoined. Other entity can optionally be present other than the entity specifically identified by the "and/or" clause, whether related or unrelated to those entities specifically identified.

Where numerical ranges are mentioned herein, the invention includes embodiments in which the endpoints are included, embodiments in which both endpoints are excluded, and embodiments in which one endpoint is included and the other is excluded. It should be assumed that both endpoints are included unless indicated otherwise. Furthermore, unless otherwise indicated or otherwise evident from the context and understanding of one of ordinary skill in the art.

In the event that any patents, patent applications, or other references are incorporated by reference herein and (1) define a term in a manner that is inconsistent with and/or (2) are otherwise inconsistent with, either the non-incorporated portion of the present disclosure or any of the other incorporated references, the non-incorporated portion of the present disclosure shall control, and the term or incorporated disclosure therein shall only control with respect to the reference in which the term is defined and/or the incorporated disclosure was present originally.

What is claimed is:

1. A device for assaying a target cell and a non-cell analyte in a sample, comprising:
   a first plate, a second plate, a plurality of spacers, a plurality of particles, and a capture agent, wherein:
   a) the first and second plates are movable relative to each other into different configurations, including an open configuration and a closed configuration;
   b) each of the plates has, on its respective surface, a sample contact area for contacting a sample that contains or is suspected of containing one or more target cells and a non-cell analyte;
   c) the spacers comprise an array of pillars that have a predetermined inter-spacer distance and a uniform height of 150 µm or less and are fixed on the first plate;
   d) the particles have a size of 0.2 µm to 100 µm, are equal to or less than the height of the spacers, and are, in an open configuration, distributed in one of the sample contact areas; and
   e) the capture agent is attached on the particles, wherein the capture agent binds the non-cell analyte;
   wherein in the open configuration, the two plates are separated apart, and the sample is deposited on one or both plates;
   wherein in the closed configuration, which is configured after a sample is deposited in the open configuration, a relevant sample volume is compressed by the first and second plates into a layer of substantially uniform thickness and is substantially stagnant relative to the first and second plates, and the thickness of the layer is confined by the first and second plates and is regulated by the first and second plates and the spacers;
   wherein the relevant sample volume is a portion of the sample containing or suspected of containing the non-cell analyte and the target cells to be analyzed; and
   wherein the height of the spacers and the geometry of the particles are configured to make, in the closed configuration, no significant overlaps between the one or more target cells, between the particles, and between the target cells and the particles.

2. A method for assaying a target cell and a non-cell analyte in a sample, comprising:
   a) having the device of claim 1;
   b) depositing, in the open configuration of the first and second plates, a sample that contains or is suspected of containing a target cell and a non-cell analyte;

c) having, after (b), the first and second plates in the closed configuration;
d) imaging, using an imager and in the closed configuration of the plates, one or more images of the targeted cell and the labeled detection agent in the sample; and
e) analyzing the one or more images to detect an existence or an amount of the target cell and the non-cell analyte in the sample.

3. An apparatus for assaying a target cell and a non-cell analyte in a sample, comprising:
the device of claim 1;
an imager takes at least one image of a relevant sample volume; and
a processor,
wherein the processor is configured to process the at least one image to (i) detect the non-cell analyte by analyzing the images of the particles, and (ii) detect the target cell analyte.

4. A kit for assaying a target cell and a non-cell analyte in a sample, comprising:
the device of claim 1; and
a labeled detection agent;
wherein the capture agent, or the detection agent, or both of the capture agent and the detection agent binds specifically the non-cell analyte.

5. The device of claim 1, wherein the spacers are scale-markers that indicate the orientation of the plates.

6. The device of claim 1, wherein, in an opening configuration, the particles on the same plate that the spacers are fixed on.

7. The device of claim 1, further comprising a non-transitory computer readable medium that stores a machine learning algorithm.

8. The device of claim 1, further comprising an imager for obtaining an image of a relevant sample volume of the sample.

9. The device of claim 1, wherein the relevant sample volume is a portion or entire volume of the at least part of the sample, and wherein the number of the particles in the relevant sample volume are configured to be, in a closed configuration, at least 10.

10. The method of claim 2, wherein said cell selected from the group consisting of white blood cells, leukocytes, granulocytes, agranulocytes, myeloid cells, lymphoid cells, neutrophils, eosinophils, basophils, lymphocytes, T-cells, B-cells, natural killer cells, and monocytes; and wherein the non-cell analyte is CRP (C-Reactive Protein).

11. The device of claim 1, further comprising a processor for processing the image, wherein the processing comprises at least one of (i) detecting the non-cell analyte by analyzing one or more images of at least 10 particles, and (ii) detecting the target cell analyte.

12. The device of claim 1, wherein the one or more spacers are fixed onto a surface of the second plate.

13. The device of claim 1, wherein the spacers are a periodic array.

14. The device of claim 1, wherein the plurality of particles are randomly distributed in the sample contact area.

15. The device of claim 1, wherein the plurality of particles are periodically distributed in the sample contact area.

16. The device of claim 1, further comprising a staining reagent.

17. The device of claim 1, further comprising a labeled detection agent that is dry coated on one of the sample contact areas.

18. The device of claim 1, further comprising a labeled capture agent, wherein the capture agent and the labeled detection agent are for a competitive assay wherein each of the capture agent and labeled capture agent specifically capture either the non-cell analyte or a labeled detection agent, but not both.

19. The device of claim 1, wherein the spacers are periodic and have a period 120 μm or less.

20. The device of claim 1, wherein one of the plates is flexible, the thickness of the flexible plate times the Young's modulus of the flexible plate is in the range 60 to 750 GPa-μm, and the fourth power of the inter-spacer-distance (ISD) divided by the thickness of the flexible plate (h) and the Young's modulus (E) of the flexible plate, $ISD^4/(hE)$, is equal to or less than $10^6$ μm$^3$/GPa.

21. The device of claim 1, wherein the number of the particles in the relevant sample volume is configured to be, in a closed configuration, at least 10.

22. The device of claim 1, wherein the spacers have a center to center distance of 200 μm or less, and the Young's modulus of the spacers times the filling factor of the spacers is equal to or larger than 20 MPa, wherein the filling factor is the ratio of the spacer contact area to the total plate area; and wherein one of the plates is flexible, the thickness of the flexible plate times the Young's modulus of the flexible plate is in the range 60 to 750 GPa-μm, and the fourth power of the inter-spacer-distance (ISD) divided by the thickness of the flexible plate (h) and the Young's modulus (E) of the flexible plate, $ISD^4/(hE)$, is equal to or less than $10^6$ μm$^3$/GPa.

23. The device of claim 1, wherein the fourth power of the inter-spacer-distance (ISD) divided by the thickness of the flexible plate (h) and the Young's modulus (E) of the flexible plate, $ISD^4/(hE)$, is equal to or less than $10^5$ μm$^3$/Gpa and wherein one of the plates is flexible, the thickness of the flexible plate times the Young's modulus of the flexible plate is in the range 60 to 750 GPa-μm.

24. A method for assaying one or more target cells and a non-cell analyte in a liquid sample, comprising:
a) having the device of claim 1;
b) having a sample containing or suspected of containing one or more target cells and a non-cell analyte;
c) having an optical label that is capable of binding the non-cell analyte forming a labeled non-cell analyte;
d) depositing, in an open configuration, the sample of the sample contact area of the device,
e) making, after step (d) the device in the closed configuration, thereby compressing at least a portion of the sample into a layer having uniform thickness;
f) taking, using an imager, at least one image of a sample relevant sample volume, wherein the imager is capable of imaging the optical label and the target cell; and
g) analyzing at least one image to detect an existence or an amount of (i) the target cell and/or (ii) the non-cell analyte.

25. A method for assaying one or more target cells and a non-cell analyte in a liquid sample, comprising:
a) having the device of claim 1;
b) having a sample containing or suspected of containing one or more target cells and a non-cell analyte;
c) having an optical label that is capable of binding the non-cell analyte forming a labeled non-cell analyte;
d) depositing, in an open configuration, the sample of the sample contact area of the device,
e) making, after step (d) the device in the closed configuration, thereby compressing at least a portion of the sample into a layer having uniform thickness;

f) taking, using an imager, at least one image of the sample relevant sample volume, wherein the imager is capable of imaging the optical label and the target cell; and g) analyzing, using a processor, at least one image to detect an existence or an amount of (i) the target cell and/or (ii) the non-cell analyte;

wherein the processor is configured to process the at least one image to (i) detect the non-cell analyte by analyzing the images of at least 10 particles, and (ii) detect the target cell analyte.

26. The method of claim 2, wherein, in detection of the non-cell analyte, the analyzing the images of at least 10 particles is by digital counting, wherein in the digital counting, an existence or an amount of non-cell analyte in the sample is determined from the number or the percentage of the particles that have a light signal above a threshold value, wherein the percentage is the ratio of the number of the particles with a light signal above the threshold to the number of the breads with a light signal below the threshold.

27. The method of claim 2, wherein, in detection of the non-cell analyte, the analyzing the images of at least 10 particles is by an analog counting, wherein the analog counting determines an existence or an amount of non-cell analyte in the sample from the optical signal amplitude from all particles in the relevant sample area.

28. The method of claim 2, further comprising a step of taking two or more images of a common area/volume of the sample layer, wherein the common area of the sample layer is an area of the sample containing at least one particle of the one or more particles.

29. The device of claim 1, further comprising at least one imager that images two or more images wherein at least one image is dark field image and at least one is bright field image.

30. The device of claim 1, further comprising a reagent coated onto one or more surfaces of the first plate and/or the second plate.

31. The device of claim 1, wherein the particles have a density that are configured to (i) produce a monolayer of the particles between the plates and (ii) produce no substantial overlap between the particles between the plates.

32. The method of claim 2, wherein the particles are mixed with the sample prior to depositing the sample into the device.

33. The device of claim 1, wherein the particles are disposed on at least one of the first plate and the second plate prior to deposition of the sample, and wherein the one or more particles are mixed with the sample upon deposition of the sample onto the device.

34. The device of claim 1, wherein the particles have various shapes.

35. The device of claim 1, wherein the particles have a maximum dimension in the range of 0.05 µm to 100 µm.

36. The method of claim 2, wherein the non-cell analyte is detected using a competitive assay, comprising a step of providing a labeled competitive detection agent that competes with the non-cell analyte, if present, for binding to the capture agent for the analyte.

37. The method of claim 2, wherein the non-cell analyte is detected using a non-competing assay, comprising a step of providing a labeled detection agent that specifically binds to another binding site of the non-cell analyte, wherein another binding site is the binding set different from the binding site by the capture agent.

38. The method of claim 2, wherein one of the images is a direct image that comprises information of the topology and position of the particle in the common area; and the other image is a signal image that is configured to comprises signal from a labeled competitive detection agent as a major signal of the image.

39. The device of claim 1, wherein all spacers have the same shape and dimensions.

40. The method of claim 2, further comprising determining, using a mobile electronic device: (i) one or more first values corresponding an amount of said analyte associated with said one or more capture agents; and (ii) one or more second values corresponding to an amount of said one or more cells within said sample.

41. The device of claim 1, wherein said plurality of particles are removably coupled to said at least one of said first plate and said second plate.

42. The device of claim 1, wherein said plurality of particles are selected from the group consisting of glass particles, magnetic particles, polystyrene particles, plastic particle, latex particles, metallic particles, alloy particles, and the particles comprising metal and dielectrics.

43. The device of claim 1, wherein said plurality of particles comprises a first plurality of particles and a second plurality of particles, wherein said first plurality of particles comprise one or more first capture agents coupled thereto, and wherein said second plurality of particles comprise one or more second capture agents coupled thereto.

44. The device of claim 43, wherein said one or more first capture agents are capable of associating with a first epitope on said analyte, and wherein said one or more second capture agents are capable of associating with a second epitope on said analyte.

45. The device of claim 43, wherein said first plurality of particles is disposed along said first plate, and said second plurality of particles is disposed along said second plate.

46. The device of claim 43, wherein said first plurality of particles is selected from the group consisting of glass particles, magnetic particles, polystyrene particles, and latex particles.

47. The device of claim 43, wherein said second plurality of particles is selected from the group consisting of reporter molecules, a fluorescent molecule, a dye molecule, a non-selective dye molecule, and a redox-reactive molecule.

48. The device of claim 43, wherein at least one of said one or more first capture agents and said one or more second capture agents are capable of specifically associating with said analyte.

49. The device of claim 1, wherein said device further comprises one or more spacers and disposed along at least one of said first plate or said second plate.

50. The device of claim 1, wherein said one or more spacers determine a distance between said first plate and said second plate.

51. The device of claim 1 further comprising a staining agent, wherein the capture agent comprises an antibody.

52. The method of claim 2, wherein said cell is selected from the group consisting of white blood cells, leukocytes, granulocytes, agranulocytes, myeloid cells, lymphoid cells, neutrophils, eosinophils, basophils, lymphocytes, T-cells, B-cells, natural killer cells, and monocytes; where in the non-cell analyte is selected from alpha-fetoprotein, prostate-specific antigen, cardiac troponins, c-reactive protein (CRP), or human chorionic gonadotropin, a carcinogen, a marker for influenza virus, HPV, HBV, HCV, EBV, HIV, HSV, FeLV, FIV, Hanta virus, HTLV I, HTLV II or CMV infection, a marker for bacterial infection, a marker for fungal infection, or a marker for parasitic infection.

53. The device of claim 1, wherein said thickness of said at least a portion of said sample is at most about 100 micrometers, at most about 90 micrometers, at most about 80 micrometers, at most about 70 micrometers, at most about 60 micrometers, at most about 50 micrometers, at most about 40 micrometers, at most about 30 micrometers, at most about 25 micrometers, at most about 20 micrometers, at most about 15 micrometers, at most about 10 micrometers, at most about 5 micrometers, at most about 4 micrometers, at most about 3 micrometers, at most about 2 micrometers, at most about 1 micrometers, at most about 0.5 micrometers, or at most about 0.2 micrometers.

54. The device of claim 1, wherein said plurality of particles have various shapes.

55. The device of claim 1, wherein said plurality of particles have a maximum dimension of about 100 micrometers, about 90 micrometers, about 80 micrometers, about 70 micrometers, about 60 micrometers, about 50 micrometers, about 40 micrometers, about 30 micrometers, about 25 micrometers, about 20 micrometers, about 15 micrometers, about 10 micrometers, about 5 micrometers, about 4 micrometers, about 3 micrometers, about 2 micrometers, about 1 micrometers, about 0.5 micrometers, or about 0.2 micrometers.

56. The method of claim 2, wherein said target cells in the layer are disposed substantially as a non-confluent monolayer.

57. The method of claim 2, wherein said target cells in the layer are in suspension.

58. The method of claim 40, wherein said determining comprises obtaining one or more images of an area comprising said at least a portion of said sample within said space, wherein said imaged area includes at least one of said plurality of particles.

59. The method of claim 40, wherein said one or more first values correspond to an intensity of energy emitted by said particle.

60. The method of claim 40, further comprising contacting said sample with a cell dye capable of associating with said one or more cells.

61. The method of claim 60, wherein said one or more second values correspond to an intensity of energy emitted by said cell dye.

62. The method of claim 40, further comprising using an algorithm to determine a relationship between said one or more first values and said one or more second values.

63. The method of claim 62, further comprising classifying a level of infection in a subject from whom said sample was obtained based on said relationship between said one or more first values and said one or more second values.

64. The method of claim 63, wherein said infection is a viral infection, a bacterial infection, or a combination thereof.

65. The method of claim 2, wherein said cell is selected from the group consisting of white blood cells, leukocytes, granulocytes, agranulocytes, myeloid cells, lymphoid cells, neutrophils, eosinophils, basophils, lymphocytes, T-cells, B-cells, natural killer cells, and monocytes.

66. The method of claim 2, wherein said analyte is selected from the group consisting of a polypeptide, a protein, a tagged protein, a fusion protein, an antibody, a small molecule, a virus particle, a bacterium, C-reactive protein, and any fragment thereof.

67. The method of claim 2, further comprising contacting at least a portion of said sample with a competing detection agent capable of associating with said one or more capture agents.

68. The method of claim 67, wherein said competing detection agent competitively binds to said one or more capture agents with said analyte.

69. The method of claim 2, further comprising contacting at least a portion of said sample with a supplementary detection agent capable of associating with said analyte.

70. The method of claim 2, wherein said one or more capture agents are capable of associating with a first epitope on said analyte, and wherein said supplementary detection agent is capable of associating with a second epitope on said analyte.

71. The method of claim 2, wherein the imaging is performed in less than about 10 sec, less than about 20 sec, less than about 30 sec, less than about 40 sec, less than about 50 sec, less than about 60 sec, or less than about 120 sec.

72. The method of claim 2, wherein said method does not comprise contacting at least a portion of said sample with a wash buffer.

73. The method of claim 24, wherein steps (d) to (f) are performed in the absence of any washing steps.

74. The method of claim 2, wherein the first and second plates are pressed together in a closed configuration by hand.

75. The method of claim 2, wherein the non-cell analyte is a polypeptide, nucleic acid, or metabolite.

76. The method of claim 2, wherein the sample is an amniotic fluid, aqueous humour, vitreous humour, blood, whole blood, fractionated blood, plasma, serum, breast milk, cerebrospinal fluid, cerumen, chyle, chime, endolymph, perilymph, feces, gastric acid, gastric juice, lymph, mucus, nasal drainage, phlegm, pericardial fluid, peritoneal fluid, pleural fluid, pus, rheum, saliva, sebum, semen, sputum, sweat, synovial fluid, tears, vomit, urine, and exhaled breath condensate.

77. The method of claim 2, further comprising diagnosing a disease based on the results.

78. The method of claim 2, wherein the disease is cancer, an inflammatory disease or an infectious disease.

79. The method of claim 2, wherein the method detects multiple different non-cell analytes.

80. The method of claim 2, wherein the sample comprises one or more target cells.

81. The method of claim 2, wherein the sample comprises one or more non-cell analytes.

82. The method of claim 2, wherein the one or more images comprise two fluorescent images that each is imaged at a different wavelength.

83. The method of claim 2, wherein the one or more images comprise two fluorescent images that each is imaged at a different wavelength for observing either a staining signal of the WBCs or a signal from the anti-CRP detection antibody.

84. The method of claim 2, wherein the imager takes both fluorescent and bright-field images of a sample.

85. The apparatus of claim 3, further comprising a fluorescent illumination optics enables an excitation light to illuminate the sample partially from a waveguide formed between the two plates and partially from a backside of the two plates with a large oblique incidence angle.

86. The apparatus of claim 3, further comprising a bright-field illumination and fluorescent illumination.

87. The apparatus of claim 3, wherein one of the images is a direct image that comprises information of the topology and position of the particle in the common area; and the other image is a signal image that is configured to comprise signal from the labeled competitive detection agents as a major signal of the image.

88. The device of claim 1, further comprising a non-transitory computer readable medium that stores a machine learning algorithm for analyzing the one or more images.

89. The method of claim 2, wherein the images are analyzed using machine learning.

90. The method of claim 2, wherein the images are analyzed using a mixture of deep learning and computer vision.

91. The device of claim 1, further comprising a labeled detection agent that is capable of binding the non-cell analyte.

92. The method of claim 2, wherein the (d) of imaging performed after the step (c) of having the first and second plate in the closed configuration without having a washing step.

93. The method of claim 2, wherein analyzing cells and non-cell analytes in a sample is used to determine if the sample being analyzed was obtained from a subject having cancer.

94. The method of claim 2, wherein the analyzing comprises analysis of an amount of cells and non-cell analytes, and comparing those values against one or more reference value to determine if a subject from whom the analyzed sample was obtained has a condition.

95. The device of claim 1 further comprising acridine orange as staining agent and antibody as capture agent.

96. The method of claim 2, wherein the non-cell analyte and the target cells are in samples for human, veterinary, agriculture, foods, environments, drug testing.

97. The method of claim 2, wherein the sample is a tissue sample of the subject, comprising connective tissue, muscle tissue, nervous tissue, epithelial tissue, cartilage, cancerous sample, or bone.

98. The method of claim 2, wherein the sample is a whole blood, the non-cell analyte is CRP (C-Reactive Protein), and target cell analytes are WBC and lymphocyte.

99. The device of claim 1, wherein the diameter of the particles is 10 μum.

100. The method of claim 2, wherein the diameter of the particles is 10 μm.

101. The device of claim 1, wherein the diameter of the particles is 10 μm and the spacer height is 10 μm.

102. The device of claim 1, further comprising a detection agent, wherein the detection agent specifically binds to the capture agent and competes with the non-cell analyte in binding to the capture agent.

103. The device of claim 1, further comprising a detection agent, wherein the capture agent and the detection agent bind to non-cell analyte forming a sandwich.

104. The device of claim 1 further comprising a mobile phone.

105. The apparatus of claim 3 further comprising a bright-field illumination optics for capturing bright-field microscopy images of a sample; and a fluorescent illumination optics for capturing fluorescent microscopy images of a sample.

106. The method of claim 2, wherein the sample thickness in a closed configuration is at most 20 μm.

* * * * *